United States Patent
Kim et al.

(10) Patent No.: US 9,944,713 B2
(45) Date of Patent: Apr. 17, 2018

(54) ANTIBODY SPECIFIC TO THE AIMP2-DX2

(71) Applicant: Medicinal Bioconvergence Research Center, Suwon-si (KR)

(72) Inventors: Sunghoon Kim, Seoul (KR); Jin Woo Choi, Seoul (KR)

(73) Assignee: Medicinal Bioconvergence Research Center, Suwon-si (KR)

( * ) Notice: Subject to any disclaimer, the term of this patent is extended or adjusted under 35 U.S.C. 154(b) by 0 days.

(21) Appl. No.: 15/074,498

(22) Filed: Mar. 18, 2016

(65) Prior Publication Data

US 2016/0272721 A1    Sep. 22, 2016

Related U.S. Application Data

(60) Continuation-in-part of application No. 13/011,386, filed on Jan. 21, 2011, which is a division of application No. 12/255,943, filed on Oct. 22, 2008, now Pat. No. 8,003,780, which is a continuation-in-part of application No. 11/264,725, filed on Nov. 1, 2005, now Pat. No. 7,459,529.

(30) Foreign Application Priority Data

Nov. 24, 2004  (KR) .................. 10-2004-0097164
May 10, 2005   (KR) .................. 10-2005-0039073

(51) Int. Cl.
*C07K 16/30*     (2006.01)
*G01N 33/574*    (2006.01)
*C12Q 1/68*      (2018.01)

(52) U.S. Cl.
CPC .......... *C07K 16/30* (2013.01); *C07K 16/3015* (2013.01); *C07K 16/3023* (2013.01); *C07K 16/3046* (2013.01); *C07K 16/3069* (2013.01); *C12Q 1/6886* (2013.01); *G01N 33/57407* (2013.01); *G01N 33/57423* (2013.01); *G01N 33/57438* (2013.01); *C07K 2317/24* (2013.01); *C07K 2317/34* (2013.01); *C07K 2317/55* (2013.01); *C07K 2317/565* (2013.01); *C12Q 2600/136* (2013.01); *C12Q 2600/158* (2013.01); *G01N 2500/04* (2013.01)

(58) Field of Classification Search
None
See application file for complete search history.

(56) References Cited

U.S. PATENT DOCUMENTS

| | | |
|---|---|---|
| 4,224,179 A | 9/1980 | Schneider |
| 4,231,877 A | 11/1980 | Yamauchi et al. |
| 4,235,871 A | 11/1980 | Papahadjopoulos et al. |
| 4,247,411 A | 1/1981 | Vanlerberghe et al. |
| 4,394,448 A | 7/1983 | Szoka, Jr. et al. |
| 4,673,567 A | 6/1987 | Jizomoto |
| 4,753,788 A | 6/1988 | Gamble |
| 4,814,270 A | 3/1989 | Piran |
| 4,897,355 A | 1/1990 | Eppstein et al. |
| 4,994,374 A | 2/1991 | Nishikawa et al. |
| 5,138,045 A | 8/1992 | Cook et al. |
| 5,175,084 A | 12/1992 | Inoue et al. |
| 5,218,105 A | 6/1993 | Cook et al. |
| 5,283,317 A | 2/1994 | Saifer et al. |
| 5,459,255 A | 10/1995 | Cook et al. |
| 5,605,804 A | 2/1997 | Allard et al. |
| 5,744,585 A | 4/1998 | Medenica et al. |
| 5,773,579 A | 6/1998 | Torczynski et al. |
| 6,117,987 A | 9/2000 | Torczynski et al. |
| 6,326,193 B1 | 12/2001 | Liu et al. |
| 6,737,514 B1 | 5/2004 | Wang et al. |
| 6,746,846 B1 | 6/2004 | Wang et al. |
| 7,070,940 B2 | 7/2006 | Corti et al. |
| 7,459,529 B2 | 12/2008 | Kim et al. |
| 8,431,393 B2 | 4/2013 | Kim et al. |
| 2002/0007051 A1 | 1/2002 | Cheo et al. |
| 2003/0068821 A1 | 4/2003 | Lois-Caballe et al. |
| 2004/0063120 A1 | 4/2004 | Beer et al. |
| 2004/0175375 A1 | 9/2004 | Kim et al. |
| 2004/0214763 A1 | 10/2004 | Corti et al. |
| 2005/0239731 A1 | 10/2005 | McSwiggen et al. |
| 2006/0110397 A1 | 3/2006 | Kim et al. |
| 2007/0015145 A1 | 1/2007 | Woolf et al. |
| 2007/0031844 A1 | 2/2007 | Khvorova et al. |
| 2008/0044439 A1 | 2/2008 | David |
| 2008/0199426 A1 | 8/2008 | Sukhatme et al. |
| 2009/0156536 A1 | 6/2009 | Kim et al. |
| 2011/0117572 A1 | 5/2011 | Kim et al. |

FOREIGN PATENT DOCUMENTS

| | | |
|---|---|---|
| EP | 0263740 | 4/1988 |
| EP | 0339097 | 8/1994 |
| EP | 0621480 | 10/1994 |
| EP | 0334962 | 4/1995 |
| EP | 0804451 | 9/1999 |
| EP | 1454628 | 9/2004 |
| KR | 10-2000-0019887 | 4/2000 |
| KR | 10-0394940 | 8/2003 |
| KR | 10-2004-0078035 | 9/2004 |
| KR | 10-0534563 | 12/2005 |
| KR | 10-2006-0057992 | 5/2006 |
| WO | 89/03849 | 5/1989 |
| WO | 94/10300 | 5/1994 |
| WO | 96/02552 | 2/1996 |

(Continued)

OTHER PUBLICATIONS

Nature 424:157-164, 2003.*
Tuschl et al., "The siRNA User Guideline: Selection of siRNA Duplexes form the Target mRNA sequence", pp. 1-7, 2004.
Non-Final Office Action dated Feb. 8, 2007 in U.S. Appl. No. 11/264,725.

(Continued)

*Primary Examiner* — Lei Yao
(74) *Attorney, Agent, or Firm* — H.C. Park & Associates, PLC

(57) ABSTRACT

Described herein are an antibody specifically binding to AIMP2-DX2 protein, and a diagnostic kit for detecting cancer which comprises the antibody specific to the AIMP2-DX2.

13 Claims, 50 Drawing Sheets

(56) References Cited

FOREIGN PATENT DOCUMENTS

| WO | 01/29058 | | 4/2001 |
|---|---|---|---|
| WO | WO2001075067 | * | 11/2001 |
| WO | 01/96584 | | 12/2001 |
| WO | 2004/005891 | | 1/2004 |

OTHER PUBLICATIONS

Final Office Action dated Sep. 7, 2007 in U.S. Appl. No. 11/264,725.
Notice of Allowance dated Aug. 6, 2008 in U.S. Appl. No. 11/264,725.
Affidavit dated Mar. 7, 2008 submitted in U.S. Appl. No. 11/264,725.
Non-Final Office Action dated Apr. 19, 2010 in U.S. Appl. No. 12/255,943.
Final Office Action dated Sep. 21, 2010 in U.S. Appl. No. 12/255,943.
Notice of Allowance dated Apr. 19, 2011 in U.S. Appl. No. 12/255,943.
Sambrook et al., "Molecular Cloning: A Laboratory Manual," Cold Spring Harbor Laboratory Press, pp. 16.3-16.36, 1989.
Non Final Office Action dated May 1, 2012 in U.S. Appl. No. 13/011,174.
Final Office Action dated Sep. 21, 2012 in U.S. Appl. No. 13/011,174.
Notice of Allowance dated Jan. 18, 2013 in U.S. Appl. No. 13/011,174.
Non-Final Office Action dated Aug. 21, 2014 in U.S. Appl. No. 13/011,386.
Final Office Action dated Dec. 5, 2014 in U.S. Appl. No. 13/011,386.
Non-Final Office Action dated Sep. 18, 2015 in U.S. Appl. No. 13/011,386.
Seung Bae Rho, et al., "Genetic dissection of protein-protein interactions in multi-tRNA synthetase complex", Proc. Natl. Acad. Sci. USA, vol. 96, pp. 4488-4493, Apr. 1999.
Nicholas C. Nicolaides, et al., "Analysis of the 5'Region ofPMS2Reveals Heterogeneous Transcripts and a Novel Overlapping Gene", Genomics, vol. 29, is.2pp. 329-334, Sep. 1995.
Mammalian Gene Collection (MGC) Program Team, "Generation and initial analysis of more than 15,000 full-length human and mouse cDNA sequences", Proc. Natl. Acad. Sci. USA, vol. 99(26), pp. 16899-16903, Dec. 24, 2002.
Needleman et al., "A General Method Applicable to the Search for Similarities in the Amino Acid Sequence of Two Proteins" J. Mol. Bio., vol. 48. pp. 443-453, 1970.
Table 4 of Hiller's Supplementary Information.
Kim et al., "Downregulation of FUSE-binding protein and c-myc by tRNA synthetase cofactor p38 is required for lung cell differentiation", Nat. Genet. 34:330-336, Jul. 2003.

* cited by examiner

RT primer: CAGCACCACGTCTGC

Primers for exon 1-3
1: TCTGACGGTTTCTGAGCGTT
5: AAGTGAATCCCAGCTGATAG

Primers for exon3-4
6: AGTGCTTTGGAGAACAGAAT
7: AAGAGCAGAGTTCATGGAGC

Primers for AIMP2-DX2
DX2-F: TGC TTT GGT TCT GCC ATG CCG
DX2-B: CGT AAT CCT GCA CGT GGC CAG si-cont si-DX2

SUV mean

| | before treatment | 8 weeks after treatment |
|---|---|---|
| EV-treated #1 | 0.456 | 1.812 |
| EV-treated #2 | 0.585 | 1.434 |
| shDX2-treated #1 | 0.510 | 1.106 |
| shDX2-treated #2 | 0.423 | 0.657 |

DX2 amino acid sequence

ANTIBODY SPECIFIC TO THE AIMP2-DX2

CROSS-REFERENCE TO RELATED APPLICATIONS

This application is a continuation-in-part of U.S. patent application Ser. No. 13/011,386 filed on Jan. 21, 2011, now abandoned, which is a divisional application of U.S. patent application Ser. No. 12/255,943, filed on Oct. 22, 2008, issued as U.S. Pat. No. 8,003,780, which is a continuation-in-part of U.S. patent application Ser. No. 11/264,725, filed on Nov. 1, 2005, issued as U.S. Pat. No. 7,459,529, which claims priority from Korean Patent Application Nos. 10-2004-0097164 and 10-2005-0039073, filed on Nov. 24, 2004 and May 10, 2005, respectively, which are all hereby incorporated by reference for all purposes as if fully set forth herein.

INCORPORATION-BY-REFERENCE OF SEQUENCE LISTING OR TABLE

In accordance with 37 CFR 1.821(e), please use the concurrently filed computer readable form Sequence Listing as the computer readable form Sequence listing for the instant application and the entire contents of the computer readable form Sequence Listings are hereby incorporated by reference:

| File Name | File Size | Creation Date |
|---|---|---|
| P6461USI1 updated sequence listinq.txt | 67 kb | May 9, 2016 |
| P6461USI1 sequence listing second update.txt | 70 kb | Oct. 3, 2017 |

BACKGROUND

Field

Exemplary embodiments relate to an antibody or an antibody fragment thereof specifically binding to AIMP2-DX2 protein. In particular, the present disclosure relates to an antibody or an antibody fragment thereof specifically binding to AIMP2-DX2 protein consisting of an amino acid sequence of SEQ ID NO: 2 or SEQ ID NO: 17. Other exemplary embodiments relate to a diagnostic kit for detecting cancer, the diagnostic kit comprising an antibody or an antibody fragment thereof specifically binding to AIMP2-DX2 protein.

Discussion of the Background

Cancer is generally diagnosed by radiography examinations such as X-ray radiography, computed tomography and bronchography or bronchoscopy examination. However, such methods provide no diagnostic data in terms of cell physiology molecular genetics, while they allow to determine anatomical progress of cancer. Lung and liver cancers are known to exhibit high incidence rate and mortality over the world.

To overcome shortcomings of such conventional examination technologies, a number of markers have been suggested for diagnosing lung or liver cancer as described hereunder:

Korean Pat. Appln. No. 10-1998-0038212 relating to the process for evaluating metastasis of lung cancer discloses that local metastatic lung cancer may be assessed by measuring the expression of mitogen activated protein kinase phosphatase-1 (MKP-1) in lung tissues. WO 2004/005891 suggests various disgnostic markers for lung cancer such as AOE372, ATP5D, B4GALT, Ppase, GRP58, GSTM4, P4HB, TPI and UCHL1. Monoclonal antibodies to LCGA have been proposed to diagnose and treat non-small cell lung carcinoma and ovary cancer as described in U.S. Pat. No. 6,117,981. EP 0804451 discloses a method for diagnosing and treating lung cancer by use of lung cancer-specific antigen HCAVIII. In addition, U.S. Pat. Nos. 6,746,846 and 6,737,514 and EP 0621480 also discuss lung cancer markers.

Korean Pat. Appln. No. 10-2000-0040609 discloses the early detection method for liver diseases including liver cirrhosis and cancer by measuring the level of asialoglycoproteins in accordance with sandwich assay in which lectins serve as a capture protein and/or probe protein. Korean Pat. Appln. No. 10-2002-0035260 describes that compositions comprising long-chain fatty-acid-Coenzyme A ligase 4, farnesyl diphosphate synthase, syndecan 2, emopamil-binding protein, preferentially expressed antigen in melanoma and histidine ammonia-lyase are useful in diagnosing human liver cancer. EP 0334962 suggests that the comparison of level of UDP-N-acetyglucosamine with that of glycoprotein N-acetylglucosamine transferase permits to detect liver cancer. Furthermore, EP 0339097 discloses diagnostic methods for liver cancer by measuring the level of inhibitors of collagenase in serum, plasma or synovia in a sandwich assay format.

However, markers for lung and liver cancers so far proposed permit restricted application in the senses that they are also detectable in normal cells. Therefore, assays or diagnostics using such markers are generally carried out by comparing their expression levels in normal and cancerous cells, resulting in unreliable and erroneous diagnosis.

Accordingly, there remains a need to propose novel diagnostic makers for lung or liver cancer.

Throughout this application, several patents and publications are referenced and citations are provided in parentheses. The disclosure of these patents and publications is incorporated into this application in order to more fully describe this invention and the state of the art to which this invention pertains.

The above information disclosed in this Background section is only for enhancement of understanding of the background of the invention and therefore it may contain information that does not form any part of the prior art nor what the prior art may suggest to a person of ordinary skill in the art.

SUMMARY OF THE INVENTION

Additional features of the invention will be set forth in the description which follows, and in part will be apparent from the description, or may be learned by practice of the invention.

Under such circumstances, the present inventors have made intensive research to develop a novel cancer-specific molecular species and a result, found that a variant of AIMP2 lacking exon 2, AIMP2-DX2 is specifically expressed in cancer cells, not in normal cells and permits to diagnose cancer occurrence in more reliable manner. In addition, the present inventors have discovered that antibody, siRNA and antisense oligonucleotide specific to AIMP2-DX2 allow to effectively treating cancer.

An exemplary embodiment discloses a AIMP2-DX2 protein with deleted exon 2 region of AIMP2.

An exemplary embodiment also discloses a nucleic acid molecule comprising a nucleotide sequence encoding the AIMP2-DX2 protein.

An exemplary embodiment further discloses a recombinant vector carrying a nucleotide sequence encoding the AIMP2-DX2 protein.

An exemplary embodiment still further discloses a transformant which is transformed with the recombinant vector carrying a nucleotide sequence encoding the AIMP2-DX2 protein.

An exemplary embodiment discloses an antibody specifically binding to the AIMP2-DX2 protein. In particular, an exemplary embodiment further discloses an antibody specifically binding to the AIMP2-DX2 protein consisting of an amino acid sequence of SEQ ID NO: 2 or SEQ ID NO: 17, without binding to AIMP2 protein.

An exemplary embodiment further discloses an antibody specifically binding to a junction region between exon 1 and exon 3 of the AIMP2-DX2 protein.

An exemplary embodiment still further discloses an antibody specifically binding to a polypeptide consisting of amino acid residues 42 to 52 (GHVQDYGALKD) (SEQ ID NO: 219) of the AIMP2-DX2 protein as shown in SEQ ID NO: 2 or SEQ ID NO: 17.

An exemplary embodiment still further discloses an antibody comprising:
  a heavy chain variable region comprising the following complementarity determining regions (CDRs): a heavy chain CDR1 as shown in SEQ ID NO: 160; a heavy chain CDR2 as shown in SEQ ID NO: 162; a heavy chain CDR3 as shown in SEQ ID NO: 164; and
  a light chain variable region comprising the following CDRs: a light chain CDR1 as shown in SEQ ID NO: 166; a light chain CDR2 as shown in SEQ ID NO: 168; and a light chain CDR3 as shown in SEQ ID NO: 170.

An exemplary embodiment still further discloses an antibody comprising a heavy chain variable region comprising the amino acid sequence of SEQ ID NO: 172 and a light chain variable region comprising the amino acid sequence of SEQ ID NO: 174.

An exemplary embodiment still further discloses an antibody wherein the antibody is an IgG antibody which comprises a heavy chain polypeptide comprising the amino acid sequence of SEQ ID NO: 176 and a light chain polypeptide comprising the amino acid sequence of SEQ ID NO: 178.

An exemplary embodiment still further discloses an antibody wherein the antibody fragment is an antibody fragment Fab which comprises a heavy chain polypeptide comprising the amino acid sequence of SEQ ID NO: 180 and a light chain polypeptide comprising the amino acid sequence of SEQ ID NO: 178.

An exemplary embodiment further discloses a diagnostic kit for cancer, which comprises an antibody of the AIMP2-DX2 protein.

An exemplary embodiment still further discloses a method for diagnosing cancer.

An exemplary embodiment discloses an antisense oligonucleotide which is complementary to a region of an mRNA of the AIMP2-DX2 protein.

An exemplary embodiment further discloses a pharmaceutical composition for treating cancer.

An exemplary embodiment still further discloses a method of screening for an agent which inhibits the formation of a heterodimer between the AIMP2-DX2 protein and the AIMP2 protein.

An exemplary embodiment still further discloses a method of screening for an agent which inhibits the expression of the AIMP2-DX2 gene.

An exemplary embodiment still further discloses an isolated siRNA (small interfering RNA) molecule comprising a sense region and an antisense region that down regulates expression of an AIMP2-DX2 gene via RNA interference (RNAi), wherein each strand of the siRNA molecules is independently about 18 to about 28 nucleotides in length, wherein one strand of the siRNA molecule comprises nucleotide sequence having sufficient complementarity to an RNA of the AIMP2-DX2 gene for the siRNA molecule to direct cleavage of the RNA via RNA interference.

An exemplary embodiment still further discloses a recombinant nucleic acid construct comprising a nucleic acid that is capable of directing transcription of a small interfering RNA (siRNA), the nucleic acid comprising: (a) at least one promoter; (b) a DNA polynucleotide segment that is operably linked to the promoter, the segment comprising nucleotide sequence having sufficient complementarity to an RNA of the AIMP2-DX2 gene for the siRNA molecule to direct cleavage of the RNA via RNA interference; (c) a linker sequence comprising at least 4 nucleotides operably linked to the DNA polynucleotide segment of (b); and (d) operably linked to the linker sequence a second polynucleotide of at least 18 nucleotides that is complementary to the segment of (b).

The foregoing general description and the following detailed description are exemplary and explanatory and are intended to provide further explanation of the claimed subject matter. Other objects and advantages of the present invention will become apparent from the detailed description to follow taken in conjugation with the appended claims and drawings.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

In FIG. 1a, the cells were incubated with the indicated concentrations (0, 2 and 4 ng/ml) of TGF-β1 for 6 hr. Thymidine incorporation in the untreated cells was taken as 1 and the values are the averages of four independent experiments. In FIG. 1b, AIMP2$^{+/+}$ and AIMP2$^{-/-}$ MEFs (14.5 day) were cultivated in the presence of TGF-β (2 ng/ml) for 4 day, fixed with paraformaldehyde, and the colonies were visualized by Giemsa staining. In FIG. 1c, MEFs were treated with TGF-β for 24 hr, and the portion of G0/G1 phase cells was determined by flow cytometry (FACS caliubur, Becton Dickinson, US). In FIG. 1d, MEFs were treated with TGF-β (2 ng/ml) for 1 hr. Smad2 and Smad3 were reacted with their specific antibodies and visualized by FITC-conjugated antibody (green). Nuclei were stained with PI (red). In FIG. 1e, the interactions of AIMP2 with Smad2 and Smad3 were tested by co-immunoprecipitation with antibodies against Smad2 and Smad3.

In FIG. 2a, A549 cells were harvested at the indicated times after treatment of TGF-β (2 ng/ml) and the extracted proteins were immunoprecipitated with anti-Smad2 or Smad3 antibody, and coprecipitation of AIMP2 was determined with anti-AIMP2 antibody. WCL stands for the Western blots of the proteins of whole cell lysates. In FIG. 2b, the expression of the TGF-β target genes, p15, p21 and PAI-1 was determined by RT-PCR in the control and AIMP2-transfected DU145. FIG. 2c demonstrates the effect of AIMP2 on the phosphorylation of Smad2 in AIMP2$^{-/-}$ MEFs. In FIG. 2d, the different domains of Smad2 (Mad-homology domain, MH1, MH2 and linker) were expressed as LexA fusion proteins and tested for the interaction with B42-fused AIMP2 by the blue colony formation on X-gal-containing yeast medium. In FIG. 2e, the TGF-β-dependent interaction of Smad2 with TGF-β receptor was determined by coimmunoprecipitation. MEFs were treated with TGF-β at 37° C. and incubated at 8° C. before immunoprecipitation. The association of TGF-β receptor with Smad2 was monitored by immunoblotting with anti-TβRI antibody (Santa Cruz biotech). FIG. 2f shows the time course of the total Smad2, phosphorylated Smad2 (p-Smad2), and AIMP2 levels in AIMP2$^{+/+}$ and AIMP2$^{-/-}$ MEFs after TGF-β treatment.

In FIG. 3b, "negative" indicates DU145 treated only with secondary antibody. 2000 cells were analyzed for each cell line. In FIG. 3c, the AIMP2 transcript level was compared by RT-PCR with different primer pairs. The transcripts spanning exons 3-4 and 1-3 were generated by the primer pairs of 6/7 and 1/5 (see FIG. 8b), respectively. GAPDH is a loading control. Note the generation of a smaller AIMP2 transcript from the primer pair for the transcript of exon 1-3. This smaller transcript is the alternative splicing form of AIMP2 lacking exon 2 (AIMP2-DX2). This transcript was produced only from the low-AIMP2 cell lines by RT-PCR with the primer AIMP2-DX2-F and the other one specific to the junction sequence between exon 1 and 3 (AIMP2-DX2-B) (see FIG. 8b). In FIG. 3d, TGF-β-dependent induction and nuclear translocation of AIMP2 were examined by immunofluorescence staining after the incubation with TGF-β for 2 hr. In FIG. 3e, the effect of TGF-β was compared on the proliferation of the indicated cells by [$^3$H] thymidine incorporation (n=4). In FIG. 3f, TGF-β-dependent induction of the target genes, p21 and PAI-1, was compared by RT-PCR after the incubation with TGF-β for 2 hr.

In FIG. 4a, AIMP2-DX2 was transfected into DU145 untreated or treated with TGF-β for 2 hr, and the AIMP2 level was determined by Western blotting. The expression of c-Myc, AIMP2-DX2 and GAPDH (control) was monitored by RT-PCR. In FIG. 4b, AIMP2-DX2 or empty vector was transfected into DU145, and its effect on the TGF-β-dependent cell growth inhibition was monitored by thymidine incorporation (n=4). In FIG. 4c, the interaction between AIMP2-F and AIMP2-DX2 was determined by yeast two hybrid assay as previously described (Rho, S. B. et al., PNAS. USA, 96:4488-93 (1999)). In FIG. 4d, AIMP2-F and AIMP2-DX2 were synthesized by in vitro translation in the presence of [$^{35}$S] methionine, mixed with either GST-AIMP2-F or -CDK2 (control), and precipitated with glutathione-Sepharose. The precipitated proteins were separated by SDS-PAGE and detected by autoradiography. In FIG. 4e, the interaction of AIMP2-F or AIMP2-DX2 with FUSE-binding protein (FBP; Kim, M. J. et al., Nat. Genet. 34:330-336:2003)) and Smad2 was determined by yeast two hybrid assay. In FIG. 4f, the effect of the proteasome inhibitor, ALLN (50 μM for 4 hr) on the levels of the full-length (F) and AIMP2-DX2 of AIMP2 was monitored in the AIMP2-DX2-generating H322 cells by Western blotting with anti-AIMP2 antibody. The AIMP2-DX2 form was confirmed by its co-migration in gel with its in vitro synthesized counterpart. In FIG. 4g, the increase of AIMP2 by the treatment of ALLN (20 μM for 2 hr) was also shown by immunofluorescence staining with anti-AIMP2 antibody in H322 cells. In FIG. 4h, myc-tagged AIMP2-DX2 was transfected to DU145 that were treated with ALLN. Then, AIMP2 was immunoprecipitated with anti-AIMP2 antibody, and the ubiquitinated AIMP2 molecules were monitored by immunoblotting with anti-ubiquitin antibody (Ubi).

In FIG. 5a, AIMP2-DX2 (or empty vector) was transfected into MEFs and monitored its effect on cell growth. The cells and colonies were visualized by light microscopy (top) and Giemsa staining (bottom), respectively. In FIG. 5b, siRNA targeting AIMP2-DX2 (si-DX2) was introduced into H322 and its suppressive effect on the AIMP2-DX2 transcript was determined by RT-PCR (top). si-DX2 did not affect the full-length AIMP2 transcript as shown by RT-PCR of the transcript for exon 3-4. The effect of si-DX2 on the phosphorylation of Smad2 and AIMP2 expression was also determined by Western blotting (bottom). The effect of si-DX2 on the restoration of the TGF-β signaling was also determined by immunofluorescence staining of p-Smad2 (FIG. 5c), TGF-β-dependent reporter assay under 3TP promoter (FIG. 5d) and growth arrest (FIG. 5e) using H322 cells. In FIG. 5c, p-Smad2 and nuclei were stained with FITC-conjugated secondary antibody (green) and PI (red), respectively, 30 min after TGF-β treatment. Notice that p-Smad2 was increased and nuclear located by the transfection of si-DX2.

In FIG. 6a, lung tumor formation was monitored at time interval after the intraperitoneal administration of benzo-(α)-pyrene into AIMP2$^{+/+}$ and AIMP2$^{+/-}$ mice. "N" stands for the number of the sacrificed mice. In FIG. 6b, total RNAs were isolated from the tissues, and subjected to RT-PCR with the AIMP2-DX2-specific primer. Normal and tumor tissues of the same patients (indicated by code number) were RT-PCR (FIG. 6c). In FIG. 6c, the exon 4 region of AIMP2 and GAPDH were used as control.

In FIG. 8a, the AIMP2 gene is composed of four exons encoding the polypeptides of the indicated size. FIG. 8b is the schematic representation for the locations of the primers used to generate the cDNAs spanning different regions of AIMP2 and their sequences (RT Primer: SEQ ID NO:15; primers for exon 1-3: SEQ ID NOs:5 and 6; primers for exon 3-4: SEQ ID Nos:3 and 4; and primers for AIMP2-DX2: SEQ ID Nos:8 and 7).

In FIG. 9a, to compare the AIMP2 levels between the AIMP2-DX2-positive and -negative cells, we cultured DU145 and H460 cells in one dish, and performed immunofluorescence staining with anti-AIMP2 antibody (green). The two cells lines were distinguished by immunofluorescence staining of p53 (red) since DU145 cells express p53 at high level due to its mutation, whereas H460 cells containing the wild type p53 maintain it at low level. The cells were treated with TGF-β for 2 hr, and fixed with methanol. In FIG. 9b, to address the effect of AIMP2-DX2 on expression of AIMP2, we monitored the AIMP2 level by flow cytometry. We transfected 2 µg/ml of empty vector or AIMP2-DX2 into DU145 cells, and incubated for 24 hr. The cells were then fixed with 70% ethanol and reacted with anti-AIMP2 antibody, and subsequently FITC-conjugated secondary antibody. In FIG. 9c, the effect of AIMP2-DX2 on the TGF-β-dependent cell cycle arrest was compared by flow cytometry. While the portion of the G0/G1 phase cells was increased in DU145 cells transfected with empty vector, but not in the AIMP2-DX2-transfected cells. The black and blues lines indicated the cells untreated and treated with TGF-β, respectively. In FIG. 9d, we compared the AIMP2 levels in H460 cells that were untreated (control) or treated with 10 .mu.M ALLN for 2 hr. "Negative" indicates the cells incubated only with FITC-conjugated secondary antibody.

In FIG. 12, the abbreviations, PCMV, BGH pA, fl ori, neomycin, ampicillin, SV40, SV40 pA, ColE1, T7 and Sp6 denote human cytomegalovirus immediate-early promoter, bovine growth hormone polyadenylation signal, fl replication origin, neomycin resistance gene, ampicillin resistance gene, SV40 replication origin, SV40 polyadenylation signal, ColE1 replication origin, T7 viral promoter and Sp6 viral promoter.

In FIG. 13a, apoptotic sensitivity of AIMP2 WT, hetero- and homozygous MEFs was compared by the cell count after the treatment of benzopyrene (BP) at time interval. In FIG. 13b, apoptotic cells were visualized (×100) by Apoptag staining in different tissues isolated from AIMP2$^{+/+}$ and AIMP2$^{-/-}$ neo-natal mice. In FIG. 13c, tumor susceptibility of AIMP2$^{+/+}$ and AIMP2$^{+/-}$ mice was compared by lung tumorigenesis induced by BP. From 6 weeks after the BP treatment, lungs were isolated and tumor formation was determined at the indicated times. Numbers on the bar indicate the number of the examined mice. In FIG. 13d, tumor formation in lung was confirmed by histological analysis (×100). Numbers indicate the different mouse id. In FIG. 13e, the relative expression of AIMP2-DX2 and -F were determined in adenocarcinoma (n=14) and normal (n=11) lung tissues by quantitative real-time RT-PCR. The cancer regions were obtained by laser microdissection system from archival formalin-fixed paraffin-embedded (FFPE) patient tissues for RT-PCR as described in Methods. Poly-A polymerase alpha (PAPOLA) was chosen as the reference gene for quantitative RT-PCR. The expression results were analyzed by Mann-Whitney test and statistical analyses were achieved using SPSS software (SPSS, Chicago, Ill.). Each dot represents the expression ratio of AIMP2-DX2 to -F and mean values were shown. The mean differences of P<0.05 were considered significant.

In FIG. 14a, mouse embryonic fibroblasts were transfected with EV (empty vector), AIMP2-F and -DX2 and selected by G418 to establish the stable cell lines. The colonies were selected from each transfectants and their ability to form anchorage-independent colonies was determined and represented as bar graph. In FIG. 14b, normal lung WI-26 cells were incubated in the presence of BP for 4 weeks. The surviving cells were further cultivated for another 4 weeks after removal of BP and the colonies were isolated. The expression of AIMP2-F and -DX2 in each isolated colonies was determined by Western blotting with anti-AIMP2 antibody. The ratios of AIMP2-DX2 to -F were shown. In FIG. 14c, the same numbers of the isolated colonies were plated and incubated to determine their ability to form anchorage-independent colony formation. The relationship between the ratio of AIMP2-DX2/F and the number of the resulting colonies was displayed as dot plot. In FIG. 14d, mouse embryonic fibroblasts were transfected with EV or AIMP2-DX2, and the cell lines stably expressing AIMP2-DX2 were established by G418 selection. The same numbers of the selected colonies were then injected to nude mice and checked their ability to form tumors. Among eight mice injected with AIMP2-DX2 transfectants, five mice generated tumors whereas none of the six mice injected with the empty vector transfectants formed tumors. In FIG. 14e, a couple of the representative mice injected with the EV- or DX2-transfectants are shown. In FIG. 14f, the expression of AIMP2-F and -DX2 was determined by Western blotting with anti-AIMP2 antibody in the three EV and AIMP2-DX2 transfectants. The tumors resulting from the injection of the AIMP2-DX2 transfectant were obtained and the expression fm AIMP2-F and -DX2 was determined by Western blotting with anti-AIMP2 antibody.

In FIG. 15a, the si-control and si-AIMP2-DX2 expressing NCI-H460 cells were injected into nude mice (n=6) and tumor volumes were measured at the indicated times. The si-control or -AIMP2-DX2 RNA was additionally delivered directly into the growing tumors on 17, 20 and 23 days after cell transplantation. In FIG. 15b, the representative photographs of the si-control and -AIMP2-DX2-injected tumors growing on the nude mice. In FIG. 15c, the si-control and -AIMP2-DX2-injected tumors were isolated and their volumes are compared in the same scale. The scale unit represents 0.5 cm. In FIG. 15d, the tumor growth of the si-control and -AIMP2-

DX2 expressing H460 cells that were injected into the nude mice (n=6). The tumor volumes were measured at the indicated times. In FIG. 15e, the histological characteristics of the isolated tumors are compared by hematoxylin and eosin staining between si-control and -DX2 injected tumors (upper, ×100). The cell death between the two tumors was monitored by Apoptag staining (lower, ×100). The apoptotic cells and nuclei are shown in green and blue fluorescence, respectively. In FIG. 15f, the si-control and si-AIMP2-DX2 of Table 1 were transfected H460 cells, respectively, and expression of AIMP2-F and AIMP2-DX2 were determined by western blotting with monoclonal antibody (clone number 324).

In FIG. 16a, the efficiency of si-AIMP2-DX2 and sh-AIMP2-DX2 in the suppression of AIMP2-DX2 was compared by Western blotting with anti-AIMP2 antibody. The siRNA targeting AIMP2-DX2 and the plasmid encoding sh-AIMP2-DX2 were introduced into A549 cells. In FIGS. 16b-16c, GFP-encoding plasmid was delivered into mouse lung via intranasal inhalation as described. After 2 days, the mice were sacrificed and various regions of the lungs were fixed by paraffin block. The plasmid delivery was then monitored by fluorescence. About 50% of the examined lung area was evaluated as GFP positive.

In FIG. 17c, the arrow heads indicate tumor nodules of the isolated lung lobes (upper) and the representative tumor area of the EV- and sh-DX2 treated lungs (lower). In FIG. 17d, the CT (top) and micro-PET (middle) scanning images were superimposed (bottom) to locate tumor region. The tumor sizes were determined by standardized uptake values (SUVs) of radioactive FDG as described in methods. Numbers indicate different mouse id. In FIG. 17e, the effect of sh-AIMP2-DX2 and EV plasmid delivery on the growth of lung tumors (n=2) was monitored by micro-PET analysis as described in Methods. The tumor sizes were reflected by standardized uptake values (SUVs) (shown in the table) using radioactive [18F] fluoro-2-deoxy-D-glucose (18FDG). The SUV values measured after the DNA delivery were divided by those before the treatment. In FIG. 17f, the lung tumors were induced by BP treatment that was accompanied by butylhydroxyltoluene to boost tumor progression. The effect of sh-AIMP2-DX2 on the survival of tumor-containing mice was determined after the last DNA administration at time interval and represented as line graph.

FIG. 18 is the result of Western blot analysis on H460 lung cancer cell lysate by using the H5 Fab in the presence of 100 μg/ml of an AIMP2-DX2 epitope peptide (which is amino acid residues 42 to 52 (GHVQDYGALKD) (SEQ ID NO: 219) of the AIMP2-DX2 protein as shown in SEQ ID NO: 2 or SEQ ID NO: 17) (indicated as "+") or the H5 Fab without the addition of the AIMP2-DX2 epitope peptide (indicated as "−"), respectively.

FIG. 19a is the result of Western blot analysis using the H5 Fab and the cell lysate of H460 lung cancer cells which were transfected with siRNAs targeting the AIMP2-DX2 (indicated as "DX2" for siDX2, "#1" for si exon 4 #1, and "#2" for si exon 4 #2, respectively) and followed by incubation for 72 hours. FIG. 19b shows each siRNA-targeting region used for this test. SiDX2 targets the exon 1-exon 3 junction region of the AIMP2-DX2, while si exon 4 #1 and #2 each target different regions of exon 4 of the AIMP2-DX2, respectively. "C" means a control group.

FIG. 20a shows a result of Western blot analysis using cell lysates of HEK293T cells which were transfected to express various isotypes of the AIMP2-DX2 protein, together with the H5 Fab in the presence of 100 μg/ml of the AIMP2-DX2 epitope peptide ("H5+epitope peptide") or H5 Fab in the absence of the AIMP2-DX2 epitope peptide ("H5"). Being fused with strep tag, the AIMP2-DX2 proteins expressed in HEK293T cells were the full-length AIMP2-DX2 protein ("F-DX2" or "F") and its N-terminal deleted isotypes ("42-DX2" or "42" for two (2) amino acid deletion; "423-DX2" or "423" for twenty three (23) amino acid deletion; "433-DX2" or "433" for thirty three (33) amino acid deletion), respectively. These results indicate that the H5 Fab recognizes various forms of the AIMP2-DX2 which contains the exemplary epitope peptide. "EV" means an empty vector. FIG. 20b shows a diagram the above AIMP2-DX2 proteins (exon 1, exon 3 and exon 4 are indicated in different shades, respectively; strep tag is comprised of thirty amino acids including a linker peptide) and their corresponding amino acid residues which are indicated with arrows.

As shown in FIG. 21a and FIG. 21b, the binding affinity between H5 IgG antibody and the AIMP2-DX2 epitope peptide was indicated in sensorgram. X axis of sensorgram indicates time (seconds, s), while y axis means response (response unit, RU). The description in a box indicates a concentration of the AIMP2-DX2 epitope peptide in nM.

DETAILED DESCRIPTION OF THE ILLUSTRATED EMBODIMENTS

Figure 1A:
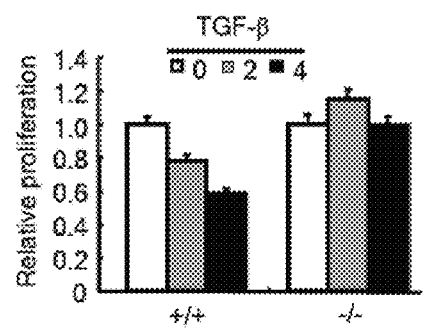
FIGS. 1a-1e represent the functional importance of AIMP2 in TGF-β signaling and its interaction with Smad2/3. AIMP2$^{+/+}$ and AIMP2$^{-/-}$ MEFs were compared in the effect of TGF-β on cell proliferation (FIG. 1a), colony formation (FIG. 1b), cell cycle progression (FIG. 1c), and nuclear translocation of Smad2 and Smad3 (FIG. 1d).

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements.

The present inventors elucidated that the genetic disruption of p38 (newly designated herein as "AIMP2") to induce overexpression of c-myc causes neonatal lethality in mice through over-proliferation of alveolar epithelial cells and transforming growth factor-β (TGF-β) induces AIMP2 expression and promoted its translocation to nuclei for the downregulation of c-myc (M. J. Kim, et al., Nat. Genet. 34:330-336 (2003)).

Following the previous research, the present inventors have revealed that AIMP2 is a novel tumor suppressor, playing a unique role in TGF-β signaling via interaction with Smad2/3. In addition, we have discovered that the aberrant variant of AIMP2 lacking exon II (AIMP2-DX2) is specifically expressed in cancer cell lines and tissues. The existence of AIMP2 lacking exon II (AIMP2-DX2) was verified by RT-PCR using combinations of AIMP2-specific primers. When the primers were used to generate AIMP2 cDNA spanning exon 3 and 4, the decrease of AIMP2 transcript was not observed in the cells showing the reduced level of AIMP2 in Western blot analysis. When we used the primers generating the transcript from exon 1 to 3, we obtained not only the transcript of the expected size, but also a smaller one. Sequencing analysis of this small transcript revealed that it lacks exon 2 encoding 69 amino acid residues of AIMP2. RT-PCR analysis using the primer targeting to the junction sequence of exon 1 and 3 showed that the cell lines expressing lower AIMP2 level generated the smaller transcript, confirming the generation of AIMP2-DX2.

Furthermore, the inventors observed that AIMP2 level was dramatically reduced regardless of TGF-β, demonstrating that the generation of AIMP2-DX2 leads to loss of AIMP2 activity. In addition to this, the introduction of AIMP2-DX2 elevated the expression of c-myc and relived the growth arrest by TGF-β. Surprisingly, we found that AIMP2-DX2 forms a heterodimer with AIMP2 that is ubiquitinated to be rapidly degraded by proteasome-dependent degradation process. Consequently, we are urged to reason that AIMP2-DX2 is closely associated with tumorigenesis by inducing the decrease of AIMP2 level. In vivo study provides additional evidences to verify that AIMP2-DX2 is strongly related to lung and liver cancer formation as well.

It should be noted that p38DX2 described in the priority documents of this application, i.e., the Korean Pat. Appln. Nos. 2004-0097164 and 2005-0039073 is newly named as AIMP2-DX2.

In one aspect of this disclosure, there is provided a AIMP2-DX2 protein comprising a AIMP2 amino acid sequence in which the exon 2 region of the AIMP2 amino acid sequence is deleted, that is specifically expressed in cancer cells, in particular, lung and liver cancer cells.

Preferably, the AIMP2-DX2 protein consists of the AIMP2 amino acid sequence in which the exon 2 region of the AIMP2 amino acid sequence is deleted.

The AIMP2-DX2 protein is a deletion variant of AIMP2 lacking exon 2. The amino acid sequence of the AIMP2 protein is found in several databases (312aa version: accession Nos. AAC50391.1 and GI:1215669; 320aa version: accession Nos. AAH13630.1, GI:15489023 and BC013630.1 available from GenBank) and publications (312aa version: Nicolaides, N. C., Kinzler, K. W. and Vogelstein, B. Analysis of the 5' region of PMS2 reveals heterogeneous transcripts and a novel overlapping gene, Genomics 29 (2):329-334(1995); 320 aa version: Generation and initial analysis of more than 15,000 full-length human and mouse cDNA sequences, Proc. Natl. Acad. Sci. U.S.A. 99(26): 16899-16903 (2002)). The amino acid sequence of the AIMP2-DX2 protein comprises, preferably, consists of that of AIMP2 lacking exon 2 region as aforedescribed known sequences. The Korean Pat. Appln. No. 10-2003-0018424 discloses cancer therapy efficacy of the AIMP2 protein, teachings of which are incorporated herein by reference in its entity.

In addition, the AIMP2-DX2 protein includes exon 2-deleted variant of AIMP2 equivalents, for example, functional equivalents resulting from substitution, deletion, insertion or their combinations of AIMP2 that exhibit substantially identical activity to the wild type AIMP2, or functional derivatives with modifications to alter physical and/or biochemical properties of the wild type AIMP2 that exhibit substantially identical activity to the wild type AIMP2.

The deletion of exon 2 in AIMP2 as described herein means that the amino acid sequence spanning exon 2 region in AIMP2 (corresponding to amino acid 46-114) is partially or wholly deleted to generate a deletion variant of AIMP2 capable of forming a heterodimer with AIMP2 to inhibit normal function of AIMP2 and promote degradation of AIMP2. Accordingly, the AIMP2-DX2 protein described herein may include any variant of AIMP2 with whole or partial exon 2 deletion in which exon 1, 3 and/or 4 is natural or modified by amino acid substitution, deletion or insertion, so long as the variant is able to form a heterodimer with AIMP2 to inhibit normal function of AIMP2. Preferably, the AIMP2-DX2 protein comprises a whole exon 2 deletion and intact exon 1, 3 and 4. More preferably, the AIMP2-DX2 protein comprises, most preferably, consists of an amino acid sequence of SEQ ID NO:2 or SEQ ID NO: 17.

The AIMP2-DX2 protein may comprise its natural-occurring amino acid sequences and variants having modified sequences as well, so long as the variants retain activity of the AIMP2-DX2 protein described above. The variants of the AIMP2-DX2 protein refer to proteins having different sequences from its natural-occurring amino acid sequence prepared by deletion, insertion, non-conserved or conserved substitution or their combinations. The silent alteration of amino acid residues not to substantially impair protein activity is well known to one skilled in the art (H. Neurath, R. L. Hill, The Proteins, Academic Press, New York, 1979). Such amino acid alteration includes, but is not limited to, Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly.

In addition, the AIMP2-DX2 protein may comprise post-translational modifications such as phosphorylation, sulfation, acrylation, glycosylation, methylation and farnesylation.

The AIMP2-DX2 protein and its variants may be obtained by the isolation from natural sources, synthesis (Merrifield, J. Amer. Chem. Soc. 85:2149-2156 (1963)) or recombinant DNA technology (Joseph Sambrook, et al., Molecular Cloning, A Laboratory Manual, Cold Spring Harbor Laboratory Press, Cold Spring Harbor, N.Y. (2001)). Where a recombinant DNA technology is applied, host cells are transformed with an expression vector carrying a nucleic acid molecule encoding AIMP2-DX2 and then cultured, followed by recovering the AIMP2-DX2 expressed.

As described previously, the AIMP2-DX2 protein is specifically expressed in a variety of cancer cells including breast cancer, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal cancer, anal cancer, colon cancer, fallopian tube carcinoma, endometrial carcinoma, cervical cancer, vulval cancer, vaginal carcinoma, Hodgkin's disease esophageal cancer, small intestine cancer, endocrine cancer, thyroid cancer, parathyroid cancer, adrenal cancer, soft tissue tumor, urethral cancer, penile cancer, prostate cancer, bronchogenic cancer, nasopharyngeal cancer, laryngeal cancer, chronic or acute leukemia, lymphocytic lymphoma, bladder cancer, kidney cancer, ureter cancer, renal cell carcinoma, renal pelvic carcinoma, CNS tumor, primary CNS lymphoma, bone marrow tumor, brain stem nerve gliomas and pituitary adenoma, in particular, lung and liver cancer tissues, demonstrating that the AIMP2-DX2 protein can serve as a cancer diagnostic marker.

In another aspect of this disclosure, there is provided a nucleic acid molecule comprising a nucleotide sequence encoding the AIMP2-DX2 protein described above. Preferably,
the nucleic acid molecule coding for the AIMP2-DX2 protein comprises a nucleotide sequence of SEQ ID NO:1. More preferably, the nucleic acid molecule according to an exemplary embodiment consists of a nucleotide sequence of SEQ ID NO:1 or SEQ ID NO:16.

It is well understood by the skilled artisan that homologous sequences due to codon degeneracy may be encompassed within the nucleic acid molecule according to an exemplary embodiment, showing at least 60%, preferably 80%, most preferably 90-95% nucleotide similarity to that of SEQ ID NO:1 or SEQ ID NO:16, as measured using one of the sequence comparison algorithms. Methods of alignment of sequences for comparison are well-known in the art. Various programs and alignment algorithms are described in: Smith and Waterman, Adv. Appl. Math. 2:482 (1981); Needleman and Wunsch, J. Mol. Bio. 48:443 (1970); Pearson and Lipman, Methods in Mol. Biol. 24: 307-31 (1988); Higgins and Sharp, Gene 73:237-44 (1988); Higgins and Sharp, CABIOS 5:151-3 (1989); Corpet et al., Nuc. Acids Res. 16:10881-90 (1988); Huang et al., Comp. Appl. BioSci. 8:155-65 (1992); and Pearson et al., Meth. Mol. Biol. 24:307-31 (1994). The NCBI Basic Local Alignment Search Tool (BLAST) (Altschul et al., J. Mol. Biol. 215:403-10 (1990)) is available from several sources, including the National Center for Biological Information (NBCl, Bethesda, Md.) and on the Internet, for use in connection with the sequence analysis programs blastp, blasm, blastx, tblastn and tblastx. It can be accessed at ncbi.nlm.nih.gov/BLAST/

The nucleic acid molecule according to an exemplary embodiment may be single- or double-chain DNA (cDNA and gDNA) or single-chain RNA (mRNA).

The nucleic acid molecule encoding the AIMP2-DX2 protein may be prepared by the isolation from natural sources, synthesis or recombinant DNA technology. The AIMP2-DX2 nucleic acid molecule may be included in a suitable vector to provide the AIMP2-DX2 protein.

In still another aspect of this disclosure, there is provided a recombinant vector which comprises a nucleic acid molecule comprising a nucleotide sequence encoding the AIMP2-DX2 protein.

The term "recombinant vector" used herein refers to a genetic carrier to express a protein or RNA of interest in a suitable host cell, comprising a corresponding foreign sequence operably linked to a nucleic acid expression control sequence (such as a promoter, signal sequence and array of transcription factor binding sites). The term "operably linked"
used herein refers to functional linkage between a nucleic acid expression control sequence and a second nucleic acid sequence of interest, wherein the expression control sequence affects transcription and/or translation of the nucleic acid corresponding to the second sequence. The vector according to an exemplary embodiment may be constructed according to conventional recombinant DNA technology in which site-specific DNA cleavage and ligation are performed using commercially available enzymes.

The vector according to an exemplary embodiment includes plasmid, cosmid, bacteriophage and viral vectors, but not limited to. The vector may comprise expression control elements such as promoter, operator, start and stop codons, polyadenylation signal and enhancer as well as signal or leader sequences for membrane targeting or secretion. The promoter used in vectors may be constitutive or inducible one. Furthermore, the vector may carry a selection marker for selecting host cells harboring the vector and a replication origin.

The signal sequence in the vector includes, but not limited to, PhoA and OmpA signal sequences for *Escherichia* host cells, α-amylase and subtilicin signal sequences for *Bacillus* host cells, MFα and SUC2 signal sequences for yeast host cells, and insulin, α-interferon and antibody molecule signal sequences for animal host cells.

In further aspect of this disclosure, there is provided a transformant which is transformed with the recombinant vector according to an exemplary embodiment described above.

The transformation may be carried out according to any known approach for transforming nucleic acid molecules into organism, cell, tissue or organ, including electroporation, protoplasm fusion, $CaPO_4$ precipitation, $CaCl_2$ precipitation, agitation using silicon carbamide fiber, *Agrobacterium*-mediated transformation, PEG, dextran sulfate and lipofectamine, but not limited to. A suitable transformation method may be selected based on the type of host cells.

A suitable host cell is generally decided in considering the expression level and post-translation modification. Host cells include, but not limited to, prokaryotic cells such as *Escherichia coli, Bacillus subtilis, Streptomyces, Pseudomonas, Proteus mirabilis* and *Staphylococcus*, fungi (e.g., *Aspergillus*), yeast (e.g., *Pichia pastoris, Saccharomyces cerevisiae, Schizosaccharomyces* and *Neurospora crassa*), insect cells, plant cells and mammalian cells.

In still further aspect of this disclosure, there is provided a process for preparing the AIMP2-DX2 protein by culturing transformed cells described previously.

The culturing is carried out by conventional methods known to those skilled in the art under conditions suitable to express the AIMP2-DX2 protein of interest.

The AIMP2-DX2 protein expressed may be purified by conventional methods, for example, salting out (e.g., ammonium sulfate and sodium phosphate precipitation), solvent precipitation (e.g., protein fractionation precipitation using acetone or ethanol), dialysis, gel filtration, ion exchange, reverse-phase column chromatography, ultrafiltration or their combinations (Sambrook et al., Molecular Cloning: A Laboratory Manual, 3rd Ed., Cold Spring Harbor Laboratory Press (2001); and Deutscher, M., Guide to Protein Purification Methods, Enzymology, vol. 182. Academic Press. Inc., San Diego, Calif. (1990)).

The term "cancer marker" used herein refers to a substance that provides information to evaluate cancer likelihood, occurrence or development by examining qualitatively or quantitatively its expression in tissues or cells. Preferably, the term means an organic biomolecule (e.g., protein, DNA and RNA) that is expressed in cancer cells in a different pattern from normal cells. The AIMP2-DX2 gene or protein according to an exemplary embodiment is specifically expressed in cancer cells but not in normal cells, permitting to accurately diagnose cancer (preferably, lung and liver cancer). Preferably, the cancer diagnosis using AIMP2-DX2 expression is performed in mRNA and/or protein level.

In another aspect of this disclosure, there is provided an antibody specific to the AIMP2-DX2 protein.

As used herein, the term "antibody" refers to a protein which specifically reacts with a target antigen and is involved with an immune response in a subject body, and includes, for instance, chimeric, humanized, fully human, and bispecific antibodies. An antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies. The antibodies or fragments thereof can be produced in hybridomas, by recombinant DNA techniques, or by enzymatic or chemical cleavage of intact antibodies.

Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, polyclonal antibodies, bispecific antibodies, chimeric antibodies, humanized antibodies, human antibodies, antibody fusions (sometimes referred to herein as "antibody conjugates"), and fragments thereof, respectively.

Naturally occurring antibody structural units typically comprise a tetramer. Each such tetramer typically is composed of two identical pairs of polypeptide chains, each pair having one full-length "light" chain and one full-length "heavy" chain. Each of heavy and light chains of an antibody includes a variable region and a constant region which are classified depending on a variability in its amino acid sequence. Depending on the type of antibody, the constant region of a heavy chain is comprised of three or four heavy chain constant regions (i.e., CH1, CH2 and CH3 for IgA, IgD and IgG antibodies; and CH4 for IgE and IgM antibodies), while the constant region of a light chain is comprised of one constant region (CL). On the contrary, the variable region of heavy or light chain is comprised of one heavy chain variable region (VH) or one light chain variable region (VL), respectively. A whole antibody is able to specifically bind to a target antigen via variable regions of its heavy and light chains. Being comprised of two pairs of heavy and light chains (HC/LC), a whole antibody possesses a dimeric specificity of binding to two target antigens via its two variable regions.

As described above, the amino-terminal portion of each chain in an antibody typically includes a variable region that is responsible for antigen recognition. The carboxyl-terminal portion of each chain typically defines a constant region that can be responsible for effector function. Human light chains are typically classified as kappa (κ) and lambda (λ) light chains. Heavy chains are typically classified as mu (μ), delta (δ), gamma (γ), alpha (α), or epsilon (ε), and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. The variable regions of each light/heavy chain pair typically form an antigen-binding site, while a region on a target antigen recognized by its corresponding antibody is called "epitope."

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4.

In certain embodiments, an antibody heavy chain binds to an antigen in the absence of an antibody light chain. In certain embodiments, an antibody light chain binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions.

Hereinafter, the exemplary embodiments will be described in more detail.

An exemplary embodiment relates to an antibody that specifically binds to the AIMP2-DX2 protein. More particularly, an exemplary embodiment relates to an antibody that specifically binds to the AIMP2-DX2 protein consisting of an amino acid sequence of SEQ ID NO: 2 or SEQ ID NO: 17, without binding to AIMP2 protein. As described above, the amino acid sequence of the AIMP2 protein are disclosed in two versions, i.e. 312aa or 320aa version as shown in SEQ ID NO: 217 or 218, respectively.

An exemplary embodiment further discloses an antibody specifically binding to a junction region between exon 1 and exon 3 of the AIMP2-DX2 protein.

An exemplary embodiment still further discloses an antibody specifically binding to a polypeptide consisting of amino acid residues 42 to 52 (GHVQDYGALKD)(SEQ ID NO: 219) of the AIMP2-DX2 protein as shown in SEQ ID NO: 2 or SEQ ID NO: 17. More particularly, an exemplary embodiment provides an antibody which specifically recognizes a polypeptide consisting of amino acid residues 42 to 52 (GHVQDYGALKD) (SEQ ID NO: 219) as shown in SEQ ID NO: 2 or SEQ ID NO: 17 as an epitope. The polypeptide consisting of amino acid residues 42 to 52 (GHVQDYGALKD) as shown in SEQ ID NO: 2 or SEQ ID NO: 17 (hereinafter, also referred to as "the exemplary AIMP2-DX2 epitope peptide") includes eleven (11) amino acids of the junction region between exon 1 and exon 3 of the AIMP2-DX2 protein of which exon 2 region is totally deleted from the AIMP2 protein. The N-terminal amino acid residues GHVQ (SEQ ID NO: 220) is an exon 1 portion of the AIMP2-DX2, while the C-terminal amino acid residues DYGALKD (SEQ ID NO: 221) is an exon 3 portion of the AIMP2-DX2. The exemplary AIMP2-DX2 epitope peptide is not present in the wild type AIMP2 protein which maintains its exon 2 intact. Thus, the antibody specifically recognizing the exemplary AIMP2-DX2 epitope peptide does not bind to the wild type AIMP2 protein, whereas specifically binding to the AIMP2-DX2 protein.

An exemplary embodiment still further discloses an antibody comprising:

- a heavy chain variable region comprising the following complementarity determining regions (CDRs): a heavy chain CDR1 as shown in SEQ ID NO: 160; a heavy chain CDR2 as shown in SEQ ID NO: 162; a heavy chain CDR3 as shown in SEQ ID NO: 164; and
- a light chain variable region comprising the following CDRs: a light chain CDR1 as shown in SEQ ID NO: 166; a light chain CDR2 as shown in SEQ ID NO: 168; and a light chain CDR3 as shown in SEQ ID NO: 170.

An exemplary embodiment still further discloses an antibody comprising a heavy chain variable region comprising the amino acid sequence of SEQ ID NO: 172 and a light chain variable region comprising the amino acid sequence of SEQ ID NO: 174.

An exemplary embodiment still further discloses an antibody wherein the antibody is an IgG antibody which comprises a heavy chain polypeptide comprising the amino acid sequence of SEQ ID NO: 176 and a light chain polypeptide comprising the amino acid sequence of SEQ ID NO: 178.

An exemplary embodiment still further discloses an antibody wherein the antibody is an antibody fragment Fab which comprises a heavy chain polypeptide comprising the amino acid sequence of SEQ ID NO: 180 and a light chain polypeptide comprising the amino acid sequence of SEQ ID NO: 178.

For an illustrative purpose, the present inventors conducted a screening process of phage-displayed Fab library in order to develop an antibody specifically binding to the AIMP2-DX2 protein by recognizing the exemplary AIMP2-DX2 polypeptide (GHVQDYGALKD)(SEQ ID NO: 219) as an epitope. Briefly speaking, the exemplary AIMP2-DX2 epitope polypeptide (GHVQDYGALKD) (SEQ ID NO: 219) was fused with C-terminal cysteine residue for conjugation to a carrier protein Keyhole limpet hemocyanin (KLH), followed by the injection of the exemplary AIMP2-DX2 epitope polypeptide conjugated to KLH into a rabbit for inducing an immune response. cDNAs for the variable regions of a rabbit antibody were synthesized from mRNAs extracted from the immunized rabbit spleen and conjugated to DNAs encoding the constant regions of human Fab antibody, followed by being inserted into a pComb3XTT vector used for phage display. E. coli was transformed with the prepared vector encoding the rabbit/human chimeric Fab and transfected with a helper phage to produce a Fab library. The Fab library was subjected to panning over the AIMP2-DX2 protein, resulting in the selection of clones which bind to the AIMP2-DX2 protein.

The present inventors confirmed that the H5 antibody and its antibody fragment Fab specifically bind to the AIMP2-DX2 protein through antigen pre-adsorption, antigen expression inhibition with siRNAs and the like. It was also found that the binding between the H5 antibody and the AIMP2-DX2 protein was not affected by the N-terminal amino acid deletion of the AIMP2-DX2 protein which is involved with the solubility of the AIMP2-DX2. Especially, while not binding to wild type AIMP2 protein at all, the H5 antibody and its antibody fragment Fab bind to the AIMP2-DX2 only and thus are very effective in selectively recognizing the AIMP2-DX2 protein.

The term "antibody" used herein means a protein molecule specifically directed toward an antigenic site. The antibody may refer to antibodies which specifically recognize AIMP2-DX2 with discriminating AIMP2, including polyclonal and monoclonal antibodies. The antibody as used herein may be a monoclonal antibody originated from a single B cell or a polyclonal antibody originated from multiple B cells. Preferably, the antibody may be a monoclonal antibody of which heavy and light chain amino acid residues are substantially identical. The antibody as used herein may be derived from an animal including mammals (such as human) and birds. The antibody may be a chimeric antibody containing antibody sequences derived from different species. Further, genetically engineered antibodies such as chimeric antibodies are also included. Non-human antibodies may be humanized by grafting non-human CDRs onto human framework and constant regions, or by incorporating the entire non-human variable domains. In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies may be produced in transgenic, non-human animals that have been engineered to contain human immunoglobulin genes.

Antibodies against the novel protein, AIMP2-DX2, may be prepared in accordance with conventional technologies known to one skilled in the art.

Polyclonal antibodies may be prepared according to known processes in which the AIMP2-DX2 protein as an immunogen is injected into animals and then antiserum is collected. Immunized animals include, but not limited to, goat, rabbit, sheep, monkey, horse, pig, cattle and dog.

Monoclonal antibodies may be prepared in accordance with a fusion method (Kohler and Milstein, European Journal of Immunology, 6:511-519 (1976)), a recombinant DNA method (U.S. Pat. No. 4,816,56) or a phage antibody library (Clackson et al, Nature, 352:624-628 (1991); and Marks et al, J. Mol. Biol., 222:58, 1-597 (1991)).

Antibodies against the AIMP2-DX2 protein may be an intact immunoglobulin molecule or its fragments containing antigen-binding site such as F(v), Fab, Fab' and F(ab')2.

The antibodies according to an exemplary embodiment specific to AIMP2-DX2 permit to diagnose cancer (such as lung and liver cancer) as well as to treat cancer by suppressing the activity of AIMP2-DX2. Where the antibodies are used as a therapeutic agent, they may be coupled to conventional therapeutic agents in direct or indirect (through a linker) manner.

There is no limitation in the type or the form of antibody or antibody fragment thereof according to an exemplary embodiment, as long as the antibody or antibody fragment thereof comprises the above described amino acid residues of CDRs, VHs, VLs, heavy chains and light chains. As used herein, the antibody may include IgG, IgA, IgM, IgE or IgD antibody. As used herein, the term "antibody fragment" refers to a fragment of an antibody which retains the specific binding affinity of the antibody against an antigen. The antibody fragment may include, but is not limited to, Fab, Fab', F(ab')$_2$, F(ab)$_2$, Fv, scFv and diabody. Antibody fragments which recognize specific antigenic determinant, i.e. epitope can be generated by known techniques in the art. A "Fab fragment" comprises one light chain and the $C_H1$ and variable regions of one heavy chain. The heavy chain of a Fab molecule cannot form a disulfide bond with another heavy chain molecule. A "Fab' fragment" comprises one light chain and a portion of one heavy chain that contains the VH domain and the $C_H1$ domain and also the region between the $C_H1$ and $C_H2$ domains, such that an interchain disulfide bond can be formed between the two heavy chains of two Fab' fragments to form an F(ab')$_2$ molecule. A "F(ab')$_2$ fragment" contains two light chains and two heavy chains containing a portion of the constant region between the C$_H$1 and C$_H$2 domains, such that an interchain disulfide bond is formed between the two heavy chains. A F(ab')$_2$ fragment thus is composed of two Fab' fragments that are held together by a disulfide bond between the two heavy chains. A "Fv fragment" comprises the variable regions from both the heavy and light chains, but lacks the constant regions. A "scFv (Single-chain variable fragment)" is a Fv molecule in which the heavy and light chain variable regions have been connected by a flexible linker to form a single polypeptide chain, which forms an antigen binding region. A "diabody" is a noncovalent dimer of single-chain Fv (scFv) fragment that consists of the heavy chain variable (V$_H$) and light chain variable (V$_L$) regions connected by a small peptide linker.

In case of preparing IgG antibody, heavy and light chain regions may be separately expressed in different cells and then reacted together in later process to produce a whole IgG antibody. Alternatively, heavy and light chain regions may be expressed in a single cell and produced as a whole IgG antibody inside the same cell.

The therapeutic agent coupled to the antibodies according to an exemplary embodiment includes, but not limited to, radionuclide (e.g., 131I, 90Y, 105Rh, 47Sc, 67Cu, 212Bi, 211At, 67Ga, 125I, 186Re, 188Re, 177Lu, 153Sm, 123I and 111In), drug (e.g., methotrexate and adriamycin), lymphokine (interferon), toxin (ricin, abrin and diphtheria) and heterofunctional antibody that forms a complex with other antibody to possess a bi-functional binding capacity both to cancer cell and effector cell (e.g., T killer cell).

The antibody according to an exemplary embodiment may be administered per se or in the form of a pharmaceutical composition.

The pharmaceutical composition comprising antibody may be formulated with a pharmaceutically acceptable carrier. The form of the pharmaceutical composition varies depending on the administration mode. Typically, the composition comprises one of surfactants for facilitating transmembrane delivery. Such surfactant includes steroid-derived compounds, cationic lipids such as N-[1-(2,3-dioleyloxy)propyl]-N,N,N-trimethylammonium chloride (DOTMA), cholesterol hemisuccinate and phosphatidyl glycerol.

The pharmaceutical composition comprising the antibody according to an exemplary embodiment is administered in a pharmaceutically effective amount to treat cancer or prevent cancer metastasis. The pharmaceutical composition may be administered in a single or multiple dosing regimen. The administration mode of the pharmaceutical composition includes parenteral, subcutaneous, intraperitoneal, intrapulmonary, intranasal, and local administration. Parenteral administration includes subcutaneous, intradermal, intramuscular, intravenous, intrabursa, intrasternal, intrathecal and intraperitoneal injection. The pharmaceutical composition is generally formulated in a pH range of 4-8 for antibody stability (chemical and physical stability) and safety. In addition, the pharmaceutical composition may be formulated in an oral dosing form. Typical dose is optimized using standard clinical techniques.

Furthermore, the antibody according to an exemplary embodiment may be administered in a form of nucleic acid molecule to induce in vivo production of antibody (WO 96/07321).

In still another aspect of this disclosure, there is provided a diagnostic kit for cancer, which comprises an antibody specific to the AIMP2-DX2 protein.

The cancer diagnosis kit according to an exemplary embodiment may comprise antibody specific to AIMP2-DX2 as well as general instruments and reagents for immunoassay including carrier, detectable signal-generating label, dissolving agent, washing agent, buffer and stabilizer. Where an enzyme is used as a label, its substrate and reaction quencher may be included. Non-limiting examples of carrier include soluble carriers, for example, physiologically acceptable buffer known in the art (e.g. PBS), insoluble carriers, for example, polystyrene, polyethylene, polypropylene, polyester, polyacrylonitrile, fluorine resin, cross-linked dextran, polysaccharides, polymers such as magnetic microparticles made of latex coated with a metal, paper, glass, metals, agarose and combinations thereof.

Non-limiting examples of the assay system useful in the cancer diagnosis kit according to an exemplary embodiment include ELISA plates, dip-stick devices, immunochromatography test strips and radial partition immunoassay devices and flow-through devices.

In further aspect of this disclosure, there is provided a method for diagnosing cancer, which comprises the steps of: (a) providing a sample to be assayed; and (b) detecting in the sample an expression of a nucleotide sequence encoding the AIMP2-DX2 protein of claim 1, wherein the detection of the expression of the nucleotide sequence encoding the AIMP2-DX2 protein is indicative of cancer.

The sample used in the present disclosure includes any biological sample such as tissue, cell, whole blood, serum, plasma, saliva, semen, urine, synovia and spinal fluid and may be pretreated for assay.

The present method may be carried out at protein or mRNA level. Where it is performed to detect the AIMP2-DX2 protein, antibodies to specifically recognize the AIMP2-DX2 protein are used and the detection is carried out by contacting the sample to the antibody specific to the AIMP2-DX2 protein and evaluating a formation of antigen-antibody complex. The evaluation on antigen-antibody complex formation may be carried out using immunohistochemical staining, radioimmunoassay (RIA), enzyme-linked immunosorbent assay (ELISA), Western blotting, immunoprecipitation assay, immunodiffusion assay, complement fixation assay, FACS and protein chip assay. The evaluation on antigen-antibody complex formation may be performed qualitatively or quantitatively, in particular, by measuring signal from detection label.

The label to generate measurable signal for antigen-antibody complex formation includes, but not limited to, enzyme, fluorophore, ligand, luminophore, microparticle, redox molecules and radioisotopes. The enzymatic label includes, but not limited to, β-glucuronidase, β-D-glucosidase, β-D-galactosidase, urease, peroxidase, alkaline phosphatase, acetylcholinesterase, glucose oxidase, hexokinase, GDPase, RNase, luciferase, phosphofructokinase, phosphoenolpyruvate carboxylase, aspartate aminotransferase, phosphenolpyruvate decarboxylase, β-lactamase. The fluorescent label includes, but not limited to, fluorescein, isothiocyanate, rhodamine, phycoerythrin, phycocyanin, allophysocyanin, o-phthalate and fluorescamine. The ligand serving as a label includes, but not limited to, biotin derivatives. Non-limiting examples of the luminescent label includes acridinium ester, luciferin and luciferase. Microparticles as label include colloidal gold and colored latex, but not limited to. Redox molecules for labeling include ferrocene, lutenium complex compound, viologen, quinone, Ti ion, Cs ion, diimide, 1,4-benzoquinone, hydroquinone, $K_4W(CN)_8$, [OS (bpy)$_3$]$^{2+}$, [Ru(bpy)$_3$]$^{2+}$ and [Mo(CN).$_8$]$^{4-}$, but not limited to. The radioisotopes includes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I and $^{186}$Re, but not limited to.

Where the present method is performed to detect the AIMP2-DX2 mRNA, the detection step may be carried out by an amplification reaction or a hybridization reaction well-known in the art.

The phrase "detection of the AIMP2-DX2 mRNA" used herein is intended to refer to analyze the existence or amount of the AIMP2-DX2 mRNA as cancer diagnosis marker in cells by use of primer or probe specifically hybridized with the AIMP2-DX2 mRNA.

The term "primer" used herein means an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of four different nucleoside triphosphates and a thermostable enzyme in an appropriate buffer and at a suitable temperature.

The term "probe" used herein refers to a linear oligomer of natural or modified monomers or linkages, including deoxyribonucleotides, ribonucleotides and the like, which is capable of specifically hybridizing with a target nucleotide sequence, whether occurring naturally or produced synthetically. The probe used in the present method may be prepared in the form of oligonucleotide probe, single-stranded DNA probe, double-stranded DNA probe and RNA probe. It may be labeled with biotin, FITC, rhodamine, DIG and radioisotopes.

The method to detect the AIMP2-DX2 mRNA using either primer or probe includes, but not limited to, DNA sequencing, RT-PCR (reverse transcription-polymerase chain reaction), primer extension method (Nikiforov, T. T. et al., Nucl Acids Res 22, 4167-4175 (1994)), oligonucleotide ligation analysis (OLA) (Nickerson, D. A. et al., Pro Nat Acad Sci USA, 87, 8923-8927 (1990)), allele-specific PCR (Rust, S. et al., Nucl Acids Res, 6, 3623-3629 (1993)), RNase mismatch cleavage (Myers R. M. et al., Science, 230, 1242-1246 (1985)), single strand conformation polymorphism (SSCP; Orita M. et al., Pro Nat Acad Sci USA, 86, 2766-2770 (1989)), simultaneous analysis of SSCP and heteroduplex (Lee et al., Mol Cells, 5:668-672 (1995)), denaturation gradient gel electrophoresis (DGGE; Cariello N F. et al., Am J Hum Genet, 42, 726-734 (1988)) and denaturing high performance liquid chromatography (D-HPLC, Underhill Pa. et al., Genome Res, 7, 996-1005 (1997)).

Preferably, the method by amplification reaction is carried out by RT-PCR using a primer capable of differentiating an mRNA of AIMP2-DX2 from an mRNA of AIMP2. RT-PCR process suggested by P. Seeburg (1986) for RNA research involves PCR amplification of cDNA obtained from mRNA reverse transcription. For amplification, a primer pair specifically annealed to AIMP2-DX2 is used. Preferably, the primer is designed to generate two different sized bands in electrophoresis in which one is specific to the AIMP2 mRNA and the other to AIMP2-DX2 mRNA. Alternatively, the primer is designed to generate only electrophoresis band specific to AIMP2-DX2 mRNA. The primer pair to generate two different sized bands for the AIMP2 mRNA and AIMP2-DX2 mRNA is prepared to amplify a region corresponding to exon 2. The nucleotide sequence of such primers is not limited; most preferably, a primer set consisting of SEQ ID NOs:5 and 6. To observe only one electrophoresis band specific to AIMP2-DX2 mRNA, one of primers is designed to comprise the junction sequence between C-terminal of exon 1 and N-terminal of exon 3. In Examples described below, the primer of SEQ ID NO:8 annealed to the junction sequence is used together with the primer of SEQ ID NO:7 for RT-PCR. The RT-PCR analysis is convenient in the senses that cancer diagnosis is accomplished by observing the electrophoresis band pattern to evaluate expression of the AIMP2-DX2 mRNA.

The present method may be carried out in accordance with hybridization reaction using suitable probes.

The stringent conditions of nucleic acid hybridization suitable for forming such double stranded structures are described by Joseph Sambrook, et al., Molecular Cloning, A Laboratory Manual, Cold Spring Harbor Laboratory Press, Cold Spring Harbor, N.Y. (2001) and Haymes, B. D., et al., Nucleic Acid Hybridization, A Practical Approach, IRL Press, Washington, D.C. (1985). As used herein the term "stringent condition" refers to the conditions of temperature, ionic strength (buffer concentration), and the presence of other compounds such as organic solvents, under which hybridization or annealing is conducted. As understood by those of skill in the art, the stringent conditions are sequence dependent and are different under different environmental parameters. Longer sequences hybridize or anneal specifically at higher temperatures.

The probes used in the hybridization reaction have a AIMP2-DX2 specific nucleotide sequence which is not found in AIMP2. Preferably, the probes are designed to comprise the junction sequence between exons 1 and 3, most preferably, having the nucleotide sequence of SEQ ID NO: 8.

The present method is very useful in diagnosing a variety of cancer including breast cancer, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal cancer, anal cancer, colon cancer, fallopian tube carcinoma, endometrial carcinoma, cervical cancer, vulval cancer, vaginal carcinoma, Hodgkin's disease esophageal cancer, small intestine cancer, endocrine cancer, thyroid cancer, parathyroid cancer, adrenal cancer, soft tissue tumor, urethral cancer, penile cancer, prostate cancer, bronchogenic cancer, nasopharyngeal cancer, laryngeal cancer, chronic or acute leukemia, lymphocytic lymphoma, bladder cancer, kidney cancer, ureter cancer, renal cell carcinoma, renal pelvic carcinoma, CNS tumor, primary CNS lymphoma, bone marrow tumor, brain stem nerve gliomas and pituitary adenoma. More preferably, the present method is used for diagnosing lung cancer and liver cancer, most preferably, lung cancer.

In still further aspect of this disclosure, there is provided a siRNA (small interfering RNA) molecule which comprises a nucleotide sequence complementary to a region of an mRNA of the AIMP2-DX2 protein.

The siRNA according to an exemplary embodiment is not restricted to a RNA duplex of which two strands are completely paired and may comprise non-paired portion such as mismatched portion with non-complementary bases and bulge with no opposite bases. The overall length of the siRNA is 10-100 nucleotides, preferably, 15-80 nucleotides, and more preferably, 20-70 nucleotides. The siRNA may comprise either blunt or cohesive end so long as it enables to silent the AIMP2-DX2 expression due to RNAi effect. The cohesive end may be prepared in 3'-end overhanging structure or 5'-end overhanging structure. The overhanging bases are not limited in its length, for example, 1-8 nucleotides, preferably, 2-6 nucleotides. The overall length as described herein is expressed as the total of length of central double-stranded portion and terminal single-stranded overhanging portion. Furthermore, as long as AIMP2-DX2 siRNA is able to maintain its gene silencing effect on the target gene, it may contain a low molecular weight RNA (which may be a natural RNA molecule such as tRNA, rRNA or viral RNA, or an artificial RNA molecule), for example, in the overhanging portion at its either end. It is not necessary that both ends of AIMP2-DX2 siRNA have a cleavage structure. The AIMP2-DX2 siRNA according to an exemplary embodiment may comprise a stem-loop structure in which either end (head or tail) is connected via a linker. The length of the linker is not limited unless it impairs base pairing in stem structure. Particularly, the AIMP2-DX2 siRNA according to an exemplary embodiment comprises a duplex siRNA of the sense region having the nucleotide sequence selected from the group consisting of SEQ ID Nos: 27-154, and the antisense region having a sequence that is complementary to the nucleotide sequence selected from the group consisting of SEQ ID Nos: 27-154.

Sequence specific siRNA molecule according to an exemplary embodiment may be designed using one or more of several criteria. For example, to design a siRNA polynucleotide that has 18 consecutive nucleotides identical to a sequence encoding a polypeptide of interest (e.g., AIMP2-DX2), the open reading frame of the polynucleotide sequence may be scanned for 21-base sequences that have one or more of the following characteristics: (1) an A+T/G+C ratio of approximately 1:1 but no greater than 2:1 or 1:2; (2) an AA dinucleotide or a CA dinucleotide at the 5' end; (3) an internal hairpin loop melting temperature less than 55° C.; (4) a homodimer melting temperature of less than 37° C. (melting temperature calculations as described in (3) and (4) can be determined using computer software known to those skilled in the art); (5) a sequence of at least 16 consecutive nucleotides not identified as being present in any other known polynucleotide sequence (such an evaluation can be readily determined using computer programs available to a skilled artisan such as BLAST to search publicly available databases). Alternatively, a siRNA polynucleotide sequence may be designed and chosen using a computer software available commercially from various vendors (e.g., OligoEngine™ (Seattle, Wash.); Dharmacon, Inc. (Lafayette, Colo.); Ambion Inc. (Austin, Tex.); and QIAGEN, Inc. (Valencia, Calif.)). (See also Elbashir et al., Genes & Development 15:188-200 (2000); Elbashir et al., Nature 411:494-98 (2001); and [online] at mpipbc.gwdg.de/abteilungen/100/105/TUsch1_MIV2-_(3)_2002.

The siRNA polynucleotides may then be tested for their ability to interfere with the expression of the target polypeptide according to methods known in the art and described herein. The determination of the effectiveness of an siRNA polynucleotide includes not only consideration of its ability to interfere with polypeptide expression but also includes consideration of whether the siRNA polynucleotide manifests undesirably toxic effects, for example, apoptosis of a cell for which cell death is not a desired effect of RNA interference (e.g., interference of AIMP2-DX2 expression in a cell).

It should be appreciated that not all siRNAs designed using the above methods will be effective at silencing or interfering with expression of a desired target polypeptide. And further, that the siRNAs will effect silencing to different degrees. Such siRNAs must be tested for their effectiveness, and selections made therefrom based on the ability of a given siRNA to interfere with or modulate (e.g., decrease in a statistically significant manner) the expression of the target. Accordingly, identification of specific siRNA polynucleotide sequences that are capable of interfering with expression of a desired target polypeptide requires production and testing of each siRNA, as demonstrated in greater detail below (see Examples).

Furthermore, not all siRNAs that interfere with protein expression will have a physiologically important effect. The inventors here have designed, and describe herein, physiologically relevant assays for measuring the influence of modulated target polypeptide expression, for instance, cellular proliferation, induction of apoptosis, and/or altered levels of protein tyrosine phosphorylation (e.g., insulin receptor phosphorylation), to determine if the levels of interference with target protein expression that were observed using the siRNAs according to an exemplary embodiment have clinically relevant significance. Additionally, and according to non-limiting theory, one or more exemplary embodiments of the present invention applies altered (e.g., decreased or increased in a statistically significant manner) expression levels of one or more polypeptides of interest, and/or altered (i.e., increased or decreased) phosphorylation levels of one or more phosphoproteins of interest, which altered levels may result from impairment of target protein expression and/or cellular compensatory mechanisms that are induced in response to RNAi-mediated inhibition of a specific target polypeptide expression.

Persons having ordinary skill in the art will also readily appreciate that as a result of the degeneracy of the genetic code, many nucleotide sequences may encode a polypeptide as described herein. That is, an amino acid may be encoded by one of several different codons and a person skilled in the art can readily determine that while one particular nucleotide sequence may differ from another (which may be determined by alignment methods disclosed herein and known in the art), the sequences may encode polypeptides with identical amino acid sequences. By way of example, the amino acid leucine in a polypeptide may be encoded by one of six different codons (TTA, TTG, CTT, CTC, CTA, and CTG) as can serine (TCT, TCC, TCA, TCG, AGT, and AGC). Other amino acids, such as proline, alanine, and valine, for example, may be encoded by any one of four different codons (CCT, CCC, CCA, CCG for proline; GCT, GCC, GCA, GCG for alanine; and GTT, GTC, GTA, GTG for valine). Some of these polynucleotides bear minimal homology to the nucleotide sequence of any native gene. Nonetheless, polynucleotides that vary due to differences in codon usage are specifically contemplated.

Polynucleotides, including target polynucleotides, may be prepared using any of a variety of techniques, which will be useful for the preparation of specifically desired siRNA polynucleotides and for the identification and selection of desirable sequences to be used in siRNA polynucleotides. For example, a polynucleotide may be amplified from cDNA prepared from a suitable cell or tissue type. Such polynucleotides may be amplified via polymerase chain reaction (PCR). For this approach, sequence-specific primers may be designed based on the sequences provided herein and may be purchased or synthesized. An amplified portion may be used to isolate a full-length gene, or a desired portion thereof, from a suitable library (e.g., human skeletal muscle cDNA) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences. Suitable sequences for a siRNA polynucleotide contemplated may also be selected from a library of siRNA polynucleotide sequences.

For hybridization techniques, a partial sequence may be labeled (e.g., by nick-translation or end-labeling with .sup.32P) using well known techniques. A bacterial or bacteriophage library may then be screened by hybridizing filters containing denatured bacterial colonies (or lawns containing phage plaques) with the labeled probe (see, e.g., Sambrook et al., Molecular Cloning: A Laboratory Manual, Cold Spring Harbor Laboratories, Cold Spring Harbor, N.Y., 2001). Hybridizing colonies or plaques are selected and expanded, and the DNA is isolated for further analysis. Clones may be analyzed to determine the amount of additional sequence by, for example, PCR using a primer from the partial sequence and a primer from the vector. Restriction maps and partial sequences may be generated to identify one or more overlapping clones. A full-length cDNA molecule can be generated by ligating suitable fragments, using well known techniques.

A number of specific siRNA polynucleotide sequences useful for interfering with target polypeptide expression, and are presented in the Examples, the Drawings, and the Sequence Listing. SiRNA polynucleotides may generally be prepared by any method known in the art, including, for example, solid phase chemical synthesis. Modifications in a polynucleotide sequence may also be introduced using standard mutagenesis techniques, such as oligonucleotide-directed site-specific mutagenesis. Further, siRNAs may be chemically modified or conjugated to improve theur serum stability and/or delivery properties. Included as an aspect of this disclosure are the siRNAs described herein wherein the ribose has been removed therefrom. Alternatively, siRNA polynucleotide molecules may be generated by in vitro or in vivo transcription of suitable DNA sequences (e.g., polynucleotide sequences encoding a target polypeptide, or a desired portion thereof), provided that the DNA is incorporated into a vector with a suitable RNA polymerase promoter (such as T7, U6, H1, or SP6). In addition, a siRNA polynucleotide may be administered to a patient, as may be a DNA sequence (e.g., a recombinant nucleic acid construct as provided herein) that supports transcription (and optionally appropriate processing steps) such that a desired siRNA is generated in vivo.

Accordingly, a siRNA polynucleotide that is complementary to at least a portion of a target polypeptide-encoding sequence may be used to modulate gene expression, or as a probe or primer. Identification of siRNA polynucleotide sequences and DNA encoding genes for their targeted delivery involves techniques described herein. Identification of such siRNA polynucleotide sequences and DNA encoding genes for their targeted delivery involves techniques that are also described herein. As discussed above, siRNA polynucleotides exhibit desirable stability characteristics and may, but need not, be further designed to resist degradation by endogenous nucleolytic enzymes by using such linkages as phosphorothioate, methylphosphonate, sulfone, sulfate, ketyl, phosphorodithioate, phosphoramidate, phosphate esters, and other such linkages (see, e.g., Agrwal et al., Tetrahedron Lett. 28:3539-3542 (1987); Miller et al., J. Am. Chem. Soc. 93:6657-6665 (1971); Stec et al., Tetrahedron Lett. 26:2191-2194 (1985); Moody et al., Nucleic Acids Res. 12:4769-4782 (1989); Uznanski et al., Nucleic Acids Res. (1989); Letsinger et al., Tetrahedron 40:137-143 (1984); Eckstein, Annu. Rev. Biochem. 54:367402 (1985); Eckstein, Trends Biol. Sci. 14:97-100 (1989); Stein, In: Oligodeoxynucleotides. Antisense Inhibitors of Gene Expression, Cohen, ed., Macmillan Press, London, pp. 97-117 (1989); Jager et al., Biochemistry 27:7237-7246 (1988)).

Any polynucleotide according to an exemplary embodiment may be further modified to increase stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives, and cosmids. Vectors of particular interest include expression vectors, replication vectors, probe generation vectors, and sequencing vectors. In general, a suitable vector contains an origin of replication functional in at least one organism, convenient restriction endonuclease sites, and one or more selectable markers. (See, e.g., WO 01/96584; WO 01/29058; U.S. Pat. No. 6,326,193; U.S. 2002/0007051). Other elements will depend upon the desired use, and will be apparent to those having ordinary skill in the art. For example, one or more exemplary embodiments of the present invention contemplates the use of siRNA polynucleotide sequences in the preparation of recombinant nucleic acid constructs including vectors for interfering with the expression of a desired target polypeptide such as an AIMP2-DX2 or a chemotherapeutic target polypeptide in vivo; one or more exemplary embodiments of the invention also contemplates the generation of siRNA transgenic or "knock-out" animals and cells (e.g., cells, cell clones, lines or lineages, or organisms in which expression of one or more desired polypeptides (e.g., a target polypeptide) is fully or partially compromised). An siRNA polynucleotide that is capable of interfering with expression of a desired polypeptide (e.g., a target polypeptide) as provided herein thus includes any siRNA polynucleotide that, when contacted with a subject or biological source as provided herein under conditions and for a time sufficient for target polypeptide expression to take place in the absence of the siRNA polynucleotide, results in a statistically significant decrease (alternatively referred to as "knockdown" of expression) in the level of target polypeptide expression that can be detected. Preferably the decrease is greater than 10%, more preferably greater than 20%, more preferably greater than 30%, more preferably greater than 40%, 50%, 60%, 70%, 75%, 80%, 85%, 90%, 95% or 98% relative to the expression level of the polypeptide detected in the absence of the siRNA, using conventional methods for determining polypeptide expression as known to the art and provided herein. Preferably, the presence of the siRNA polynucleotide in a cell does not result in or cause any undesired toxic effects, for example, apoptosis or death of a cell in which apoptosis is not a desired effect of RNA interference.

Within certain embodiments, siRNA polynucleotides may be formulated so as to permit entry into a cell of a mammal, and expression therein. Such formulations are particularly useful for therapeutic purposes, as described below. Those having ordinary skill in the art will appreciate that there are many ways to achieve expression of a polynucleotide in a target cell, and any suitable method may be employed. For example, a polynucleotide may be incorporated into a viral vector using well known techniques (see also, e.g., U.S. 2003/0068821). A viral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those having ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Within other embodiments, one or more promoters may be identified, isolated and/or incorporated into recombinant nucleic acid constructs according to an exemplary embodiment, using standard techniques. The present disclosure provides nucleic acid molecules comprising such a promoter sequence or one or more cis- or trans-acting regulatory elements thereof. Such regulatory elements may enhance or suppress expression of a siRNA. A 5' flanking region may be generated using standard techniques, based on the genomic sequence provided herein. If necessary, additional 5' sequences may be generated using PCR-based or other standard methods. The 5' region may be subcloned and sequenced using standard methods. Primer extension and/or RNase protection analyses may be used to verify the transcriptional start site deduced from the cDNA.

To define the boundary of the promoter region, putative promoter inserts of varying sizes may be subcloned into a heterologous expression system containing a suitable reporter gene without a promoter or enhancer. Suitable reporter genes may include genes encoding luciferase, beta-galactosidase, chloramphenicol acetyl transferase, secreted alkaline phosphatase, or the Green Fluorescent Protein gene (see, e.g., Ui-Tei et al., FEBS Lett. 479:79-82 (2000). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Once a functional promoter is identified, cis- and trans-acting elements may be located. Cis-acting sequences may generally be identified based on homology to previously characterized transcriptional motifs. Point mutations may then be generated within the identified sequences to evaluate the regulatory role of such sequences. Such mutations may be generated using site-specific mutagenesis techniques or a PCR-based strategy. The altered promoter is then cloned into a reporter gene expression vector, as described above, and the effect of the mutation on reporter gene expression is evaluated.

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U or T is denoted in the context of the present disclosure, the ability to substitute a T or U is implied, unless otherwise stated.

The phrase "duplex region" refers to the region in two complementary or substantially complementary polynucleotides that form base pairs with one another, either by Watson-Crick base pairing or any other manner that allows for a stabilized duplex between polynucleotide strands that are complementary or substantially complementary. For example, a polynucleotide strand having 21 nucleotide units can base pair with another polynucleotide of 21 nucleotide units, yet only 19 bases on each strand are complementary or substantially complementary, such that the "duplex region" has 19 base pairs. The remaining bases may, for example, exist as 5' and 3' overhangs. Further, within the duplex region, 100% complementarity is not required; substantial complementarity is allowable within a duplex region. Substantial complementarity refers to 79% or greater complementarity. For example, a mismatch in a duplex region consisting of 19 base pairs results in 94.7% complementarity, rendering the duplex region substantially complementary.

The term "target" is used in a variety of different forms throughout this document and is defined by the context in which it is used. "Target mRNA" refers to a messenger RNA to which a given siRNA can be directed against. "Target sequence" and "target site" refer to a sequence within the mRNA to which the sense strand of an siRNA shows varying degrees of homology and the antisense strand exhibits varying degrees of complementarity. The phrase "siRNA target" can refer to the gene, mRNA, or protein against which an siRNA is directed. Similarly, "target silencing" can refer to the state of a gene, or the corresponding mRNA or protein.

The siRNA consists of a sense RNA strand corresponding to target mRNA and an antisense RNA strand complementary to target mRNA. siRNA to inhibit expression of a target gene provides effective gene knock-down method or gene therapy method.

The term "specific" used herein in conjunction with siRNA is intended to express the inhibition of target gene expression with no influence on other genes. The siRNA according to an exemplary embodiment is specific to the AIMP2-DX gene.

It is preferred that the siRNA according to an exemplary embodiment comprise a sense strand containing a corresponding sequence to a junction sequence between exons 1 and 3 and an antisense strand containing a complementary sequence.

The phrase "inhibition of gene expression" means that the level of mRNA and/or protein generated from the target gene is quenched or reduced, which is induced by RNA interference via occurrence of mRNA cleavage.

The siRNA according to an exemplary embodiment may be synthesized in vitro and then introduced into cells via transfection. In addition, it may be transfected into cells in the form of siRNA expression vector or PCR-derived siRNA expression cassette. Suitable preparation and transfection methods may be determined in considering the experiment aim and target gene function.

The sequences and length of the siRNA are not limited as long as it enables to suppress the AIMP2-DX2 expression. 3 illustrative siRNA expression vectors to silence AIMP2-DX2 are found in Examples described hereunder, suppressing cellular level of AIMP2-DX2 and restoring AIMP2 function and TGF-β signal transduction.

The preferable siRNA according to an exemplary embodiment comprises a corresponding sequence to the junction sequence between exons 1 and 3 of the AIMP2-DX2 mRNA. More preferably, the siRNA according to an exemplary embodiment is a RNA duplex described as (i) No. 3 siRNA consisting of two RNA molecules expressed from nucleotide sequences of SEQ ID NOs:9 and 10, (ii) No. 4 siRNA consisting of two RNA molecules expressed from nucleotide sequences of SEQ ID NOs:11 and 12, or (iii) No. 5 siRNA consisting of two RNA molecules expressed from nucleotide sequences of SEQ ID NOs:13 and 14. The siRNA consisting of two RNA molecules expressed from nucleotide sequences of SEQ ID NOs:11 and 12 is most preferred. The single or mixed type of siRNA molecules may be used.

In another aspect of this disclosure, there is provided an antisense oligonucleotide which is complementary to a region of an mRNA of the AIMP2-DX2 protein.

The term "antisense oligonucleotide" used herein is intended to refer to nucleic acids, preferably, DNA, RNA or its derivatives, that are complementary to the base sequences of a target mRNA, characterized in that they binds to the target mRNA and interfere its translation to protein. The antisense oligonucleotide according to an exemplary embodiment means DNA or RNA sequences complementary and binding to AIMP2-DX2 mRNA, that are able to inhibit translation, translocation, maturation or other biological functions of AIMP2-DX2 mRNA. The antisense nucleic acid is 6-100, preferably, 8-60, more preferably, 10-40 nucleotides in length.

The antisense oligonucleotide may at least one modification in its base, sugar or backbone for its higher inhibition efficacy (De Mesmaeker et al., Curr Opin Struct Biol., 5(3):343-55 (1995)). The modified nucleic acid backbone comprises phosphorothioate, phosphotriester, methyl phosphonate, short chain alkyl or cycloalkyl intersugar linkages or short chain heteroatomic or heterocyclic intersugar linkages. The antisense oligonucleotide may also contain one or more substituted sugar moieties. The antisense nucleic acid may include one or more modified bases, for example, hypoxanthine, 6-methyladenine, 5-me pyrimidines (particularly, 5-methylcytosine), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyl adenines, 2-thiouracil, 2-thiothymine, 5-bromouracil, 5-hydroxymethyluracil, 8-azaguanine, 7-deazaguanine, N.sup.6(6-aminohexyl)adenine and 2,6-diaminopurine. Another modification of the oligonucleotides according to an exemplary embodiment involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., Proc. Natl. Acad. Sci. USA, 86:6553 (1989)), cholic acid (Manoharan et al. Bioorg. Med. Chem. Let., 4:1053 (1994)), a thioether, e.g., hexyl-S-tritylthiol (Manoharan et al. Ann. N.Y. Acad. Sci., 660:306 (1992); Manoharan et al. Bioorg. Med. Chem. Let., 3: 2765 (1993)), a thiocholesterol (Oberhauser et al., Nucl. Acids Res., 20:533 (1992)), an aliphatic chain, e.g., dodecandiol or undecyl residues (Saison-Behmoaras et al. EMBO J., 10:111 (1991); Kabanov et al. FEBS Lett., 259:327 (1990); Svinarchuk et al. Biochimie, 75:49 (1993), a phospholipid, e.g., di-hexadecyl-rac-glycerol or triethylammonium 1,2-di-O-hexadecyl-rac-glycero-3-H-phosphonate (Manoharan et al. Tetrahedron Lett., 36:3651 (1995); Shea et al. Nucl. Acids Res., 18:3777 (1990)), a polyamine or a polyethylene glycol chain (Manoharan et al. Nucleosides & Nucleotides, 14:969 (1995)), or adamantane acetic acid (Manoharan et al. Tetrahedron Lett., 36: 3651 (1995)). Oligonucleotides comprising lipophilic moieties, and methods for preparing such oligonucleotides are known in the art, for example, U.S. Pat. Nos. 5,138,045, 5,218,105 and 5,459, 255. The modifications described above enhance stability against nuclease degradation and increase affinity of the antisense oligonucleotide toward its target mRNA.

It is preferred that the antisense oligonucleotide specific to AIMP2-DX2 comprises a complementary sequence to a junction region between exons 1 and 3 of AIMP2-DX2 mRNA.

The antisense RNA molecule is conventionally synthesized in vitro and then transmitted to cells. In addition, it is intracellularly produced by transcription from foreign sequence. In vitro synthesis involves RNA polymerase I. In vivo transcription for preparing antisense RNA uses vector having origin of recognition region (MCS) in opposite orientation. The antisense RNA preferably comprises a translation stop codon for inhibiting translation to peptide.

In another aspect of this disclosure, there is provided a pharmaceutical composition for treating cancer, which comprises (a) the antisense oligonucleotide or siRNA specific to AIMP2-DX2 mRNA as an active ingredient; and (b) a pharmaceutically acceptable carrier.

In still another aspect of this disclosure, there is provided a method for treating cancer in a patient, which comprises administrating into the patient a pharmaceutical composition (a) the antisense oligonucleotide or siRNA specific to AIMP2-DX2 mRNA as an active ingredient; and (b) a pharmaceutically acceptable carrier.

The pharmaceutical composition comprising at least one of AIMP2-DX2 siRNAs or antisense oligonucleotides may contain additional agent to suppress tumor cell proliferation and to facilitate the transduction of siRNA or antisense nucleic acid, for example, liposome (U.S. Pat. Nos. 4,897, 355, 4,394,448, 4,235,871, 4,231,877, 4,224,179, 4,753,788, 4,673,567, 4,247,411 and 4,814,270), or lipophilic carrier including sterols such as cholesterol, cholate and deoxycholic acid. In addition, the siRNA or antisense nucleic acid is conjugated to cell-adsorbing peptides such as peptide hormones, antigens and peptide toxins (Haralambid et al, WO 89/03849; Lebleu et al., EP 0263740).

Where the pharmaceutical composition is formulated for oral administration, it may contain binder, lubricant, disintegrator, diluent, solubilizer, dispersing agent, stabilizer, suspending agent, pigment and sweetener. Where the pharmaceutical composition is formulated for injection, it may contain buffer, preservative, solubilizer, tonicity agent and stabilizer. For topical administration, the pharmaceutical composition may contain substrate, diluent, lubricant and preservative. The formulation of the pharmaceutical composition may be prepared by formulating with pharmaceutically acceptable carriers described above. For oral administration, the pharmaceutical composition may be in the form of tablet, troche, capsule, elixir, suspension, syrup and wafer. The injectable composition may be formulated in unit dosage ample or multi dosage form.

The correct dosage of the pharmaceutical compositions according to an exemplary embodiment comprising AIMP2-DX2 siRNA or antisense oligonucleotide will be varied according to the particular formulation, the mode of application, age, body weight and sex of the patient, diet, time of administration, condition of the patient, drug combinations, reaction sensitivities and severity of the disease. It is understood that the ordinary skilled physician will readily be able to determine and prescribe a correct dosage of this pharmaceutical compositions.

The administration mode of the pharmaceutical composition includes oral and parenteral such as subcutaneous, intradermal, intramuscular, intravenous, intrabursa, intrasternal, intrathecal and intraperitoneal injections.

In further aspect of this disclosure, there is provided a method of screening for an agent which inhibits the formation of a heterodimer between the AIMP2-DX2 protein of claim 1 and the AIMP2 protein, comprising the steps of: (a) contacting a test substance to a composition which comprises the AIMP2-DX2 protein and the AIMP2 protein; and (b) determining whether the test substance inhibits the heterodimer formation between the AIMP2-DX2 protein and the AIMP2 protein, wherein the test substance to inhibit the heterodimer formation between the AIMP2-DX2 protein and the AIMP2 protein is evaluated as an anticancer agent.

The formation of the heterodimer between the AIMP2-DX2 protein and AIMP2 protein is associated with cancer as demonstrated in Examples described hereunder. Therefore, a substance capable of inhibiting the heterodimer formation is evaluated as a candidate for anticancer agent.

According to a preferred embodiment, the instant method is performed by a yeast-two-hybrid assay and in vitro pull-down assay.

Where the present method is carried out by yeast-two-hybrid assay format, the composition comprising the AIMP2-DX2 protein and the AIMP2 protein is a cell harboring the respective gene.

In a yeast two-hybrid assay, the AIMP2-DX2 protein and AIMP2 protein can be used as either "bait" or "prey" (see, e.g., U.S. Pat. No. 5,283,317; Zervos et al., Cell 72, 223-232 (1993); Madura et al., J. Biol. Chem. 268, 12046-12054 (1993); Bartel et al., BioTechniques 14, 920-924 (1993); Iwabuchi et al., Oncogene 8, 1693-1696 (1993); and Brent WO 94/10300), to identify substances which inhibits the interaction of AIMP2-DX2 with AIMP2 to form a heterodimer. The two-hybrid system is based on the modular nature of most transcription factors, which consist of separable DNA-binding and activation domains. Briefly, the assay utilizes two different DNA constructs. For example, in one construct, polynucleotide encoding the AIMP2-DX2 protein can be fused to a polynucleotide encoding the DNA binding domain of a known transcription factor (e.g. Lex). In the other construct a DNA sequence that encodes the AIMP2 protein can be fused to a polynucleotide that codes for the activation domain of the known transcription factor (e.g. B42).

If the test substance treated to cells expressing the two-hybrid system is able to inhibit the interaction between the AIMP2-DX2 protein and AIMP2 protein, the DNA-binding and activation domains of the transcription factor are not brought into close proximity. This proximity allows transcription of a reporter gene (e.g. lac Z), which is operably linked to a transcriptional regulatory site responsive to the transcription factor. Expression of the reporter gene can be easily detected.

In an in vitro pull-down assay format, the AIMP2-DX2 gene and AIMP2 gene can be used as either bait or prey. For example, in one construct for bait, the AIMP2 protein is fused to a protein that allows the AIMP2 protein to be bound to a solid support. For example, glutathione-S-transferase (GST) fusion proteins can be adsorbed onto glutathione Sepharose beads or glutathione derivatized microtiter plates. In the other construct for prey, the AIMP2-DX2 protein is synthesized by in vitro translation system (e.g., reticulocyte lysate) using .sup.35S. The radioactive AIMP2-DX2 protein is added to the GST-AIMP2 protein bound to glutathione Sepharose beads together with the addition of the test substance. The reaction mixture is washed and the proteins bound to the Sepharose beads are eluted, followed by electrophoresis.

If the test substance added to the reaction mixture is able to inhibit the interaction between the AIMP2-DX2 protein and AIMP2 protein, the electrophoresis result shows no band.

In still further aspect of this disclosure, there is provided a method of screening for an agent which inhibits the expression of the AIMP2-DX2 gene, comprising the steps of: (a) contacting a test substance to cells which express the AIMP2-DX2 gene; and (b) determining whether the test substance inhibits the expression of the AIMP2-DX2 gene, wherein the test substance to inhibit the expression of the AIMP2-DX2 gene is evaluated as an anticancer agent.

In the present method, the expression of the AIMP2-DX2 gene is assessed at mRNA or protein level. Where the present method is carried out to detect the AIMP2-DX2 mRNA expressed, it is preferably performed by RT-PCR using AIMP2-DX2 specific primers described hereinabove. Where the present method is carried out to detect the AIMP2-DX2 protein expressed, it is preferably performed by a variety of immunoassay processes using AIMP2-DX2 specific antibodies as described above.

The following specific examples are merely for illustrating various exemplary embodiments and are not intended to limit the scope of any exemplary embodiment.

EXAMPLES

Methods
Cell Culture, Chemicals and Cell Cycle Measurement

Cells were maintained in RPMI-1640 containing 10% FBS. Mouse embryonic fibroblasts (MEFs) were isolated from 12.5-14.5 day embryos and cultivated in DMEM (Dulbecco's Modified Eagle Medium) containing 20% FBS. To evaluate the effect of TGF-β on cell cycle, cells were incubated with 2 ng/ml TGF-β in serum-free or 1% FBS-containing medium for 24 hr and harvested for FACS analysis. Cell proliferation was also determined by [$^3$H] thymidine incorporation. Cells were incubated in serum-free medium with or without TGF-β for 20 hr, and then in the presence of 1 μci/ml of [$^3$H] thymidine for 4 hr. The incorporated thymidine was quantified by liquid scintillation counting as previously described (Kim, M. J. et al., Nat. Genet. 34, 330-336 (2003)). TGF-β was purchased from R&D system, and anti-Smad2 and anti-Smad4 antibodies from Santa Cruz.

Normal lung cell line, WI-26, was purchased from Korea Cell Line Bank (KCLB) and NL-20 was a kind gift from Dr. M.-H. Cho (Seoul National University). Lung carcinoma cell lines A549, NCI-H460 were obtained from ATCC, H322 and H157 from KCLB. The siRNAs targeting AIMP2-F and -DX2 were designed by Invitrogen as previously described. The shRNA against DX2 was cloned to IMG-700 vector by SalI and XbaI (IMGENEX).

Production of Monoclonal Antibody Against AIMP2-DX2

The monoclonal antibodies were produced by a known method (Kennettm McKearn, and Bechtol (eds.), Monoclonal Antibodies, Hybridomas; A New Dimension in Biological Analyses, Plenum Press, 1980). The monoclonal antibodies were produced by immunizing an animal with the AIMP2-DX2 protein as an immunogen, fusing the splenocytes of the immunized animal with myeloma cell, P3X63Ag8.653, (ATCC CRL-1580, USA) to produce a hybridomas, screening a hybridoma that selectively recognizes the AIMP2-DX2 protein, culturing the screened hybridoma, and isolating antibodies from the hybridoma culture. And the selected hybridoma was injected into abdominal cavity of mice, and after a given period of time, antibodies were isolated from the collected ascites of the mice. The immunoglobulin isotype of the isolated antibody (clone number 324) was determined using Isotyping kit (Zymed Labomouseories Inc. USA).

Immunoblotting and Immunoprecipitation

Cells were treated with TGF-β for the indicated times and proteins were extracted with protease-containing RIPA buffer (1% Nonidet P-40, 0.5% sodium deoxycholate, 0.1% SDS), separated by 10-12% SDS-PAGE, and immunoblotted with the specific antibodies using ECL system (Santa cruz biotech). For immunoprecipitation, the cell lysates were cleared by pre-incubation with IgG (Pierce) and agarose-conjugated protein A (Invitrogen). After centrifugation, the supernatants were incubated with the specific antibody, and agarose-conjugated protein A for 2 hr. After washing with ice-cold PBS twice and RIPA once, the bound proteins were precipitated with the specific antibody, eluted and subjected to Western blot analysis.

RT-PCR

Figure 8A:
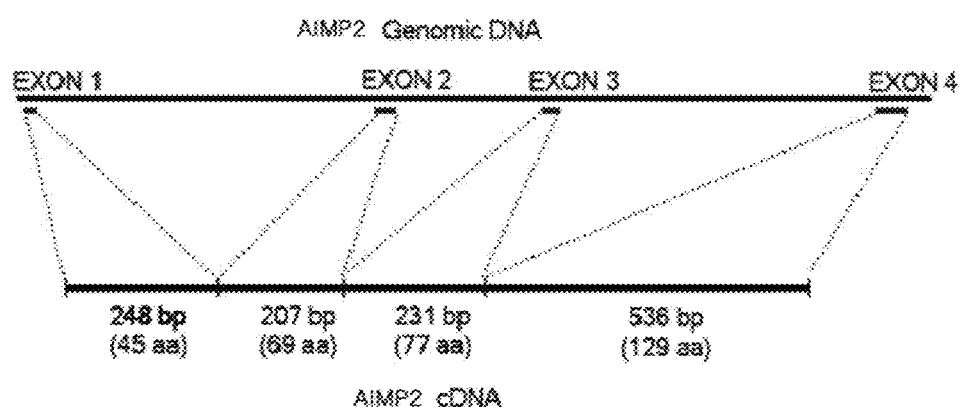
FIGS. 8a and 8b show the exon arrangement of human AIMP2 gene and the primer locations in AIMP2 cDNA.
Figure 8B:
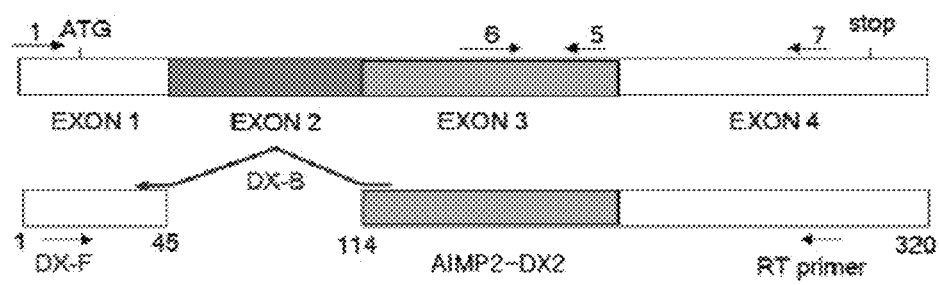

The total RNAs were isolated following the protocol of the manufacturer (Qiagen). Briefly, the freshly prepared tissues (3×3×3 mm) were chopped into small pieces, mixed with 350 μl lysis buffer and homogenized using homogenizer or syringe. After adding 350 μl of 70% ethanol, the lysates were inverted several times, loaded onto column, centrifuged at 13,000 RPM for 15 sec. After washing the column with wash buffer twice, RNAs were eluted with 40 μl RNase-free DW. For reverse transcription, 1 μg of the isolated RNA was used as a template with the AIMP2-specific primer (FIG. 8b). After the reaction, the mixture was diluted 3 fold with DW and 1 μl of its aliquot was used for 30 μl PCR reaction containing 0.5 μl dNTP (2.5 mM each), 0.5 μl of the indicated primers (each 10 μM), 1.5 μl DMSO and 0.1 μl Taq polymerase (5 U/μl).

Suppression of AIMP2-DX2 with si-RNA or sh-RNA

To suppress the expression of AIMP2-DX2, we designed the shRNA against AIMP2-DX2 with the sequence of TCGA GCTGGCCACGTGCAGGATTA CGAGTACTGG TAATCCTGCACGTGGCCAGC TTT T (SEQ.ID No.11: underlined regions are matched to the AIMP2-DX2 sequence) and cloned it into 16 IMT-700 vector system (Imgenex) using SalI and XbaI, followed by DNA sequencing for confirming the cloned sequence. H322 cells (ATCC, human lung epithelial carcinoma) were transfected with 2 μg of si-AIMP2-DX2 expression vector. Specifically, following 3-hr incubation with DNA-liposome complex in 1 ml serum-free media, H322 cells were treated with 1 ml RPMI-1640 containing 20% FBS. Then, cells were incubated in serum-free medium with or without TGF-β for 20 hr.

We also designed shRNA against AIMP2-DX2 (SEQ ID NO:26): TCGAGCTGGCCACGTGCAGGATTACGAGTACTG-GTAATCCTGCACGTG GCCAGCTTTT, underlined regions are matched to the DX2 sequence) and (SEQ ID NO:155): TCGAGCGGGCCACGTGCAGGACTATTCAAGAGA-TAGTCCTGCACGTGG CCCGC TTTT, underlined regions are matched to the DX2 sequence), and cloned into IMT-700 vector system (Imgenex) using SalI and XbaI. The plasmid was then transfected into the indicated cells.

And we also designed duplex siRNA of AIMP2-F (Invitrogen) with the sense sequence of AGUCUAACCU GUCU-CUGCAA GCUCU (SEQ ID No:25). And we also designed duplex siRNA of AIMP2-DX2 (Invitrogen & Samchully) with the sense sequence of Table 1 below. The indicated cells were transfected with a mixture of the duplex siRNA and lipofectamin 2000 (invitrogen)(1:1 (volume:volume)). After 48 hrs incubation, the transfected cell was subjected to lysis by PBS buffer (containing 0.1% SDS and 1% tritonX 100) and western blotting with AIMP2-DX2 monoclonal antibody.

TABLE 1

| Lane No. | Sequence | SEQ ID NO |
|---|---|---|
| 1 | CAC GUG CAG GAU UAC GGG GCG CUG A | SEQ ID NO: 115 |
| 2 | CUG GCC ACG UGC AGG AUU A | SEQ ID NO: 27 |
| 3 | GCC ACG UGC AGG AUU ACG G | SEQ ID NO: 30 |
| 4 | CCA CGU GCA GGA UUA CGG G | SEQ ID NO: 31 |
| 5 | CGU GCA GGA UUA CGG GGC G | SEQ ID NO: 34 |
| 6 | ACG UGC AGG AUU ACG GGG C | SEQ ID NO: 33 |
| 7 | CGU GCA GGA UUA CGG GGC GCU GAA A | SEQ ID NO: 117 |
| 8 | ACG UGC AGG AUU ACG GGG CGC UGA A | SEQ ID NO: 116 |

Yeast Two-Hybrid Analysis

The cDNAs encoding human AIMP2 and Smad2 (and its deletion fragments) were obtained by PCR using specific primers. The PCR products of Smad2 and AIMP2 were digested with EcoRI and XhoI, and ligated into the same sites of pEG202 (LexA) and pJG4-5 (B42), respectively (Gyuris, J et al., a human G1 and S phase protein phosphatase that associates with Cdk2. Cell 75, 791-803 (1993)). The interactions between Lex-Smad2 fragments and B42-AIMP2 were analyzed for their ability to grow on yeast medium containing X-gal as previously described (Rho, S. B. et al., Proc Natl Acad Sci USA 96, 4488-93. (1999)).

In Vitro Pull-Down Assay

AIMP2, AIMP2-DX2 and CDK2 were expressed as GST fusion proteins and immobilized to glutathione-Sepharose 4B (Pharmacia). The cDNA fragments encoding the AIMP2 and AIMP2-DX2 were obtained by PCR using specific primers and cloned into pET-28a vector for in vitro transcription and translation (Promega). Aliquots (10 μl) of TNT products were incubated with 5 μg of GST-AIMP2, -AIMP2-DX2 and -CDK2 immobilized on the beads in 100

μl of PBS containing 0.5% Triton X-100, 0.5 mM EDTA, and 0.5 mM phenylmethylsulfonyl fluoride. The beads were vigorously washed with the binding buffer, and the bound proteins were eluted, resolved by SDS-PAGE, and determined by autoradiography.

Construction of Cells Stably Generating AIMP2-DX2

The wild type MEFs were transfected with pcDNA-AIMP2-DX2 or pcDNA (Invitrogen) itself and the transfectants were selected in DMEM medium containing 400 μg/ml G418. After removing the untransfected cells, the transfectants were cultured in the normal medium without G418 for 3 days, fixed with 2% PFA and stained with Giemsa.

Immunostaining and Histological Analysis

The frozen tissue slides were fixed with 2% paraformaldehyde and washed with ice cold PBS. After blocking and permeablization with PBS containing 0.2% Triton X-100 (PBST) and 1% BSA, the slides were incubated with anti-AIMP2 antibody for 2 hr. After washing with PBS, they were also incubated with anti-rabbit goat IgG-FITC (Pierce) and propidium iodide (50 μg/ml, Sigma) for 1 hr, washed with PBS, mounted, and observed under a confocal microscopy (μ Radiance, Bio-Rad).

Construction of AIMP2-DX2 Expression Vector

Figure 12:
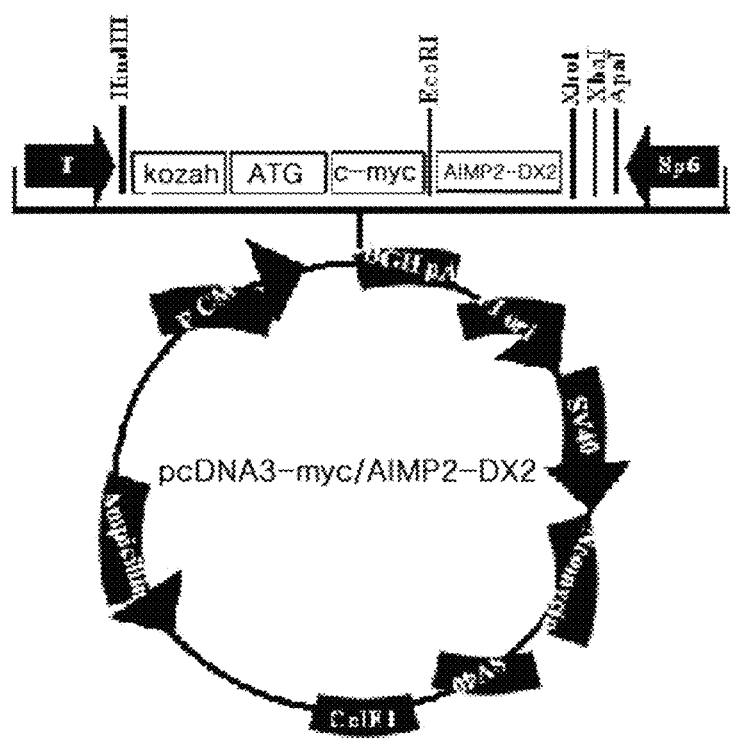
FIG. 12 shows the expression vector carrying the AIMP2-DX2 gene.

To construct the AIMP2-DX2 expressing vector, cDNA of AIMP2-DX2 was cloned into pcDNA3.1-myc. First, AIMP2-DX2 from H322 cDNA was amplified using primers with linker for EcoRI and XhoI and cloned into pcDNA3.1-myc (Invitrogen) using EcoRI and XhoI. The pcDNA3.1-myc/AIMP2-DX2 vector to express AIMP2DX (FIG. 12) was introduced into *E. coli* DH5α, which was deposited on Oct. 25, 2004 in the International Depository Authority, the Korean Collection for Type Cultures (KCTC) and was given accession number KCTC 10710BP. In the RECEIP IN THE CASE OF AN ORIGINAL DEPOSIT attached, while the identification reference read as *Escherichia coli* DH5@/p38DX2, it should be noted that p38DX2 is newly designated herein as AIMP2-DX2.

Lung Cancer Formation

32 AIMP2$^{+/-}$ mice (19 male and 13 female mice) and 25 AIMP2$^{+/+}$ mice (14 male and 11 female mice) were used for experiment. We induced lung tumor through the intraperitoneal injection of chemical carcinogen, benzo-(α)-pyrene (BP, 100 mg/kg, Sigma) into AIMP2$^{+/+}$ and AIMP2$^{+/-}$ mice, and monitored the tumor formation in lung. As a control group, 3 AIMP2$^{+/+}$ (2 male and 1 female) and 5 AIMP2$^{+/-}$ mice (4 male and 1 female) were injected with bical solution (10% DMSO and 35% PEG 40 in saline). The mice treated were sacrificed at the indicated time and their lung tissues were fixed in formaldehyde and undergone H&E staining as described in Kim, M. J. et al., Nat. Genet. 34:330-336 (2003), followed by the observation under a microscope.

In Situ Tissue Assay

The formalin fixed lung tissues were embedded with paraffin according to the standard procedure. The 4 μm tissue sections were stained with hematoxylin and eosin, and the tumor regions were analyzed using 1 mm cross stripes. To detect apoptosis in tissue, Apoptag kit (Chemicon) was used following manufacturer's instruction. Briefly, after deparaffinizing tissue sections, they were digested by proteinase K, incubated in the equilibration buffer, then with TdT enzyme, and followed by stop/wash buffer. After 50 μl of anti-digoxigenin-fluorescein was added to the tissue slides, the mounting solution containing 0.5 μg/ml propidium iodine was covered.

Quantitative RT-PCR

The expression of AIMP2-DX2 and -F were analyzed by quantitative real time RT-PCR. Fourteen normal lung samples and sixteen patients with lung adenocarcinoma were retrospectively identified from the surgical pathology files of the Department of Pathology at Samsung Medical Center and their archival formalin-fixed paraffin-embedded (FFPE) tissues were obtained. All the samples were collected anonymously according to Institutional Review Board guidelines. All patients had undergone a surgical operation and had received neither chemotherapy nor radiotherapy before surgical resection. For total RNA extraction from FFPE tissues, each tissue section was stained with hematoxylin and cancer regions were microdissected using laser microdissection system (ION LMD, JungWoo International, Korea). Paradise Whole Transcript RT Reagent System (Arcturus, Calif., USA) was used for RNA isolation and RT of FFPE samples. Due to the limitation of RNA amount extracted from FFPE tissues, half RNA and cDNA were used for reverse transcription and quantitative RT-PCR, respectively. PCR Primers and Taqman probes for this study are provided in Table 2. Poly-A polymerase alpha (PAPOLA) was chosen as the endogenous reference gene for qRT-PCR. All PCR reactions were performed in a Lightcycler 2.0 (Roche Applied Science) according to standard procedures. PCR efficiency for each gene was determined by measuring serial dilutions of cDNA from H322 cells and one lung adenocarcinoma FFPE sample and calculating from Lightcycler 4.0 software. The differential gene expression of normal and cancer region was analyzed by Mann-Whitney test. All statistical analyses were done using SPSS software (SPSS, Chicago, Ill.). Mean differences were considered significant at P<0.05. For semi-quantitative RT-PCR analysis, total RNAs were isolated following the protocol of the manufacturer (Qiagen). Briefly, the freshly prepared tissues (3×3×3 mm) were chopped into small pieces, mixed with 350 μl lysis buffer, homogenized using homogenizer or syringe. After adding 350 μl of 70% ethanol, the lysates were inverted several times, loaded onto column, centrifuged at 13,000 RPM for 15 sec. After washing the column with wash buffer twice, RNAs were eluted with 40 id RNase-free DW. For reverse transcription, 1 μg of the isolated RNA was used as the template with the AIMP2-specific primer. After the reaction, the mixture was diluted 3 fold with DW and 1 μl was used for 30 μl PCR reaction containing 0.5 dNTP (2.5 mM each), 0.5 μl of the indicated primers (each 10 pM), 1.5 μl DMSO and 0.1 μl Taq polymerase (5 U/μl).

Sequences of the quantitative RT-PCR primers and Taqman probes used for clinical specimen analysis. *PCR efficiency for each gene was determined by using serial dilution of the cDNAs obtained from lung adenocarcinoma FFPE tissues. Calculation of the efficiency was achieved using Roche Light Cycler software 4.0.

TABLE 2

| Gene | Probe | Primer | Amplicon size (bp) | PCR efficiency (dilution)* |
|---|---|---|---|---|
| AIMP2-F | FAM-cattggtggttaaagtcgtgggctcatc-BBQ (SEQ ID NO: 157) | Forward: ctccaagatgattcaaacaccagat (SEQ ID NO: 19) | 121 | 1.94 |

TABLE 2-continued

| Gene | Probe | Primer | Amplicon size (bp) | PCR efficiency (dilution)* |
|---|---|---|---|---|
| | | Reverse: ccgtaatccttccca agcac (SEQ ID NO: 20) | | |
| AIMP2-DX2 | FAM-acatcgtgatcaacgc aaacccg-BBQ (SEQ ID NO: 158) | Forward: gccacgtgcaggatt acg (SEQ ID NO: 21) Reverse: tgcaccgtggacagg acc (SEQ ID NO: 22) | 125 | 2.07 |
| PAPOLA | DYXL-aggcgttgttttctg ttggtgcac-BBQ (SEQ ID NO: 159) | Forward: aaactttttgaagct ccaaacttctt (SEQ ID NO: 23) Reverse: caccaagcccaccca ttc (SEQ ID NO: 24) | 135 | 1.94 |

Anchorage-Independent Colony Forming Assay

AIMP2-F, DX2 and pCDNA3 empty vector were transfected into 12.5 day mouse embryonic fibroblasts. The cell lines stably expressing each of the transfected plasmid were established by G418 selection. For soft agar colony assays, the cells were diluted into 0.3% agar in DMEM containing 10% FBS and seeded in triplicate onto 0.6% agar containing culture medium. 200 cells were seeded on each well in 12-well plate. The colonies were fed in every 3 to 4 days and evaluated after 5 weeks. To evaluate the correlation between the expression level of AIMP2-DX2 and colony formation, WI-26 cells (Korean Cell Line Bank) were treated with 0.1 μM Benzo[α]pyrene diolexpoxide (BPDE, NCI Chemical Repository) once a three days for 4 weeks and the surviving colonies were observed after 2 weeks from the chemical treatment. The 20 separate colonies were randomly selected to establish the cell lines.

In Vivo Tumor Formation

For xenograft experiment, NCI-H460 lung cancer cells ($10^8$ cells) stably expressing si-control or -AIMP2-DX2 were suspended in 0.9% saline 200 μl and subcutaneously injected into 6 week old female nude mouse. The tumor volumes were monitored three times a week. The volume was calculated by (length×width×height)/2. For chemical-induced lung cancer formation, benzo[a]pyrene (100 mg/kg, Sigma) was intraperitoneally injected into 6 weeks old outbred C57BL/6 mice, once a week two times. Benzo[a]pyrene was dissolved in 0.9% saline containing 35% PEG400 and 10% DMSO. To check tumor formation, the mice were randomly sacrificed at time interval from 6 weeks after injection. To determine survival rate and PET imaging, butylhydroxyltoluene (200 mg/kg, DukSan, Korea) was intraperitoneally injected into the mice four times in a week interval from 1 week after the last benzo[a]pyrene administration.

Gene Delivery

Inhalation therapy was examined as previously described (Kim, H. W., et al., Cancer Res. 64, 7971-7976 (2004)). Briefly, DNA vector was mixed with glucosylated polyethyleneimine (G-PEI) at 1.64:1 weight ratio. After 1 week from last chemical injection, the DNA mixture was delivered into lung through intranasal pathway using the humid vacuum chamber in which the DNA mixture was vaporized. The DNA vapor was inhaled for 30 min through the nose of the mice that were fixed in the cylinder using Bio-Rad compressor as previously described (Kim, H. W., et al., Cancer Res. 64, 7971-7976 (2004)). From 6 weeks after the last injection of BP, the administration of DNA was conducted twice a week for 4 weeks and the tumor areas were measured. For the analyses of survival and micro-PET, butylhydroxyltoluene was followed once a week for four week to further boost the cancer induction from 6 week after the BP administration. Then, the DNA was administered for 8 weeks in survival test and for 12 weeks in micro-PET and CT image analyses.

Ex Vivo Xenograft Test and Intratumoral Injection

Lung cancer NCI-H460 cells were transfected with si-control and si-AIMP2-DX2. After 24 h, $2 \times 10^7$ cells in 250 μl PBS were subcutaneously injected into 6 week old female nude mice (Orient Bio, Korea). Each of the control and si-AIMP2-DX2 treated groups was further divided to two groups of 6 individuals in 17 days after injection. In one group, si-control or si-DX2 were additionally injected directly into the growing tumors three times in 3 day interval. For intratumoral injection, 40 μl Lipofectamin 2000 (Invitrogen) and 1 nmole si-RNA in 100 □l RPMI were used per 1 cm³ tumor volume. The siRNA mixtures were injected at 3 or 4 points of tumors using 31 gage needle. Tumor volumes were monitored three times a week. The experiments were terminated in 5 days after the last injection.

Image Analysis of Tumor Growth

The mice were injected with 250 μCi of [18F] fluoro-2-deoxy-D-glucose (18FDG) via tail vein. The mice were scanned for 30 min to obtain static images in 30 min after injection. We acquired Micro-PET R4 (Concorde Microsystems, Knoxville Tenn.) that uses LSO crystals and allows timing windows of 6 nano second. The micro-PET data were reconstructed using ordered subsets expectation maximization (OSEM) algorithm with 4 iterations. The CT scans were performed using a GE Discovery LS PET/CT scanner. The CT imaging was performed with 1.2115 mm axial sampling. The CT and micro-PET images were co-registered using the fiducial markers and manually identified in both data sets to perform a point-based rigid co-registration using AMIDE (Amide's a Medical Image Data Examiner) and ASIPro (CTI Concorde Microsystems). Regions of interest (ROIs) were manually drawn over the lung region. Tracer uptake was quantified as standardized uptake values (SUVs) using the following formula:

SUV=tissue activity concentration in ROI(Bq/mL)/ injected dose(Bq)×body weight(g).

Results

Functional Importance and Working Mode of AIMP2 in TGF-β Signaling

Figure 1B:
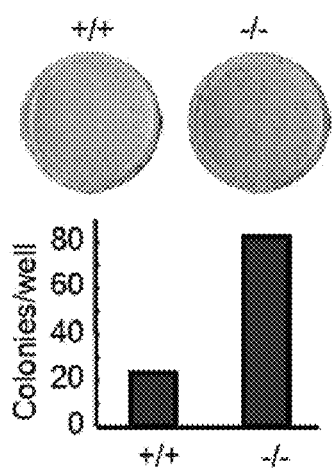
Figure 1C:
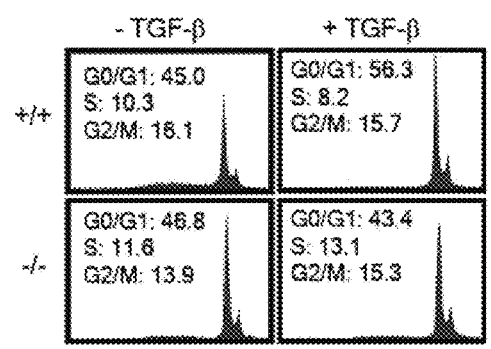
Figure 1D:
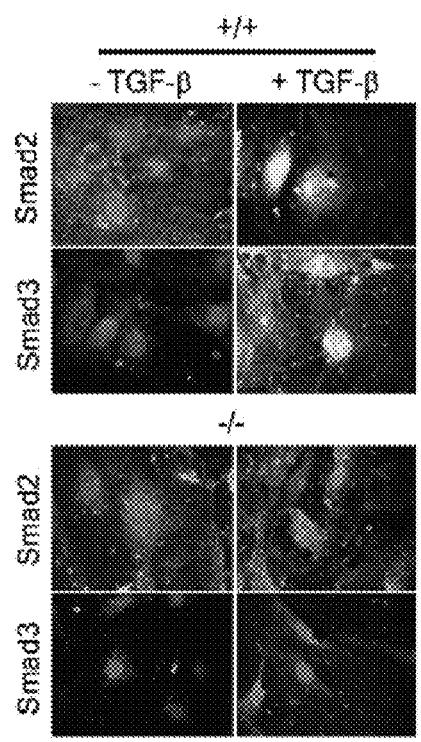

To see the importance of AIMP2 in TGF-β signaling, we compared the responses of the AIMP2$^{+/+}$ and AIMP2$^{-/-}$ MEFs to TGF-β-induced growth arrest, nuclear translocation of Smad2/3 and interaction of AIMP2 with Smad2/3. While the growth of the wild type cells was suppressed by TGF-β, the AIMP2-deficient cells did not respond to the signal as determined by thymidine incorporation, colony formation and flow cytometry (FIGS. 1a, 1b and 1c, respectively). When MEFs were treated with TGF-β, Smad2 and Smad3 were translocated to nuclei in the normal cells, but not in the AIMP2-cells (FIG. 1d). All of these results suggest the functional importance of AIMP2 in TGF-β signaling via Smad2 and Smad3.

Figure 1E:
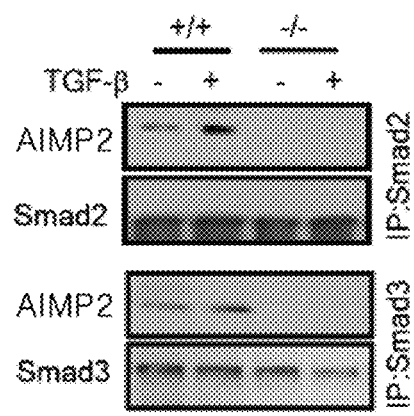
Figure 2A:
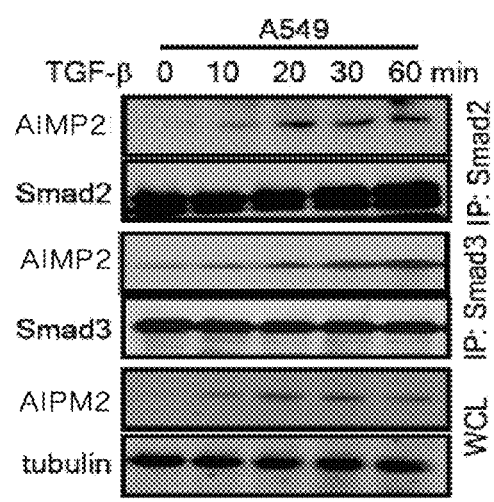
FIGS. 2a-2f represent the working mechanism of AIMP2 in TGF-β signaling.
Figure 2B:
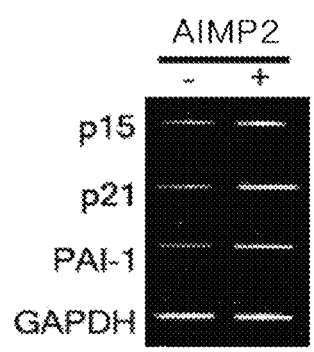
Figure 2C:
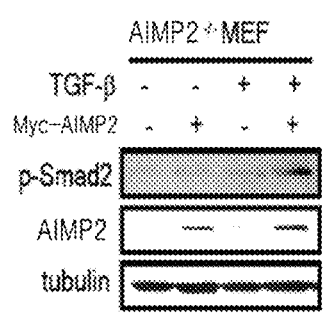
Figure 2D:
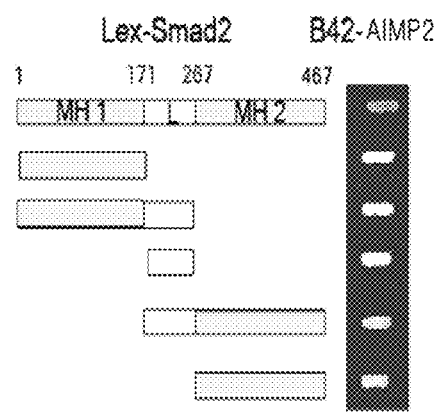
Figure 7:
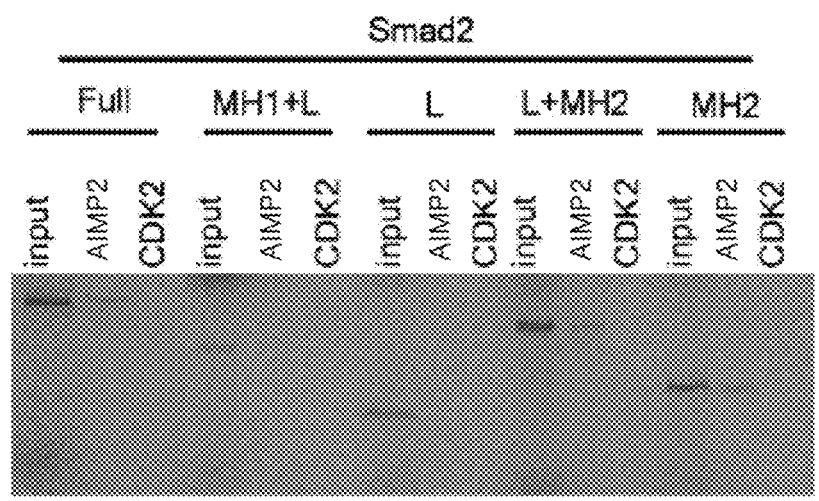
FIG. 7 represents the determination of the Smad2 domain involved in the interaction with AIMP2. We ligated the cDNAs encoding AIMP2 or CDK2 to the EcoRI and XhoI sites of pGEX4T-1 to express them in E. coli BL21 (DE3) as the GST-fusion proteins and purified them following the manufacturer's instruction. The different deletion fragments of Smad2 were synthesized by in vitro translation in the presence of [$^{35}$S] methionine using the TNT coupled translation kit (Promega). The GST fusion proteins bound to the glutathione Sepharose beads were incubated with the [$^{35}$S] methionine-labeled Smad2 fragments in the binding buffer of PBS buffer (pH 7.4) containing 0.5 mM EDTA, 0.5 mM phenylmethylsulfonylfluoride (PMSF), and 1% Triton X-100. The binding mixture was incubated overnight 4° C. with rotation and washed four times with the binding buffer containing 0.5% Triton X-100. After addition of the SDS sample buffer, the bound proteins were eluted by boiling and separated by SDS gel electrophoresis. The presence of Smad2 fragments was determined by autoradiography.

We then checked the possible interaction of AIMP2 with Smad2 and 3 by coimmunoprecipitation. AIMP2 showed the interaction with Smad2/3 that was enhanced by TGF-β (FIG. 1e). The direct interaction of AIMP2 with two R-Smads was also confirmed by yeast two hybrid and in vitro pull-down assays (FIGS. 2a-2f and 7). The amount of AIMP2 bound to Smad2/3 was increased according to the induction of AIMP2 by TGF-β (FIG. 2a). When the AIMP2 level was increased by transfection, the expression of the TGF-β target genes was enhanced, suggesting its stimulatory role in TGF-β signaling (FIG. 2b). Since AIMP2 binds to both of Smad2 and 3, we expected that it would work to these two R-Smads in a similar way and thus focused on its relationship to Smad2 in more detail. The TGF-β-dependent phosphorylation of Smad2 was suppressed in the AIMP2-deficient MEFs, but restored when AIMP2 was introduced to AIMP2$^{-/-}$ cells (FIG. 2c). We then determined the domain of Smad2 involved in the interaction with AIMP2 by yeast two hybrid (FIG. 2d) and in vitro pull-down assay (FIG. 7). The two experiments revealed that the interaction involves the MH2 domain of Smad2.

Figure 2E:
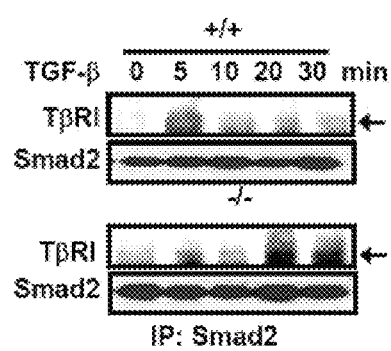
Figure 2F:
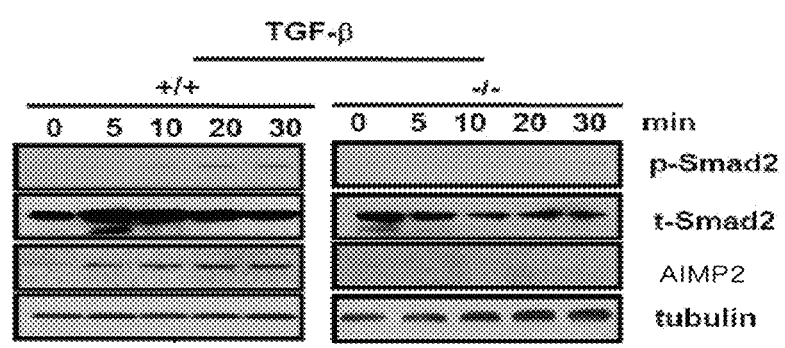

To determine the working mode of AIMP2 in TGF-β signaling, we compared the TGF-β-induced association of Smad2 with TGF-β receptor in the normal and AIMP2-deficient cells. The cells were treated with TGF-β and the association of Smad2 and the receptor was monitored by co-immunoprecipitation of type I receptor with Smad2 at time interval. While the TGF-β-induced Smad2 binding to TGF-β receptor was observed at early time point and decreased in the wild type cells, the receptor bound to Smad2 was accumulated in the late stage after TGF-β treatment in the AIMP2-deficient cells (FIG. 2e). In the TGF-β-induced phosphorylation of Smad2, the phosphorylated Smad2 was gradually increased in the wild type cells, but severely suppressed in the AIMP2$^{-/-}$ cells (FIG. 2f). These results demonstrate that AIMP2 plays a critical role in the TGF-β induced phosphorylation of R-Smads via its direct interaction with R-Smad2.

Suppression of AIMP2 and Generation of Its Deletion Variant in Cancer Cells

Figure 3A:
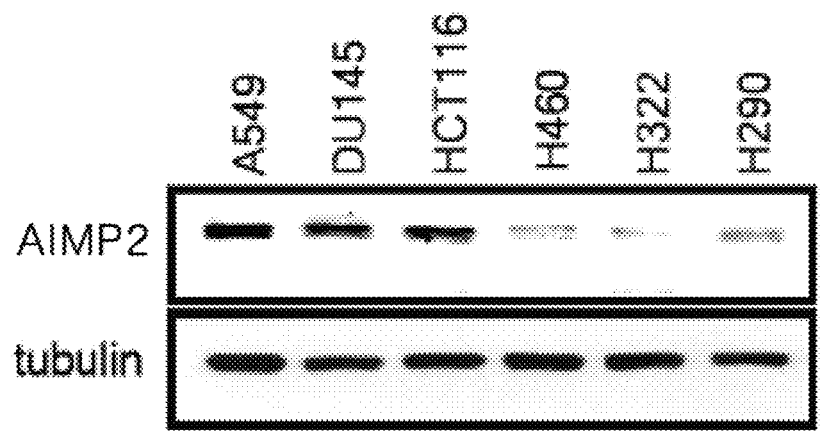
FIGS. 3a-3f represent the differential expression of AIMP2 and generation of its exon 2-deletion form. The AIMP2 levels were compared in various cancer cell lines by Western blot analysis (FIG. 3a) and flow cytometry (FIG. 3b). A549, NC1-H460, -H322, and H290 are lung cancer cell lines while DU145 and HCT116 are prostate and colon cancer cell lines, respectively.
Figure 3B:
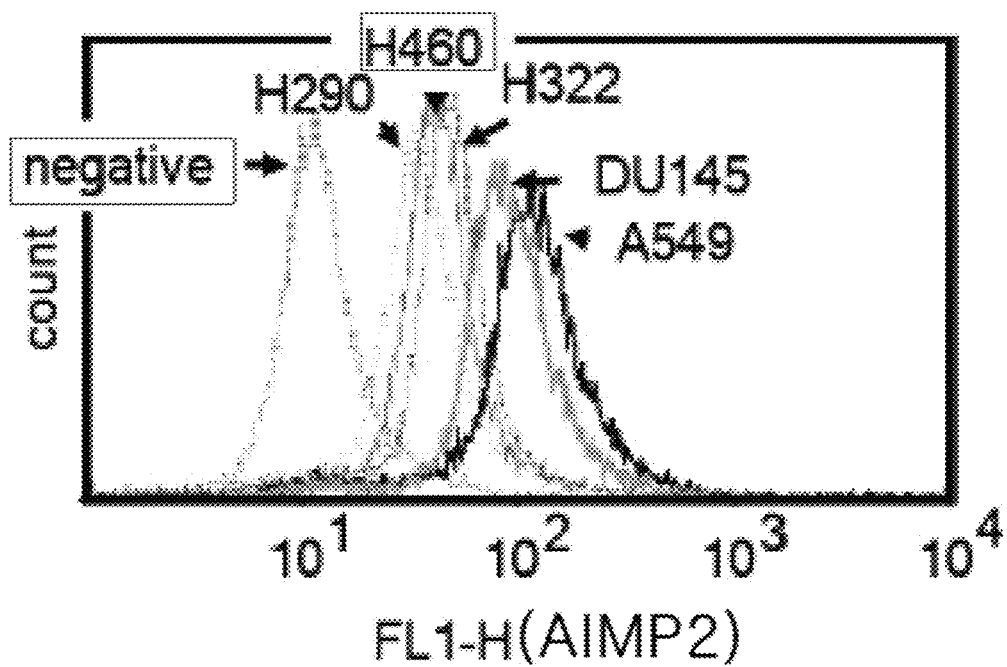
Figure 3C:
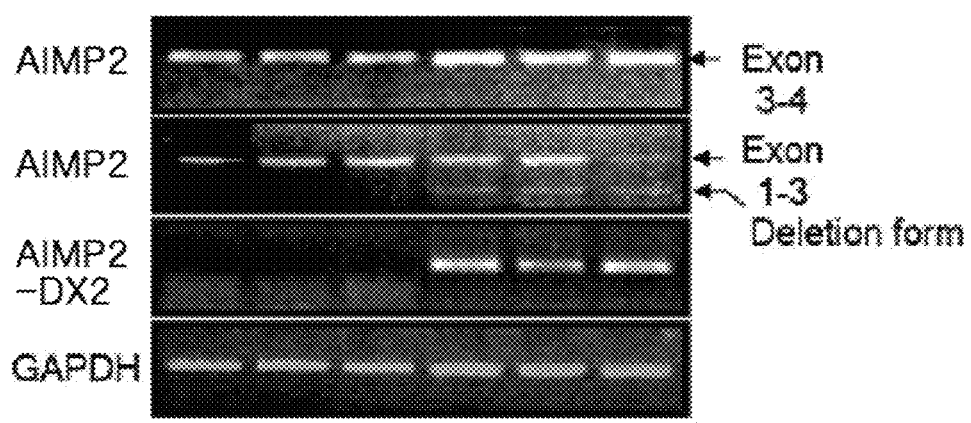

To explore the possible association of AIMP2 with cancer formation, we checked the variation of AIMP2 level in different cancer cell lines [A549 (lung epithelial carcinoma), DU145 (prostate carcinoma), HCT116 (human colorectal carcinoma), H460 (large cell lung carcinoma), H322 (lung bronchioalveolar carcinoma) and H290 (mesothelioma cancer cell line) available from ATCC]. Three of the six tested cell lines showed lower AIMP2 level in Western blot (FIG. 3a) and FACS analyses (FIG. 3b). All of the cell lines with low AIMP2 level expressed the normal level of the TGF-β type II receptor and retained its kinase activity, implying that the low AIMP2 level does not result from the mal-functionality of the receptor. To determine whether the variation of AIMP2 level resulted from the difference in transcription, we performed RT-PCR with different combinations of the AIMP2-specific primers. The AIMP2 gene consists of four exons (FIG. 8a). When the primers were used to generate AIMP2 cDNA spanning exon 3 and 4, the decrease of AIMP2 transcript was not observed in the cells showing the reduced level of AIMP2 (FIG. 3c, first row), suggesting that it does not result from lower transcription. When we used the primers generating the transcript from exon 1 to 3, we obtained not only the transcript of the expected size, but also a smaller one (FIG. 3c, second row). Sequencing analysis of this small transcript revealed that it lacks exon 2 encoding 69 aa of AIMP2 (FIG. 8b). To confirm the generation of this smaller transcript, we designed the primer (FIG. 8b, primer DX-B) targeting to the junction sequence of exon 1 and 3 that is generated by the deletion of exon 2, and conducted RT-PCR with this primer. The cell lines expressing lower AIMP2 level generated the smaller transcript (designated AIMP2-DX2, FIG. 3c, second and third rows).

Figure 3D:
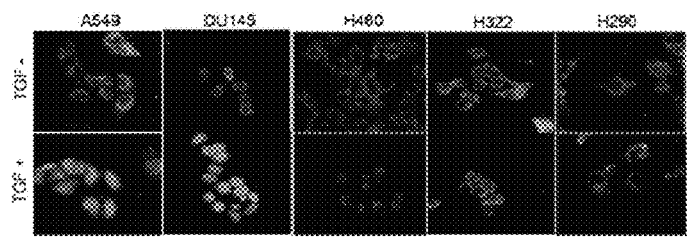
Figure 3E:
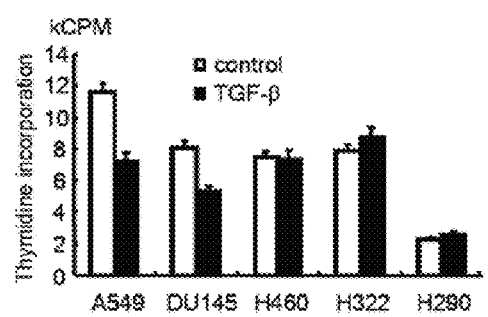
Figure 3F:
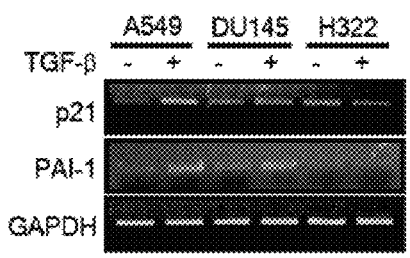
Figure 9A:
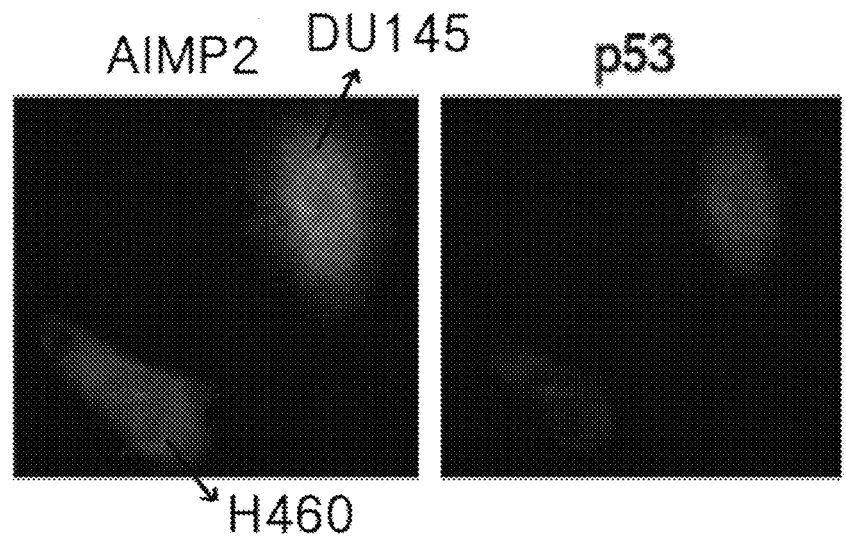
FIGS. 9a-9d demonstrate reduced expression of AIMP2, and generation of AIMP2-DX2 in cancer cell lines.
Figure 9B:
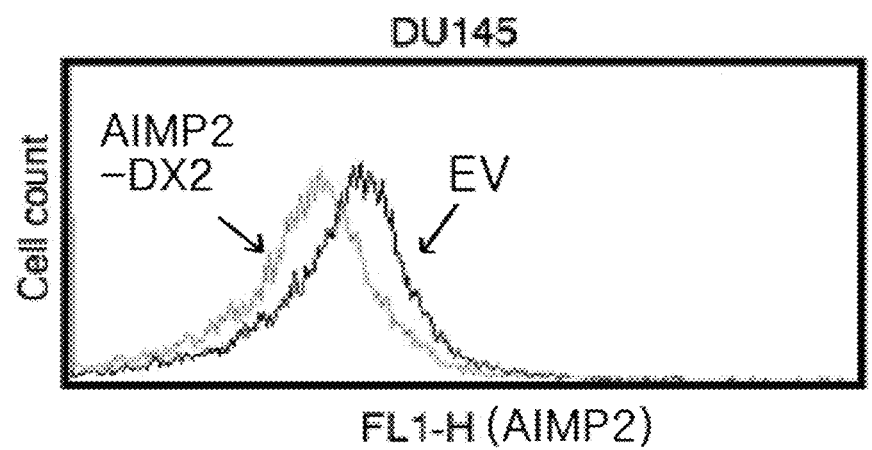
Figure 9C:
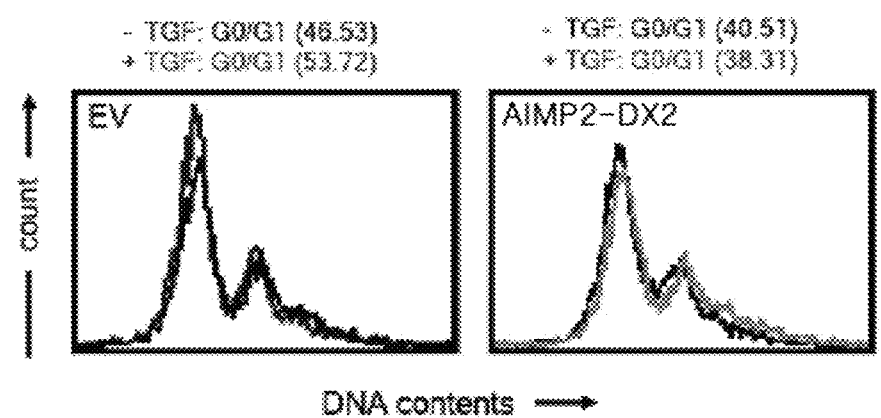
Figure 9D:
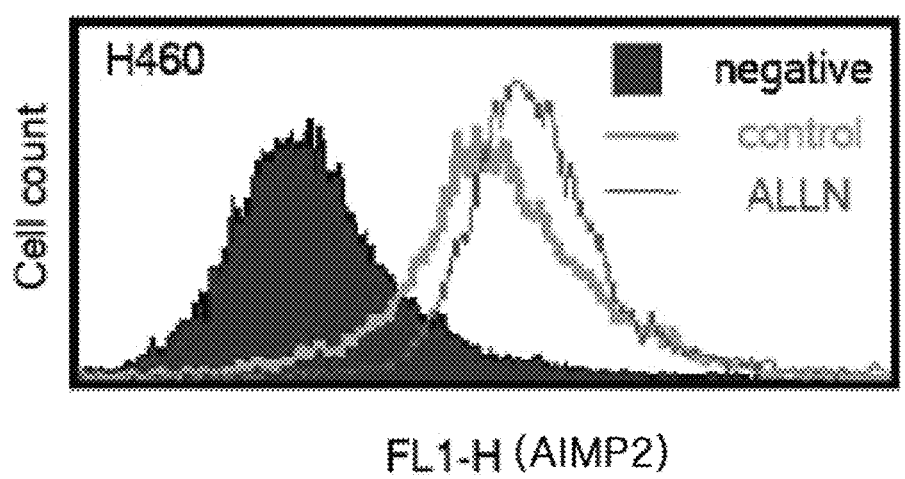

Western blot analysis with anti-AIMP2 antibody detected only the full-length AIMP2, but not AIMP2-DX2 (FIG. 2a), implying that AIMP2-DX2 may be very unstable at protein level. Immunofluorescence staining also demonstrated the lower AIMP2 level in H460, H322 and H290 (FIG. 3d). To exclude the possibility of staining artifact, we co-cultivated H460 and DU145 cells in the same plate and stained AIMP2. Again, the staining intensity of AIMP2 in H460 was much weaker than that in DU145 (FIG. 9a). In addition, the TGF-β-dependent nuclear localization of AIMP2 was not observed in the cells with low AIMP2 expression (FIG. 9d, bottom row). To address the linkage between the AIMP2 level and functionality of TGF-β, we measured growth suppression by TGF-β in these cell lines. While the growth of A549 and DU145 cells was suppressed by TGF-β, the cells with low AIMP2 level did not respond to TGF-β (FIG. 9e). This result is consistent with previous reports that A549 is sensitive whereas H460 is resistant to TGF-β signal (Osada, H. et al. Cancer Res. 61, 8331-8339 (2001); Kim, T. K. et al., Lung Cancer 31, 181-191 (2001)). In addition, the target genes were induced by TGF-β in A549 and DU145, but not in H322 and two other cell lines with low AIMP2 (FIG. 3f).

Furthermore, we tested by RT-PCR whether other cancer cell lines generates AIMP2-DX2. As a result, it was revealed that AIMP2-DX2 was detected in SaOS2 (osteosarcoma) and MCF7 (breast adenocarcinoma cell).

The Inactive Deletion Variant Forms a Complex with Functional AIMP2

Figure 4A:
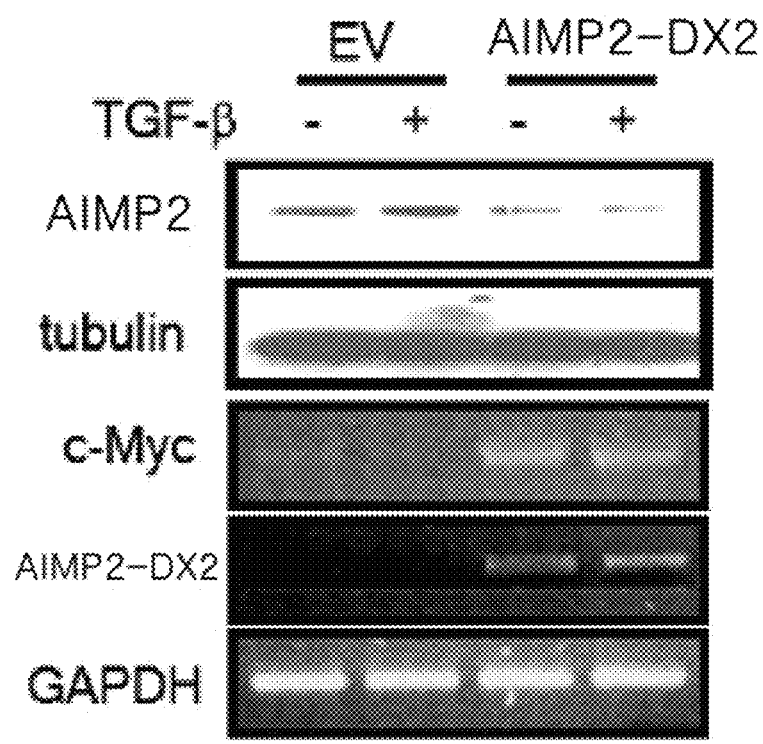
FIGS. 4a-4h demonstrate the Effect of AIMP2-DX2 on the cellular stability of AIMP2.
Figure 4B:
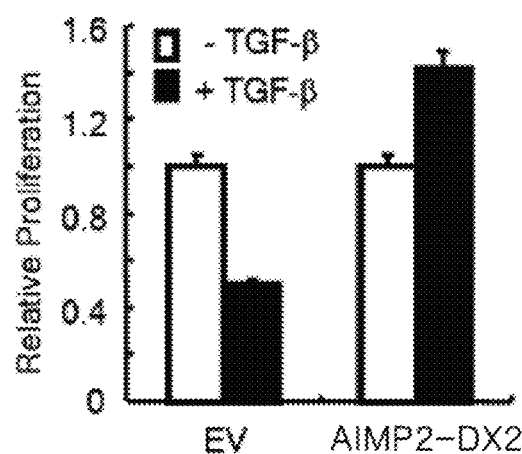
Figure 4C:
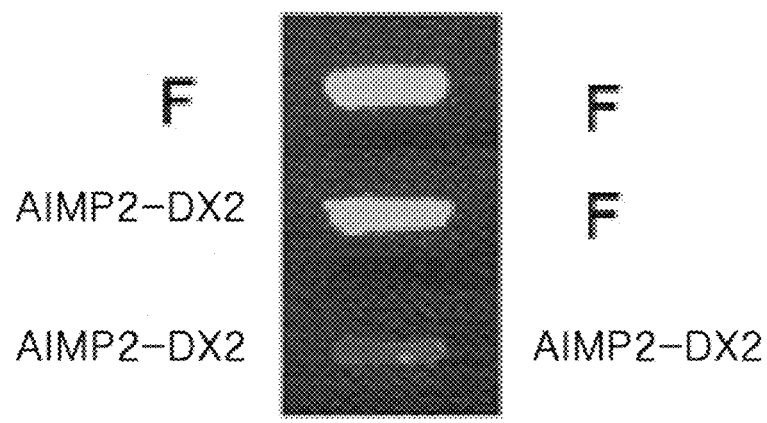
Figure 4D:
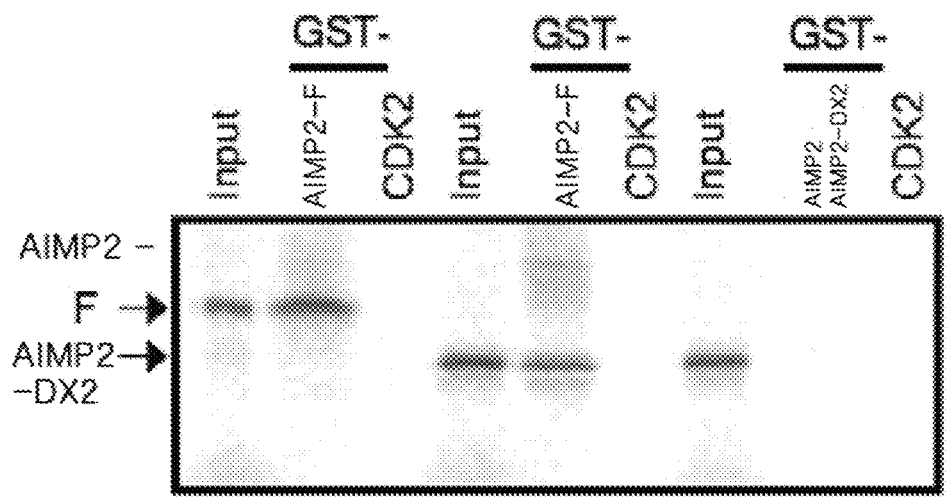
Figure 4E:
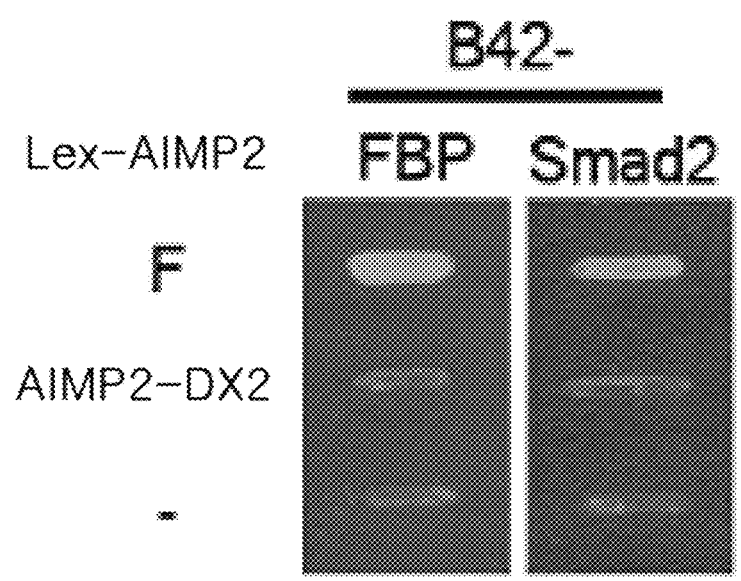

To comprehend the causal relationship of the AIMP2-DX2 generation and suppression of AIMP2, we checked the change of the AIMP2 level after transfection of AIMP2-DX2 into DU145. AIMP2 was reduced in the AIMP2-DX2-transfected cells, as demonstrated by Western blot (FIG. 4a, first row) and FACS analyses (FIG. 9b). Moreover, the expression of the AIMP2 target, c-myc, was elevated by the introduction of AIMP2-DX2 (FIG. 4a, third row). AIMP2-DX2 also relieved the growth arrest by TGF-β (FIGS. 4b and 9c). We then investigated how AIMP2-DX2 would affect the functional AIMP2 (AIMP2-F). Since AIMP2 has a potential to form a homodimer (Quevillon, S. et al., J. Mol. Biol. 285, 183-195 (1999); and Kim, J. Y. et al., Proc. Natl. Acad. Sci. USA 99, 7912-7916 (2002)), we examined whether AIMP2-DX2 would interact with AIMP2-F by yeast two hybrid assay. AIMP2-DX2 showed the interaction with AIMP2-F, but not with itself (FIG. 4c). In in vitro pull-down assay, both of radioactively synthesized AIMP2-F and AIMP2-DX2, but not AIMP2-DX2, were co-purified with GST-AIMP2-F (FIG. 4d), proving the direct interaction between AIMP2-F and AIMP2-DX2. To see whether AIMP2-DX2 is active in TGF-β signaling, we tested its interaction with Smad2 by yeast two hybrid assay. While AIMP2 interacted with Smad2 as well as FBP that is the known target of AIMP2 (Kim, M. J. et al., Nat. Genet. 34, 330-336 (2003)), AIMP2-DX2 did not bind to any of these proteins, suggesting that it would be functionally inactive (FIG. 4e).

Figure 4F:
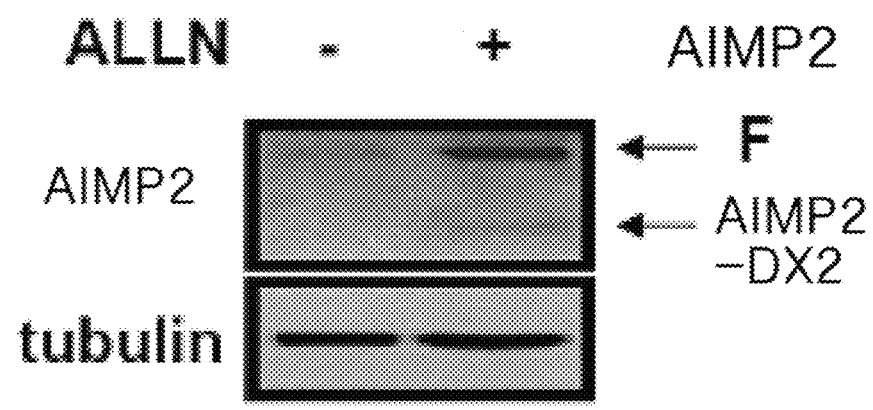
Figure 4G:
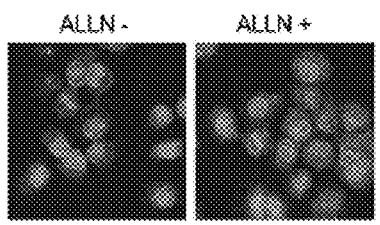
Figure 4H:
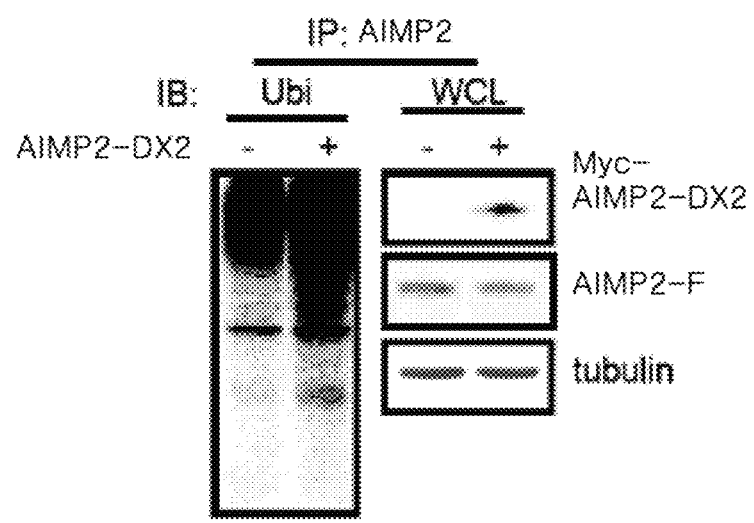

To understand how the heterodimer formation would suppress AIMP2, we checked whether the AIMP2 level is controlled by proteasome-dependent degradation process. The AIMP2-DX2-producing H322 cells were treated with the proteasome inhibitor, ALLN (Zhou, M., et al., J. Biol. Chem. 271, 24769-24775 (1996)) and tested whether the AIMP2 level is increased by the blockage of proteasome. The AIMP2 level was significantly increased by the treatment of ALLN as shown by Western blotting (FIG. 4f), immunofluorescence staining (FIG. 4 g) and flow cytometry (FIG. 9d), suggesting that its cellular level would be controlled by proteasome-mediated degradation. In addition, AIMP2-DX2 form was also detected by the inhibition of proteasome (FIG. 4f), confirming the notion that AIMP2-DX2 would be unstable due to the rapid proteasome-dependent degradation. The low intensity of AIMP2-DX2 appears to result from its lower transcription compared to the normal AIMP2, as demonstrated by RT-PCR analysis (FIG. 3c) and/or less efficient recognition by anti-AIMP2 antibody. Since AIMP2 degradation is mediated by proteasome, we tested whether its ubiquitination is promoted by AIMP2-DX2. When AIMP2 was immunoprecipitated from the control and AIMP2-DX2-transfected cells that were treated with ALLN and blotted with anti-ubiquitin antibody, higher amount of the ubiquitinated AIMP2 was observed in the AIMP2-DX2-transfected cells compared to that in control cells (FIG. 4h). Combined together, AIMP2-DX2 appears to work as a dominant negative mutant to form an inactive complex with AIMP2 that is rapidly driven to degradation process.

AIMP2-DX2 Inactivates TGF-α Signaling and Promotes Cell Growth

Figure 5A:
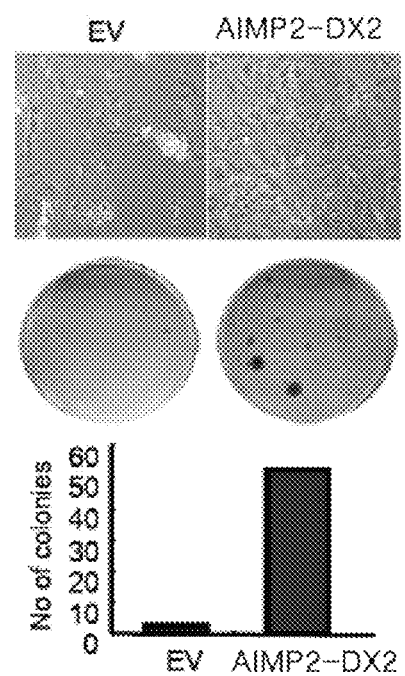
FIGS. 5a-5e represent the disruptive effect of AIMP2-DX2 on cell growth control and TGF-β signaling.
Figure 5B:
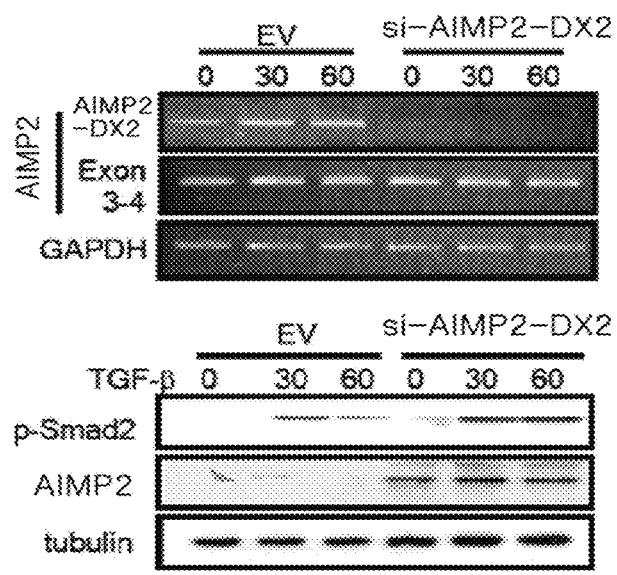
Figure 5C:
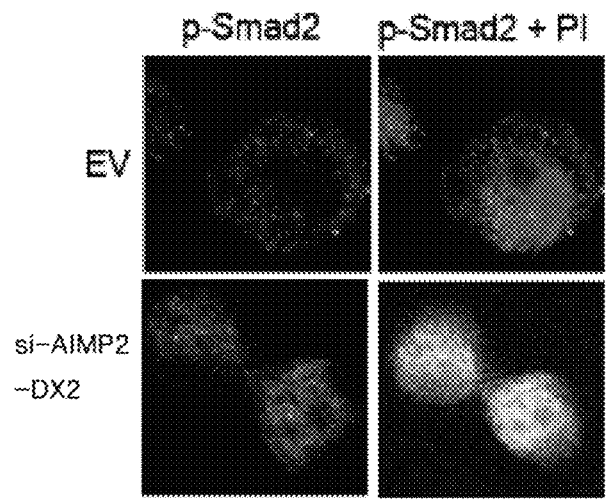
Figure 5D:
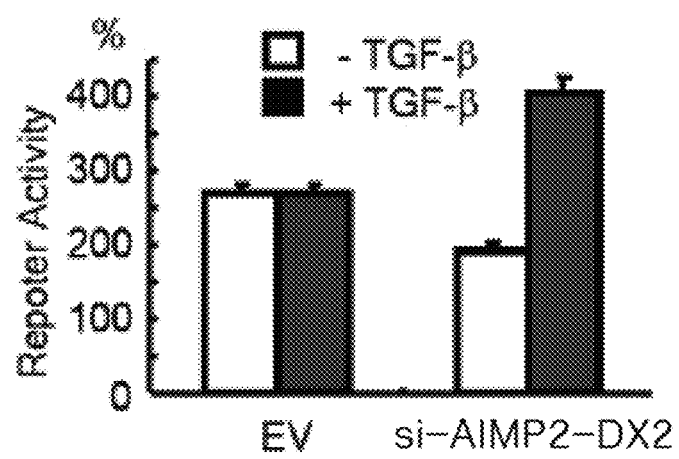
Figure 5E:
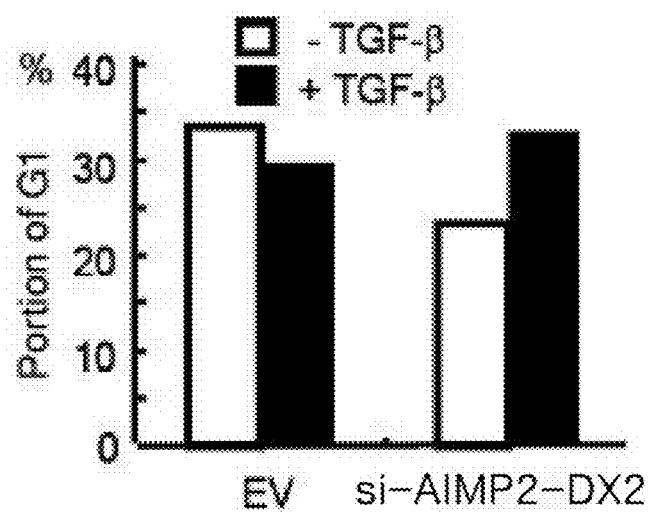

We transfected AIMP2-DX2 into MEFs and monitored its effect on cell growth by microscopic analysis and colony formation. The cell growth was significantly enhanced by the introduction of AIMP2-DX2 (FIG. 5a). We then introduced siRNA (si-AIMP2-DX2) that specifically suppresses the AIMP2-DX2 transcript and checked whether it can restore the normal level of AIMP2 and TGF-β signaling in H322 cells expressing AIMP2-DX2. si-AIMP2-DX2 ablated the AIMP2-DX2 transcript (FIG. 5b top) and resumed the normal AIMP2 level and TGF-β-induced phosphorylation of Smad2 (FIG. 5b bottom), nuclear localization of p-Smad2 (FIG. 5c), TGF-β-dependent reporter expression (FIG. 5d) and growth arrest (FIG. 5e). All of these results demonstrated the disruptive effect of AIMP2-DX2 on TGF-β signaling and cell growth control.

Association of AIMP2 Deletion Variant with Human Lung Cancer

Figure 6A:
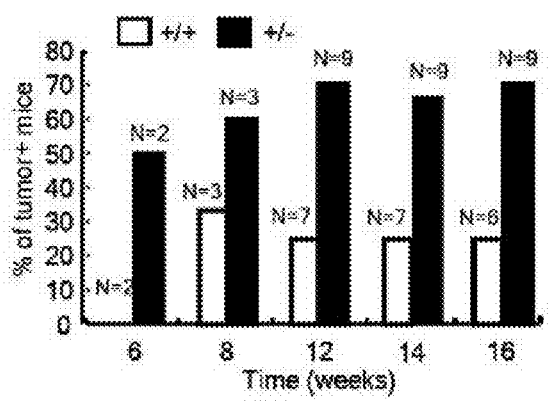
FIGS. 6a-6c represent the association of AIMP2 with lung cancer formation.
Figure 6B:
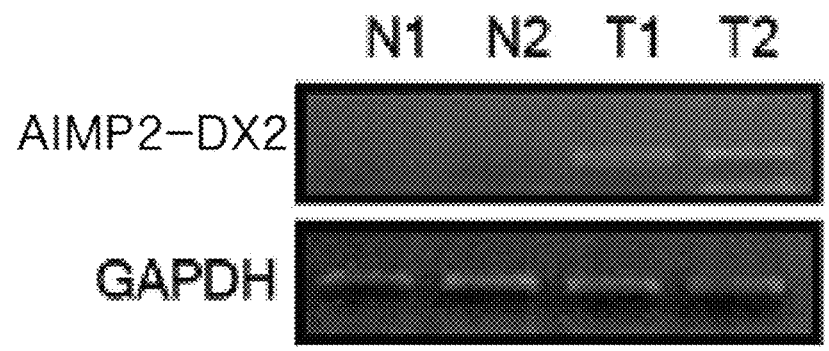
Figure 6C:
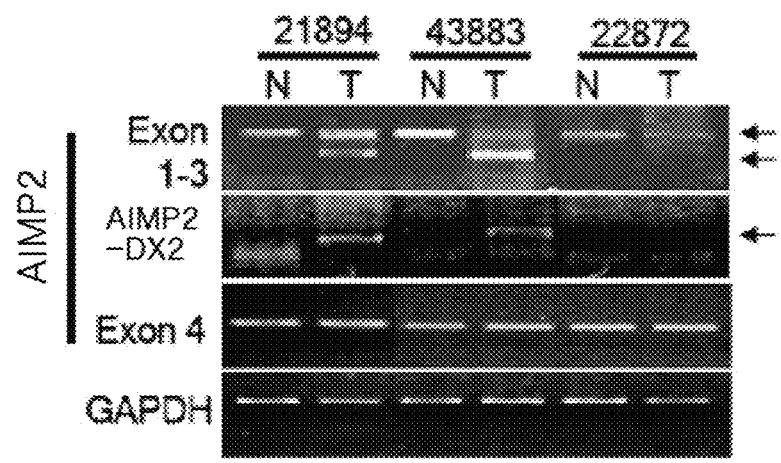
Figure 10:
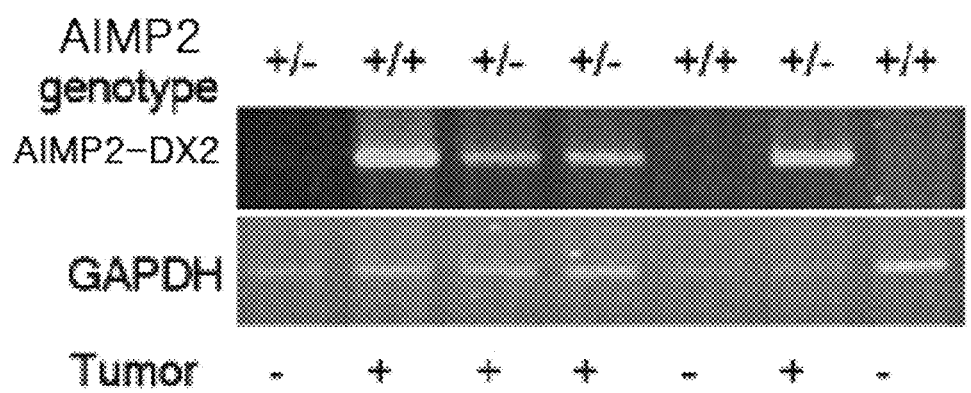
FIG. 10 shows the generation of AIMP2-DX2 and suppression of AIMP2 in lung cancer tissues. Lungs were isolated from the AIMP2$^{+/+}$ and AIMP2$^{+/-}$ mice injected with benzoypyrene, and RNAs were isolated from each lung for RT-PCR to determine the generation of AIMP2-DX2. All of the lungs generating AIMP2-DX2 showed tumor formation in lung (marked+).

Since the reduction of AIMP2 is frequently detected in different cancer cell lines (FIGS. 3a, 3b and 3d), and loss of AIMP2 leads to hyper-proliferation of lung cells (Kim, M. J. et al., Nat. Genet. 34, 330-336 (2003)), we examined the association of AIMP2 abnormality with lung cancer formation. We induced lung tumor through the intraperitoneal injection of chemical carcinogen, benzo-(α)-pyrene (B P, Wang, Y. et al., Cancer Res. 63, 4389-4395 (2003)) into $AIMP2^{+/+}$ and $AIMP2^{+/-}$ mice, and monitored the tumor formation in lung. From 6 weeks after the administration of BP, lung tumors were observed at 50-70% frequency in $AIMP2^{+/-}$ mice, and at about 30% in the wild type littermates (FIG. 6a), implying that the heterozygous mice are more susceptible to BP-induced tumorigenesis. We examined whether AIMP2-DX2 is generated in the lungs of the BP-injected mice. Three out of four lungs isolated from $AIMP2^{+/-}$ mice showed tumors, while only one developed tumors among three $AIMP2^{+/+}$ mice and all of these tumors generated AIMP2-DX2 (FIG. 10), further supporting the relevance of AIMP2-DX2 to tumor formation. Moreover, AIMP2-DX2 was generated only in tumor tissues (FIG. 6b). To exclude the possibility that the AIMP2 level and AIMP2-DX2 formation may vary depending on different individuals, we carried out RT-PCR analyses in the normal and tumor pairs isolated from the same patients. Again, the cancer-specific reduction of AIMP2 was coupled with the generation of AIMP2-DX2 (FIG. 6c). AIMP2-DX2 was not detected in one case showing the normal AIMP2 level in cancer region (FIG. 6c, patient 22872). We further examined 10 different pathologically-diagnosed lung adenocarcinoma, squamous cell carcinoma and large cell adenocarcinoma samples, and observed the cancer-specific reduction of AIMP2 and generation of AIMP2-DX2 in 8 cases (Table 3). Although AIMP2-DX2 was detected in the histologically normal regions in two cases, its occurrence was still coupled with the low level of AIMP2.

TABLE 3

The relationship between AIMP2 level and DX2 generation in different lung cancer patients

| No | Code (MLLG) | Cell type | Opdate | Recur | Sex | Age | AIMP2-F N | AIMP2-F T | AIMP2-DX2 N | AIMP2-DX2 T |
|---|---|---|---|---|---|---|---|---|---|---|
| 1 | H004 | SQC | 01-06-26 | FALSE | M | 64 | + | − | − | + |
| 2 | H008 | ADC | 01-019-26 | FALSE | M | 62 | + | − | − | + |
| 3 | H001 | ADC | 01-12-14 | FALSE | M | 68 | + | − | − | + |

TABLE 3-continued

The relationship between AIMP2 level and DX2 generation in different lung cancer patients

| No | Code (MLLG) | Cell type | Opdate | Recur | Sex | Age | AIMP2-F N | AIMP2-F T | AIMP2-DX2 N | AIMP2-DX2 T |
|---|---|---|---|---|---|---|---|---|---|---|
| 4 | H010 | SQC | 01-12-26 | FALSE | M | 56 | + | − | − | + |
| 5 | H018 | ADC | 02-04-26 | FALSE | M | 60 | − | − | + | + |
| 6 | H021 | ADC | 02-05-07 | TRUE | F | 64 | − | − | + | + |
| 7 | H024 | ADC | 02-05-17 | FALSE | F | 59 | + | − | − | + |
| 8 | H025 | SQC | 02-05-28 | FALSE | M | 73 | + | − | − | + |
| 9 | H029 | ADC | 02-06-14 | FALSE | M | 67 | + | − | − | + |
| 10 | H031 | LAC | 02-07-08 | FALSE | M | 71 | + | − | − | + |

[Positive (+) and negative (−) in the AIMP2-F column denote the immunofluorescence staining of AIMP2 in normal (N) and tumor (T) tissues determined by histological analysis. Positive and negative in AIMP2-DX2 column indicate the generation of DX2 that was determined by RT-PCR. Note for abbreviations: Recur (recurrence), SQC (squamous cell carcinoma), ADC (adenocarcinoma), LAC (large cell adenocarcinoma) and Opdate (operation date)]

Association of AIMP2 and its Deletion Variant with Human Liver Cancer

Figure 11:
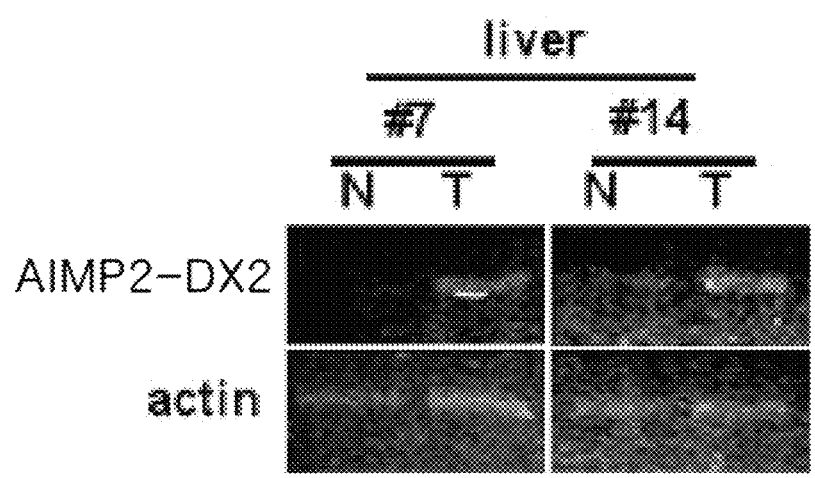
FIG. 11 represents the expression of AIMP2-DX2 and suppression of AIMP2 in liver cancer tissues. RT-PCR was performed to determine the expression of AIMP2-DX2 in liver cancer tissues.

We examined the relationship of AIMP2 or its deletion variant with human liver cancer using human tissues. The formation of AIMP2-DX2 was evaluated in normal and cancer tissue (hepatocellular carcinoma) by RT-PCR and the level of AIMP2 by immunofluorescence analyses as described previously. As a result, AIMP2-DX2 was detected in live cancer tissues (FIG. 11).

Figure 13A:
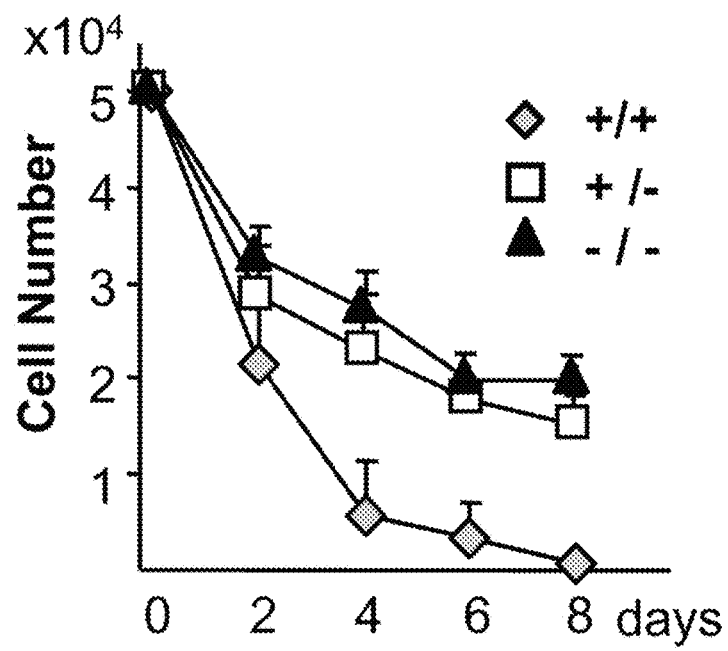
FIGS. 13a-13e show increased susceptibility of AIMP2$^{+/-}$ mice to tumorigenesis and expression of its splicing variant.
Figure 13B:
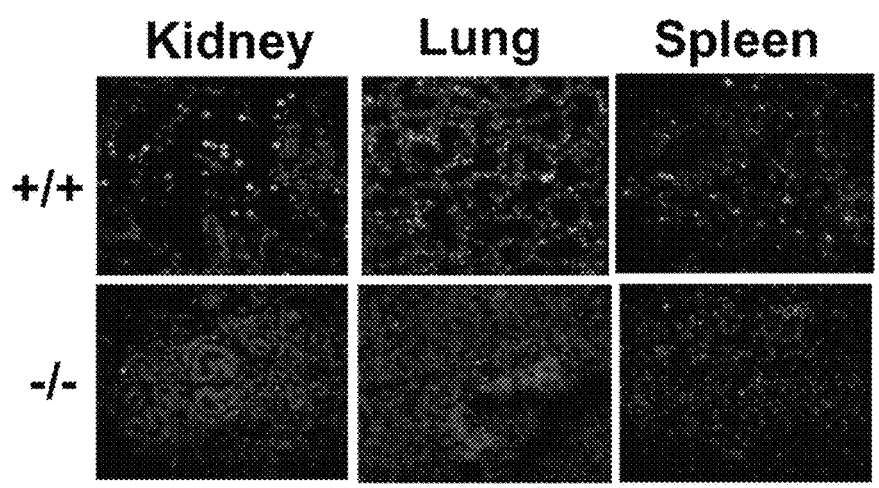
Figure 13C:
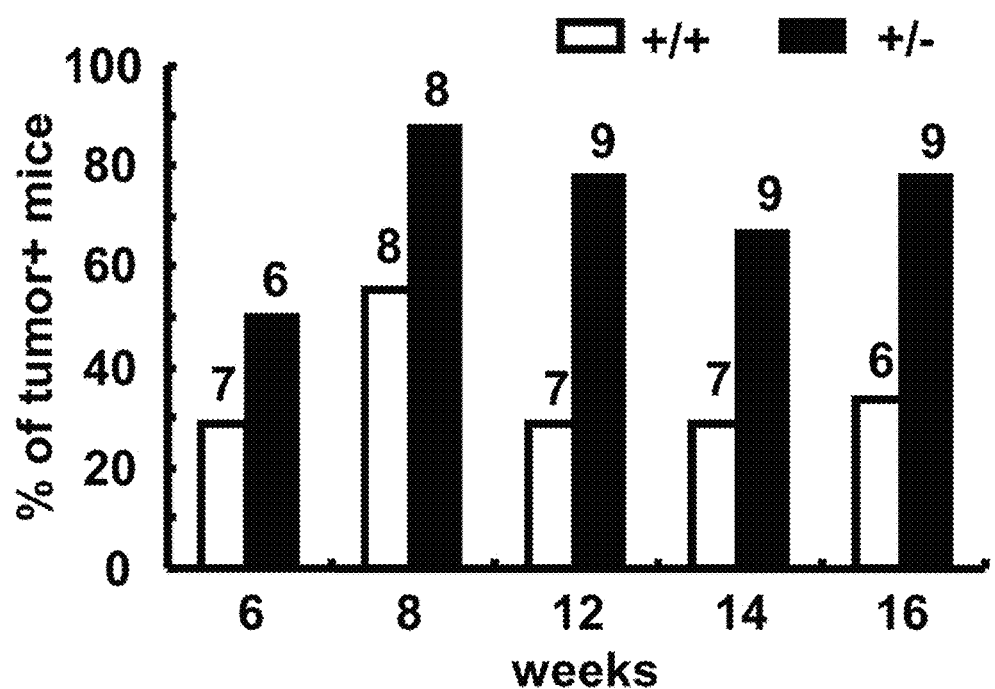
Figure 13D:
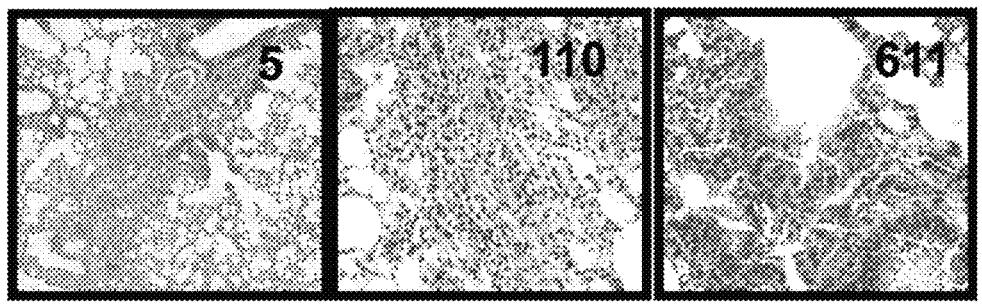

Increased Susceptibility of AIMP2$^{+/-}$ Mice to Tumorigenesis and Expression of its Splicing Variant The potential tumor suppressive activity of AIMP2 was tested by lung tumorigenesis induced by benzopyrene. We previously observed that AIMP2-deficient mice show higher cell proliferation (Kim, M. J., Park, B.-J., Kang, Y.-S., Kim, H. J., Park, J.-H. Kang, J. W., Lee, S. W., Han, J. M., Lee, H.-W., Kim, S. Downregulation of fuse-binding protein and c-myc by tRNA synthetase cofactor, p38, is required for lung differentiation. Nat. Genet. 34, 330-336 (2003)). Here we checked whether AIMP2−/− cells would also show difference in cell death. We prepared mouse embryonic fibroblasts from AIMP2 wild type, hetero- and homozygous mice and compared them in the resistance to cell death induced by a carcinogen, benzopyrene (BP), treatment. The number of AIMP2 wild type MEFs was more rapidly decreased than the hetero- and homozygous cells by the BP treatment (FIG. 13a). We also compared the number of apoptotic cells in different tissues isolated from the wild type and homozygous cells. The AIMP2-deficient tissues showed decreased apoptotic cells compared to the corresponding regions of the wild type mice (FIG. 13b). Thus, the AIMP2 depletion appears to render resistance to cell death. We then checked how AIMP2 would affect the in vivo susceptibility to lung tumorigenesis that is induced by BP. Since AIMP2$^{-/-}$ mice are neo-natal lethal due to lung disorder (Kim, M. J., Park, B.-J., Kang, Y.-S., Kim, H. J., Park, J.-H. Kang, J. W., Lee, S. W., Han, J. M., Lee, H.-W., Kim, S. Downregulation of fuse-binding protein and c-myc by tRNA synthetase cofactor, p38, is required for lung differentiation. Nat. Genet. 34, 330-336 (2003)), we decided to use the heterozygous mice. We induced lung tumorigenesis by intraperitoneal injection of BP as previously described (Wang, Y., Zhang, Z., Kastens, E., Lubet, R. A. & You, M. Mice with alterations in both p53 and Ink4a/Arf display a striking increase in lung tumor multiplicity and progression: differential chemopreventive effect of budesonide in wild-type and mutant A/J mice. Cancer Res. 63, 4389-4395 (2003)) and compared the frequency of the tumor formation from 6 weeks after BP injection. AIMP2$^{+/-}$ mice developed lung tumors at about 2 fold higher frequency than the wild type littermates (FIGS. 13c and d). These results suggest pro-apoptotic and tumor suppressive activities of AIMP2.

Figure 13E:
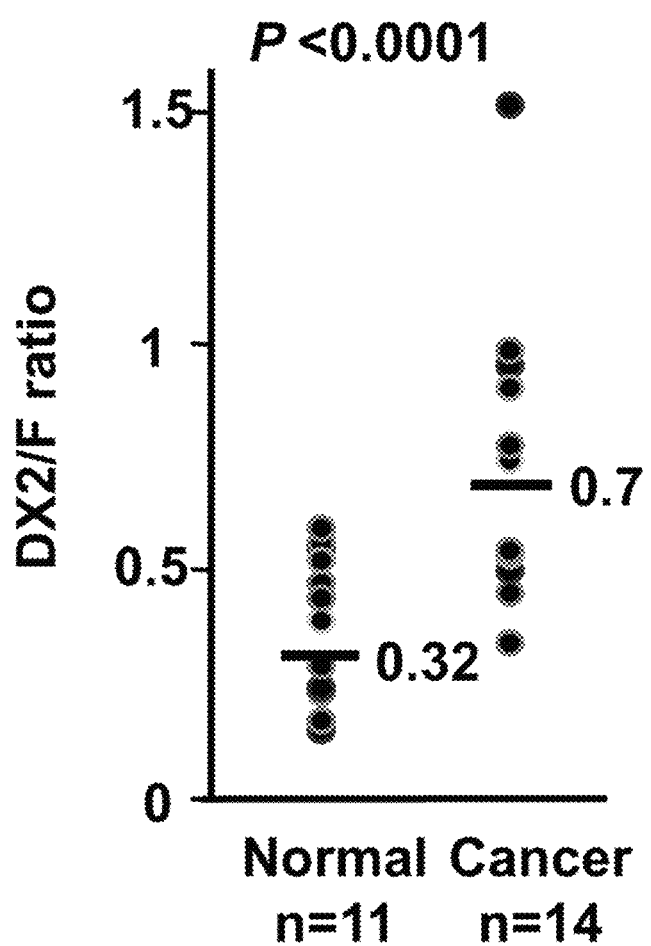

Noticeable was that AIMP2-DX2 was more highly expressed in lung cancer cell lines (A549, H322, H460 and H157) than in normal cells (WI-26 and NL-20), implying its potential association with cancer formation. To confirm this possibility, we separated cancer and normal tissues from adenocarcinoma lung cancer patients by laser micro-dissection, isolated RNAs and then conducted quantitative real-time RT-PCR to measure the relative expression of AIMP2-DX2 to AIMP2-F. The expression of AIMP2-DX2 to AIMP2-F was generally higher in the cancerous regions compared to that of the normal counterparts (FIG. 13e). Higher expression of AIMP2-DX2 was also observed at high frequency in other lung cancer types (data not shown).

Oncogenic Property of AIMP2-DX2.

Figure 14A:
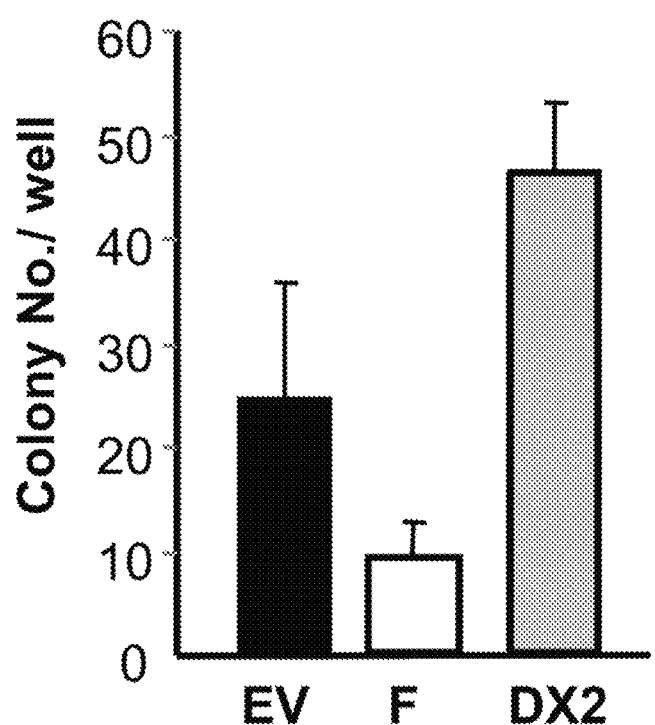
FIGS. 14a-14f show oncogenic property of AIMP2-DX2.
Figure 14B:
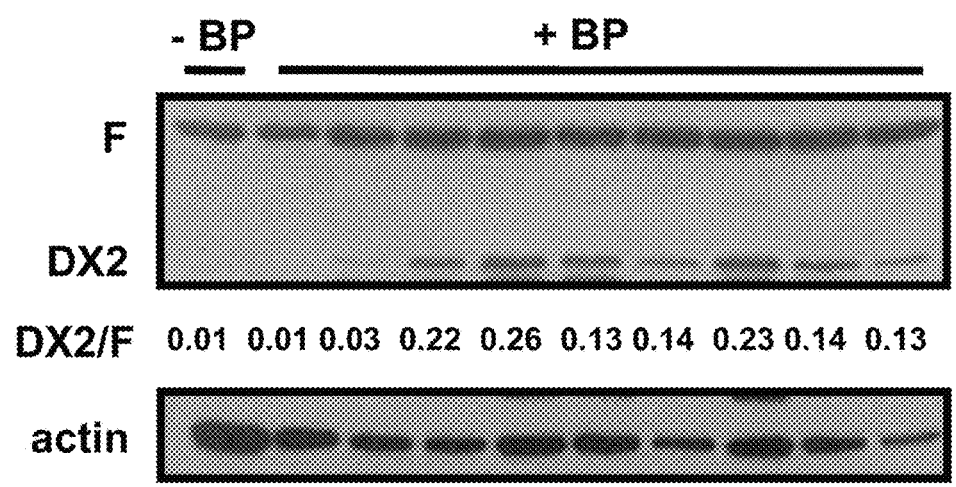
Figure 14C:
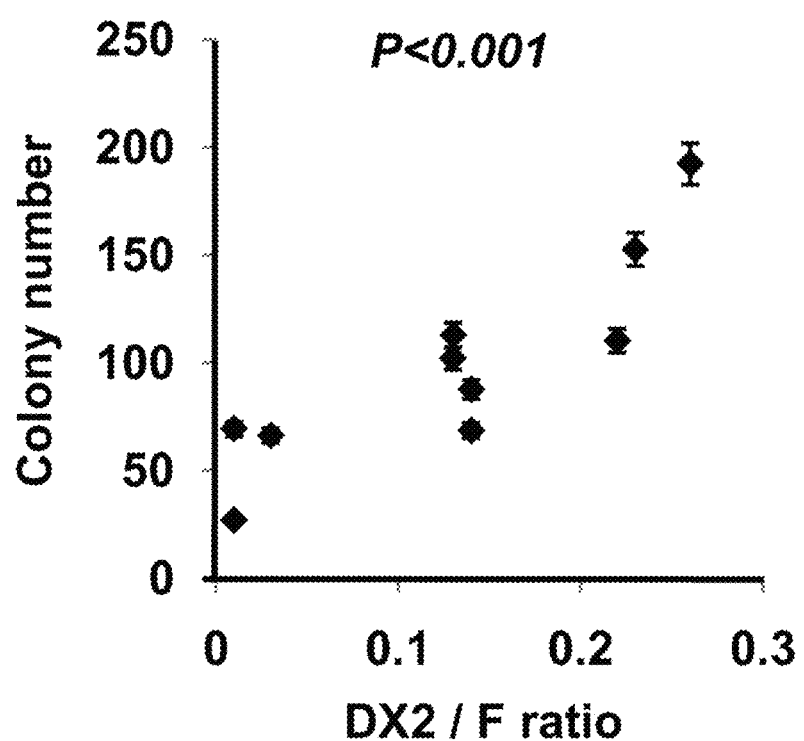
Figure 14D:
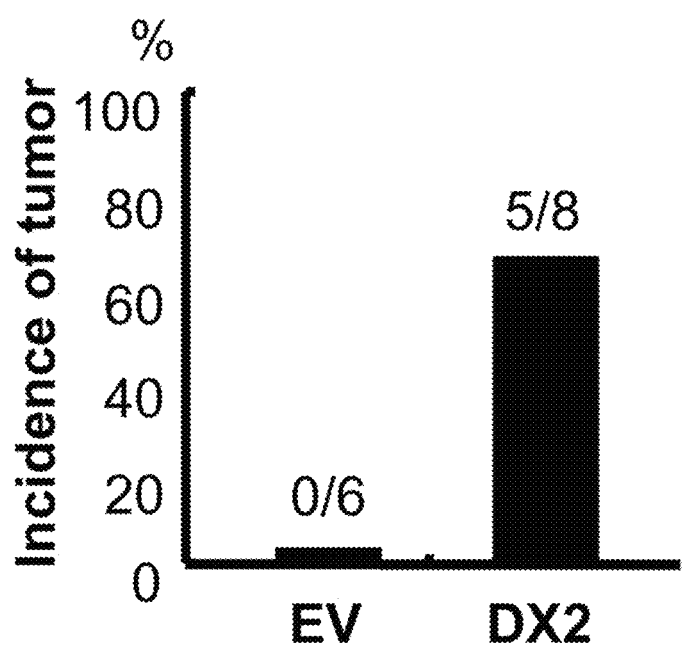
Figure 14E:
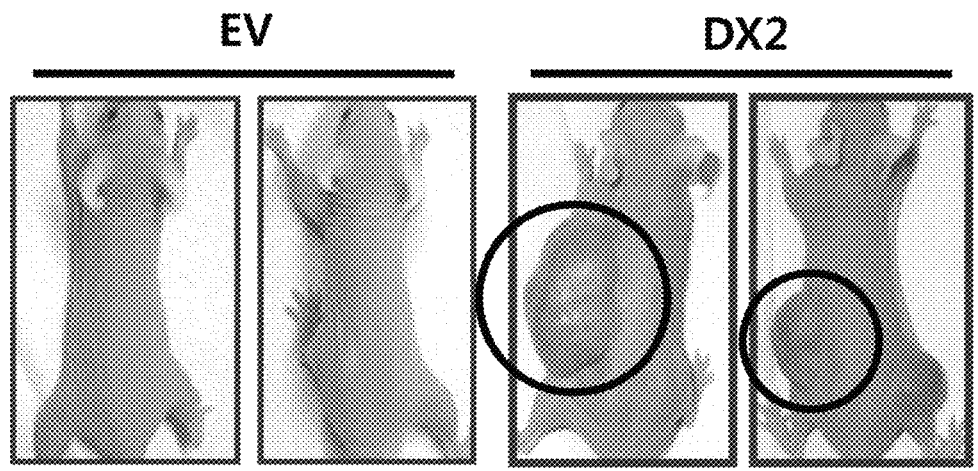
Figure 14F:
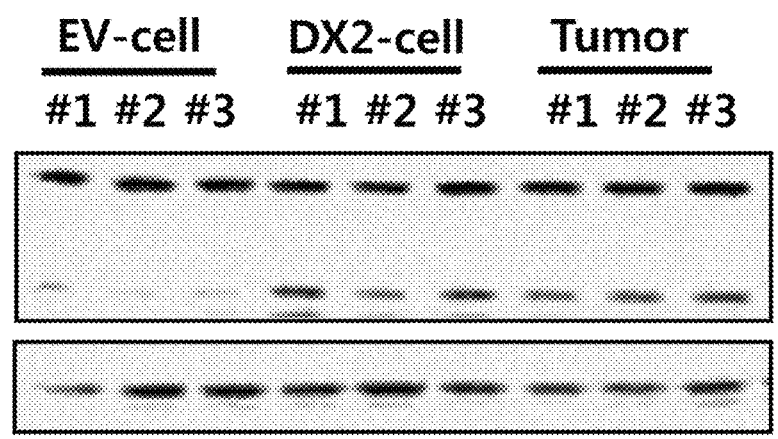

We then checked whether high expression of AIMP2-DX2 can induce cell transformation by anchorage-independent colony formation assay. We introduced AIMP2-F or -DX2 into AIMP2-deficient MEFs and compared the number of the resulting colonies. While transfection of AIMP2-F generated fewer colonies than the empty vector, AIMP2-DX2 increased the colony formation (FIG. 14a). In another test, we used normal lung WI-26 cells in which AIMP2-DX2 level is very low or undetectable (FIG. 14b the left most lane), and incubated them in the presence of BP. We then selected the surviving colonies and checked whether these colonies have increased expression of AIMP2-DX2 by Western blotting. The most of the selected colonies expressed higher expression of AIMP2-DX2 compared to the control cells (FIG. 14b) although the ratio of AIMP2-DX2 to -F varied significantly depending on the cells (FIG. 14b). We then compared the selected colonies in their ability of anchorage-independent colony formation as above. The resulting colony numbers showed positive correlation to the expression ratio of AIMP2-DX2 to -F (FIG. 14c). We also introduced EV or AIMP2-DX2 into MEFs and established the stable cell lines by G418 selection. We then isolated three AIMP2-DX2-overexpression and three EV-transfected cell lines, and injected them to nude mice. Five out of the eight mice that were injected with the DX2-overexpression cell lines produced tumors whereas none of the six mice injected with the EV stable cells induced tumors (FIG. 14d-e). To confirm that high level expression of AIMP2-DX2 was still maintained in the tumors, we isolated the tumors that were formed from AIMP2-DX2 overexpression cells and re-examined the expression of this variant by Western blotting. All of the three examined tumors expressed AIMP2-DX2 at the level similar to their originally transplanted cells (FIG. 14f). All of these results support the potential oncogenic property of AIMP2-DX2. The results above suggest that the tumor suppressive activity of AIMP2-F would be compromised by the expression of DX2.

Knock-Down of AIMP2-DX2 Using Si-RNA Suppresses Tumor Growth

Figure 15A:
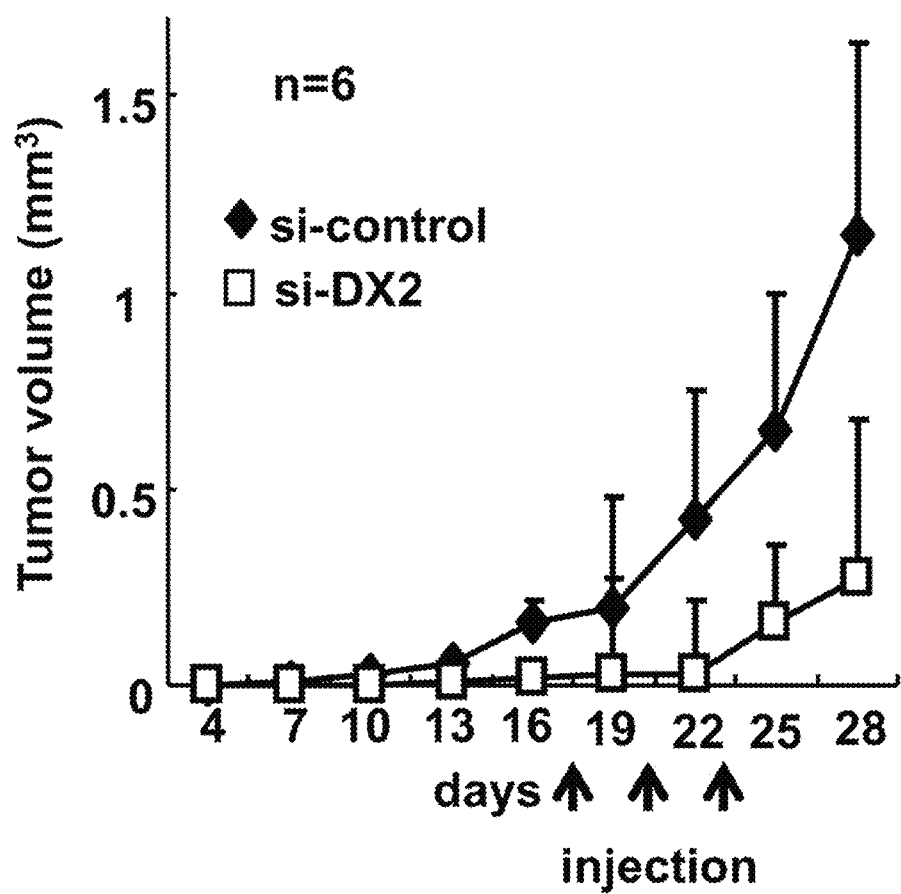
FIGS. 15a-15f shows knock-down of AIMP2-DX2 using si-AIMP2-DX2 suppresses tumor growth.
Figure 15B:
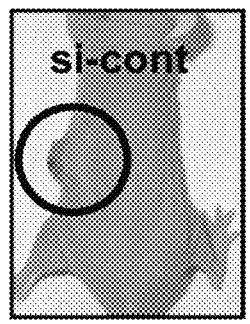
Figure 15B:
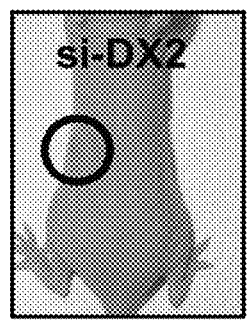
Figure 15C:
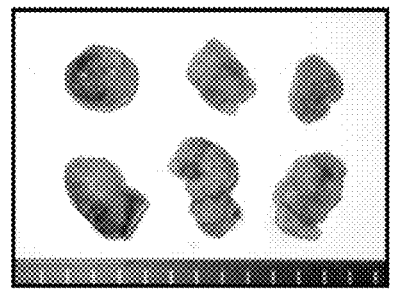
Figure 15C:
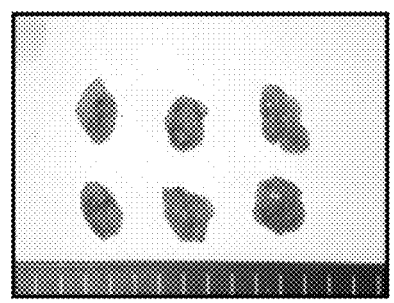
Figure 15D:
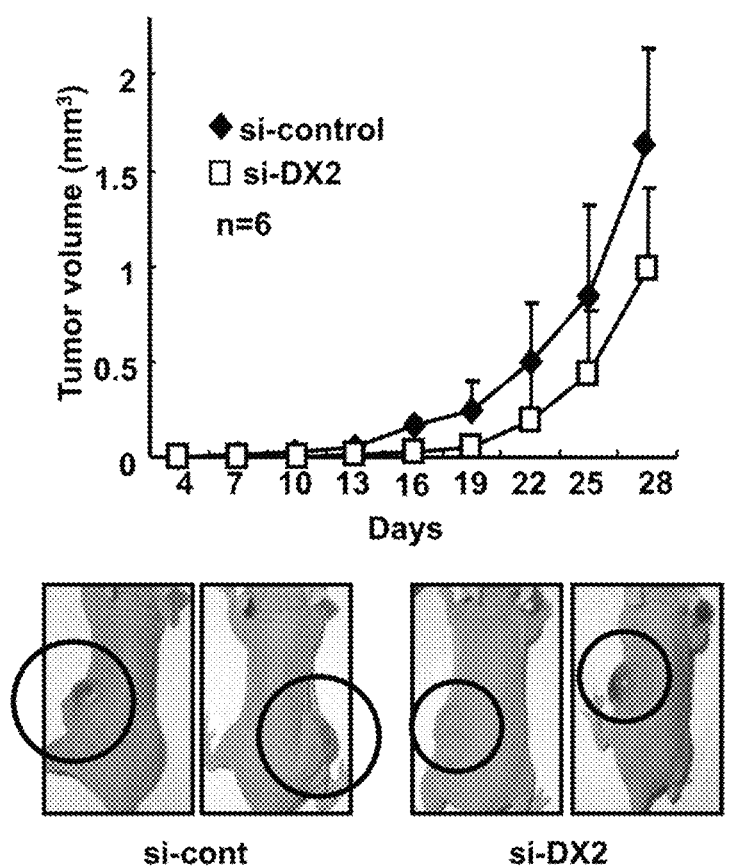
Figure 15E:
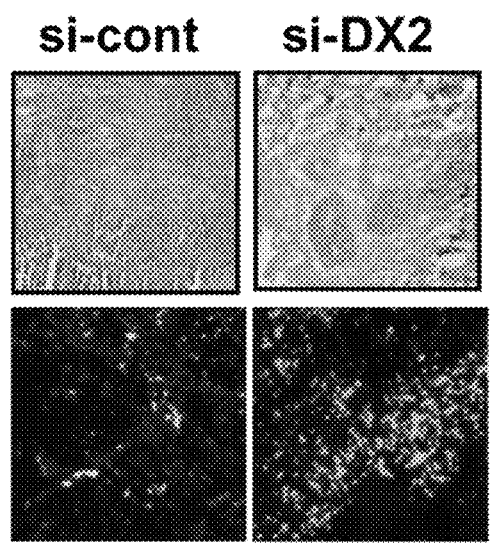

We investigated whether tumor progression can be controlled by the suppression of AIMP2-DX2 expression. We introduced si-control or si-AIMP2-DX2 into lung cancer cell, NCI-H460, and transplanted the stable transfectants to nude mice and compared the tumor growth by measuring tumor volume at time interval. The si-AIMP2-DX2-transfected cells showed retarded tumor growth compared to the control tumors (FIG. 15d). To see whether additional administration of si-AIMP2-DX2 can further suppress the tumor growth, we directly injected si-control and si-AIMP2-DX2 into the growing tumors in 17, 21 and 23 days after the cell transplantation. The intratumoral injection of si-AIMP2-DX2 further suppressed tumor growth compared to the si-control-injected tumors as determined by tumor volume (FIG. 15a-c). We isolated tumors from si-control or si-AIMP2-DX2-treated mice after 28 days, and examined whether AIMP2-DX2 expression was actually suppressed by the delivery of si-AIMP2-DX2. We then isolated the si-control and -DX2-treated tumors and compared the cell density and death by histological analyses and Apoptag staining. The si-AIMP2-DX2-treated tumors showed less compact histological characteristics (FIG. 15e upper) and higher apoptotic cell population (FIG. 15e lower) than the si-control treated tumors, implying that the cell death should occur more actively in the AIMP2-DX2-suppressed tumors.

Figure 15F:
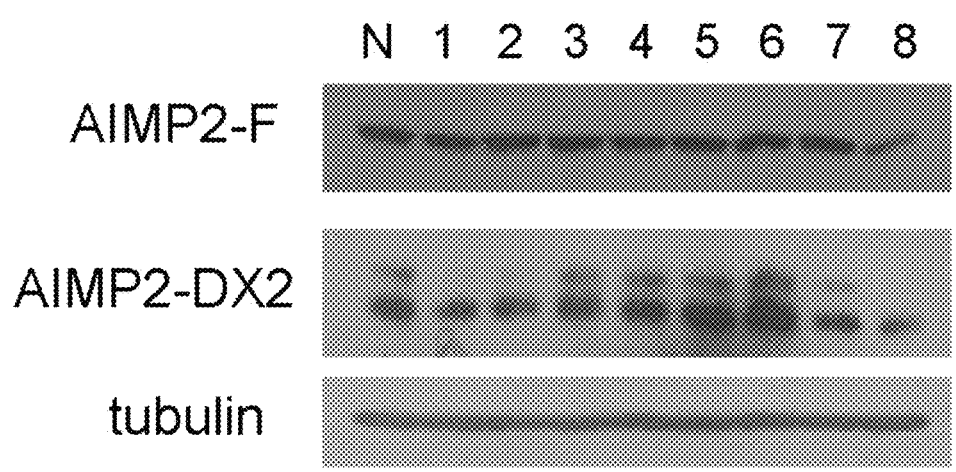

We transfected si-control or si-AIMP2-DX2 of Table 1 into H460 cell, and compared the expression of AIMP2-F and AIMP2-DX2 using western blot with AIMP2-DX2 monoclonal antibody (clone number 324). As a result, AIMP2-DX2 expression was reduced in H460 cell by treating si-AIMP2-DX2 of Table 1 (FIG. 15f). The immunoglobulin isotype of AIMP2-DX2 monoclonal antibody (clone number 324) is IgG, and its epitope is from $84^{th}$ to $225^{th}$ of SEQ ID NO:2.

Figure 16A:
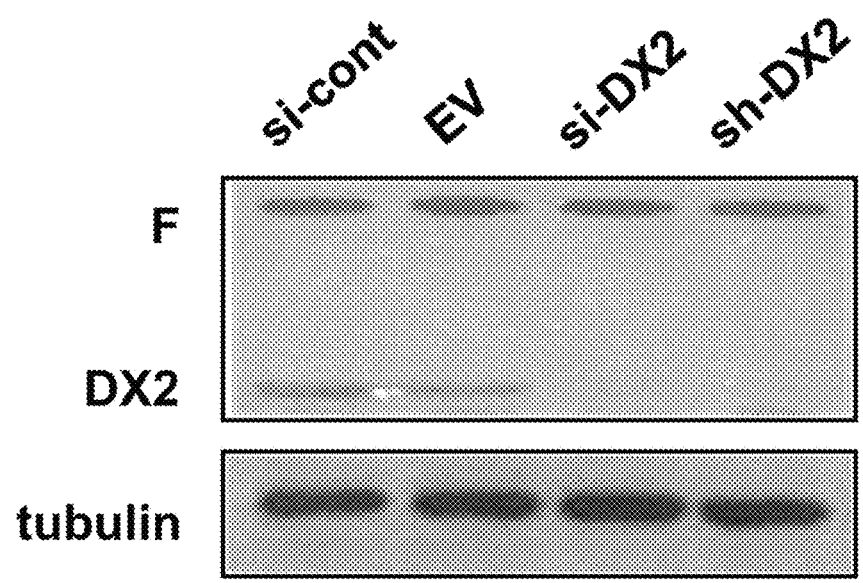
FIGS. 16a-16c shows delivery of GFP-expressing plasmid to the various parts of mouse lung via intranasal inhalation.
Figure 16B:
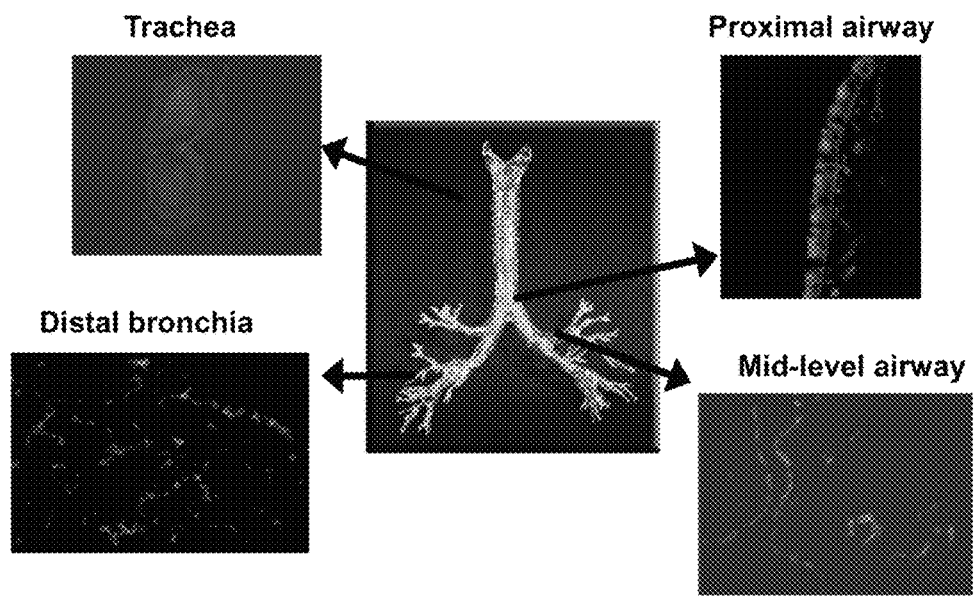
Figure 16C:
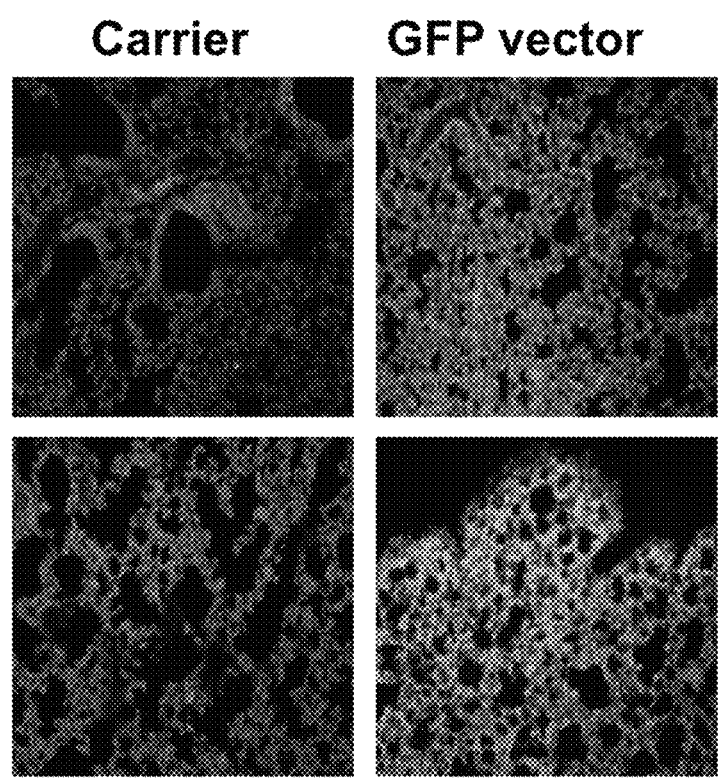

Delivery of GFP-Expressing Plasmid to the Various Parts of Mouse Lung Via Intranasal Inhalation Since benzopyrene (BP) induces AIMP2-DX2 expression and lung tumors, we tested whether suppression of AIMP2-DX2 can retard the growth of the BP-induced tumors. For the experiment, we constructed the plasmid encoding shRNA (short hairpin RNA) suppressing AIMP2-DX2 and checked whether it can also retard tumor growth. The expressed shRNA specifically suppressed the expression of AIMP2-DX2, but not AIMP2-F, as determined by Western blotting of AIMP2 (FIG. 16a). For the delivery of the sh-AIMP2-DX2-encoding plasmid into lung, we used the nasal inhalation system that we previously used for the delivery of the plasmid encoding tumor suppressor PTEN (Kim, H. W., et al. Aerosol delivery of glucosylated polyethylenimine/phosphatase and tensin homologue deleted on chromosome 10 complex suppresses Akt downstream pathways in the lung of K-ras null mice. Cancer Res. 64, 7971-7976 (2004)). We checked the delivery efficiency of the plasmid DNA into various parts of lung by the expression of green fluorescence protein (GFP) encoded by the same plasmid. The GFP-plasmid was mixed with glucosylated PEI and the DNA vapor was generated by sonication in microwave chamber as previously described. After the inhalation, the mice were sacrificed and expression of GFP was examined in various regions of airway and lung alveoli. Most of the isolated tissues showed GFP expression (FIGS. 16b and c).

Knock-Down of AIMP2-DX2 Using Sh-RNA Suppresses Tumor Growth

Figure 17A:
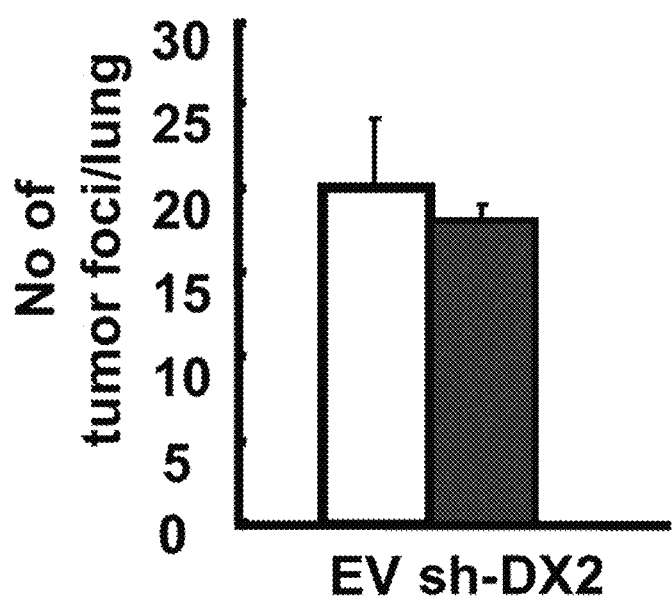
FIGS. 17a-17f shows knock-down of AIMP2-DX2 using sh-AIMP2-DX2 suppresses tumor growth. The lung tumors were induced by BP and the EV and sh-AIMP2-DX2 plasmids were delivered via nasal inhalation. After four weeks of the inhaled therapy, lungs were isolated and the number of tumor nodules (a) and tumor area (b) were determined after hematoxylin and eosin staining.
Figure 17B:
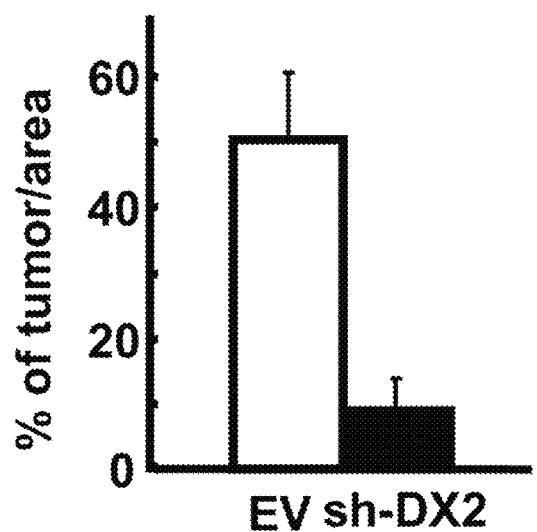
Figure 17C:
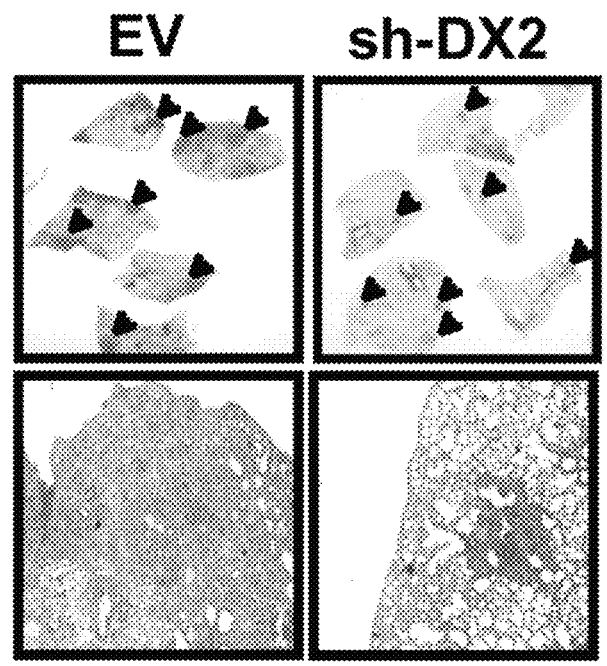
Figure 17D:
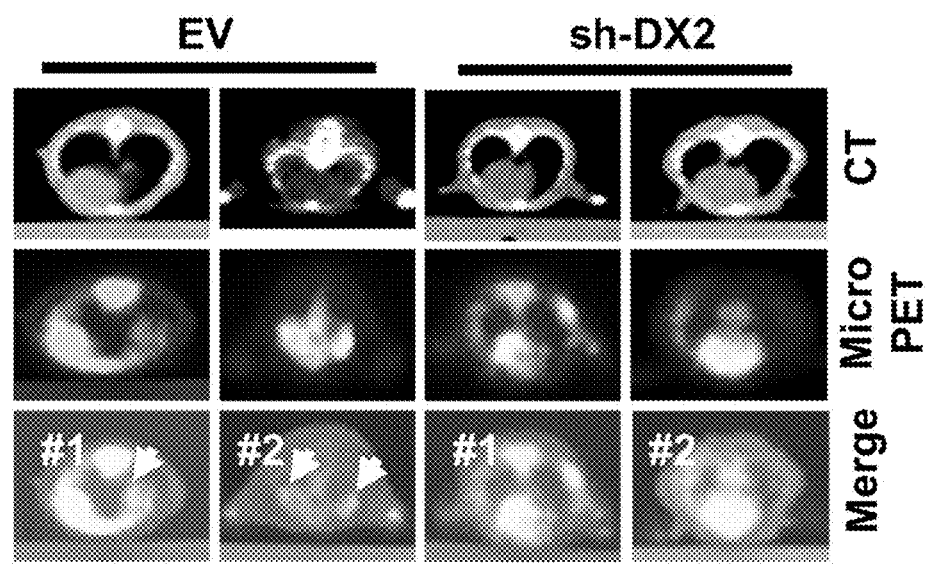
Figure 17E:
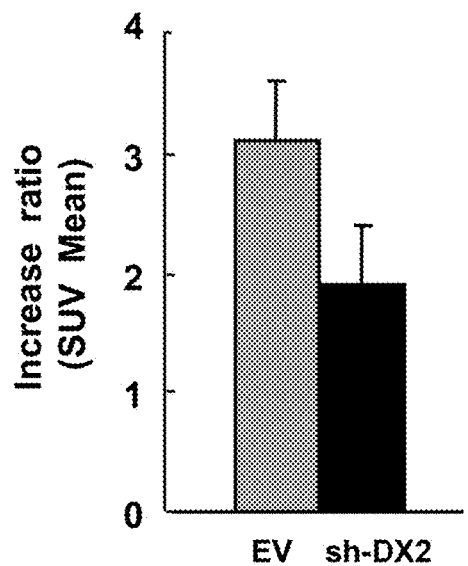
Figure 17F:
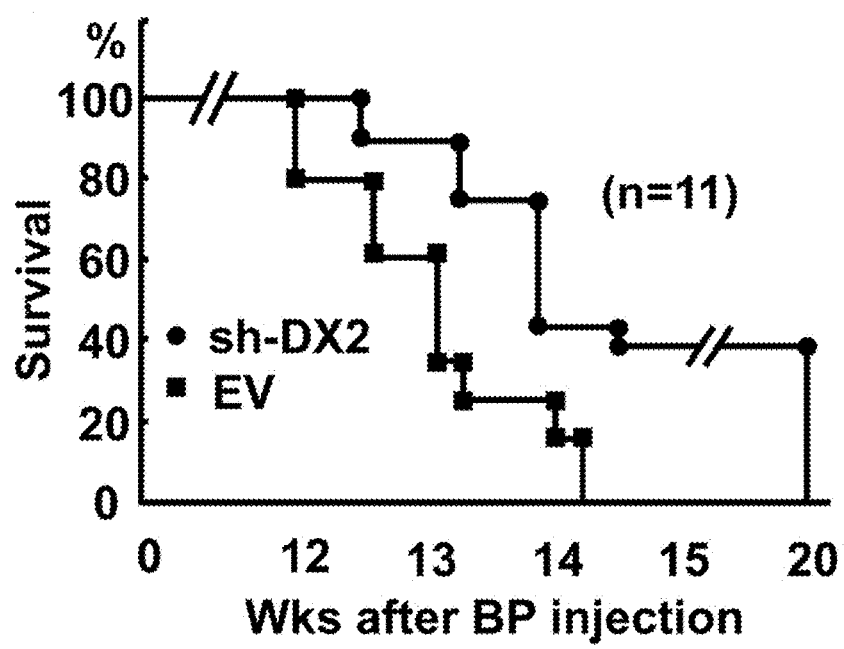

After confirming the efficient delivery of the DNA into lung alveoli, we delivered the sh-AIMP2-DX2-encoding plasmid DNA to the lungs of the mice twice a week from 6 weeks after the injection of BP. The mice were sacrificed 4 weeks after the administration of the DNA, and the tumor growth was monitored by morphological and histological analyses. The areas and histology of lung tumor region isolated from the sh-AIMP2-DX2-treated mice were compared with those of the control group. While the numbers of tumor nodules induced by BP were similar between the two groups of the mice (FIGS. 17a and c upper panel, arrow heads), the tumor area was reduced to about 10% of the total measured lung area in sh-AIMP2-DX2-treated lungs whereas about 50% remained as cancer region in the control group (FIGS. 17b and c lower panel). The lungs were selected from the EV and sh-DX2 plasmid-treated mice (n=2) and the tumor regions between the two groups were also compared by the combination of micro-PET and CT scanning analyses. For micro-PET analysis, we injected fluoro-2-deoxy-D-glucose (18FDG) into mice via tail vein and measured the FDG uptake rate in the tumors before and 12 weeks after DNA delivery. The FDG uptake rate in the sh-AIMP2-DX2 treated tumors increased less than 2 fold whereas more than 3 fold increase was observed in the control tumors (FIGS. 17d and e). In addition, we investigated whether the lung delivery of the sh-DX2 plasmid could improve the survival of the mice containing lung tumors. The survival rate of the sh-DX2 plasmid-treated group was significantly improved compared to the EV-treated group (FIG. 17*f*). Combined together, the inhibition of AIMP2-DX2 appears to suppress tumor growth and improve the survival of the lung tumor-containing mice.

Production of Anti-AIMP2-DX2 Monoclonal Antibody H5 IgG and Antibody Fragment H5 Fab A. Construction of Chimeric Fab Library A rabbit/human chimeric Fab library for screening an antigen-binding site specifically binding to AIMP2-DX2 protein was constructed. Rabbit immunization, mRNA extraction and cDNA synthesis from the splenocytes of the rabbit, and the rabbit/human chimeric Fab antibody library construction were carried out fundamentally in accordance with the method known in 'Phage Display: A Laboratory Manual' (Barbas, C. F. 3rd. et al. Eds. Cold Spring Harbor Laboratory Press).

Specifically, a polypeptide corresponding to exon 1-exon 3 junction of AIMP2-DX2 (i.e., amino acid sequence GHVQDYGALKD) (SEQ ID NO: 219) was used as an epitope capable of differentiating the wild type AIMP2 protein from AIMP2-DX2 mutant protein. In order to conjugate keyhole limpet hemocyanin (KLH), which is a carrier protein, to the C-terminal of the AIMP-DX2 antigen peptide, the cysteine (C) amino acid was added. The AIMP2-DX2 antigen peptide conjugated to KLH was inoculated in a rabbit to induce an immune response. The spleen of the rabbit was obtained, and mRNAs were extracted therefrom. A reverse transcription-polymerase chain reaction (RT-PCR) was used to prepare complementary DNAs (cDNAs) of variable regions of the rabbit antibody necessary for the chimeric Fab library construction. Primers used for the cDNA preparation were described in Table 4. DNA amplification of the rabbit antibody's heavy and light chain variable regions was carried out from the prepared cDNAs using a combination of primers listed in Table 5 and PCR conditions as described in Table 6. The amplified PCR products were separated on 1.0% agarose gel electrophoresis, and then purified using a gel extraction kit.

TABLE 4

Primers for RT-PCT

Forward Primers

| | | | | | | | |
|---|---|---|---|---|---|---|---|
| Heavy Chain (SEQ ID NO.) | RVH1 (182) | RVH2 (183) | RVH3 (184) | RVH4 (185) | RVH5 (186) | RVH6 (187) | |
| Light Chain (kappa) (SEQ ID NO.) | RVK1 (188) | RVK2 (189) | RVK3 (190) | RVK4 (191) | RVK5 (192) | RVK6 (193) | RVK7 (194) | RVK8 (195) |
| Light Chain (lambda) (SEQ ID NO.) | RVL1 (196) | RVL2 (197) | RVL3 (198) | RVL4 (199) | RVL5 (200) | RVL6 (201) | |

Reverse Primers

| | | | | |
|---|---|---|---|---|
| Heavy Chain (SEQ ID NO.) | RJH-b (202) | | | |
| Light Chain (kappa) (SEQ ID NO.) | RJK1-b (203) | RJK2-b (204) | RJK3-b (205) | RJK4-b (206) |
| Light Chain (lambda) (SEQ ID NO.) | RJL-b (207) | | | |

TABLE 5

Primer Combinations for RT-PCR

44 Primer Combinations (Forward & Reverse Primers)

| | | | | | | | | |
|---|---|---|---|---|---|---|---|---|
| Heavy Chain | RVH1 | RVH2 | RVH3 | RVH4 | RVH5 | RVH6 | | |
| | RJH-b | RJH-b | RJH-b | RJH-b | RJH-b | RJH-b | | |
| Light Chain (kappa) | RVK1 | RVK2 | RVK3 | RVK4 | RVK5 | RVK6 | RVK7 | RVK8 |
| | RJK1-b | RJK1-b | RJK1-b | RJK1-b | RJK1-b | RJK1-b | RJK1-b | RJK1-b |
| | RVK1 | RVK2 | RVK3 | RVK4 | RVK5 | RVK6 | RVK7 | RVK8 |
| | RJK2-b | RJK2-b | RJK2-b | RJK2-b | RJK2-b | RJK2-b | RJK2-b | RJK2-b |
| | RVK1 | RVK2 | RVK3 | RVK4 | RVK5 | RVK6 | RVK7 | RVK8 |
| | RJK3-b | RJK3-b | RJK3-b | RJK3-b | RJK3-b | RJK3-b | RJK3-b | RJK3-b |
| | RVK1 | RVK2 | RVK3 | RVK4 | RVK5 | RVK6 | RVK7 | RVK8 |
| | RJK4-b | RJK4-b | RJK4-b | RJK4-b | RJK4-b | RJK4-b | RJK4-b | RJK4-b |
| Light Chain (lambda) | RVL1 | RVL2 | RVL3 | RVL4 | RVL5 | RVL6 | | |
| | RJL-b | RJL-b | RJL-b | RJL-b | RJL-b | RJL-b | | |

TABLE 6

PCR conditions for DNA amplification of the rabbit
antibody's heavy and light chain variable regions

| PCR Reaction Program | 30x | | | | |
|---|---|---|---|---|---|
| 94° C. | 94° C. | 56° C. | 72° C. | 72° C. | 4° C. |
| 2 min | 30 sec | 30 sec | 30 sec | 7 min | ∞ |

(∞ means no limitation to time)

The human antibody (Fab) constant region DNAs that is necessary for the preparation of the chimeric Fab library construction were obtained, via PCR, from pComb3XTT containing human Fab. The light and heavy chain constant regions were amplified by the HKC-F (forward) and Lead-b (reverse) primer pair and the HIgGCH1-F (forward) and dpseq (reverse) primer pair, respectively, while the pComb3XTT (2640.2 ng/ml) plasmid was used as a template, according to PCR conditions as described in Table 7. The amplified PCR products were purified using the gel extraction kit. The purified heavy and light chain constant region DNA sequences were 400 bp and 350 bp in length, respectively.

TABLE 7

PCR conditions for DNA amplification of the rabbit
antibody's heavy and light chain constant regions

| PCR Reaction Program | 25x | | | | |
|---|---|---|---|---|---|
| 94° C. | 94° C. | 56° C. | 72° C. | 72° C. | 4° C. |
| 2 min | 30 sec | 30 sec | 30 sec | 10 min | ∞ |

(∞ means no limitation to time)

The rabbit antibody variable region DNAs and the human antibody (Fab) constant region DNAs were conjugated to each other through overlap extension PCR. The PCR reaction of the heavy chain was carried out using the LeadVH and dpseq primer pair, while a mixture of heavy chain variable region DNAs and constant region DNAs was used as a template. The PCR reaction of the light chain was carried out using the RSC-SF and Lead-b primer pair, while a mixture of light chain variable region DNAs and constant region DNAs was used as a template. PCR conditions are described in Table 8.

TABLE 8

Overlap extension PCR conditions

| PCR Reaction Program | 25x | | | | |
|---|---|---|---|---|---|
| 94° C. | 94° C. | 56° C. | 72° C. | 72° C. | 4° C. |
| 2 min | 30 sec | 30 sec | 1 min | 10 min | ∞ |

(∞ means no limitation to time)

The DNA sequences of the thus prepared Fd heavy chain fragment (heavy chain constant region+heavy chain variable region) and chimeric light chain (light chain constant region+light chain variable region) were separated and purified using the gel extraction kit. The heavy and light chain PCR products were 750 bp and 800 bp in length, respectively. Last, in order to conjugate the Fd heavy chain fragment and the chimeric light chain as a Fab form, PCR was carried out by using the RSC-SF and dpseq primer pair, while a mixture of the Fd heavy chain and the chimeric light chain was used as a template, according to the conditions as described in Table 9. Fab (Fd heavy chain+chimeric chain) obtained as a PCR product was electrophoresed on 1.5% gel, and then separated and purified by the gel extraction kit. The final product was 1500 bp in length.

TABLE 9

PCR conditions for the preparation of Fab

| PCR Reaction Program | 25x | | | | |
|---|---|---|---|---|---|
| 94° C. | 94° C. | 56° C. | 72° C. | 72° C. | 4° C. |
| 2 min | 30 sec | 30 sec | 1.5 min | 10 min | ∞ |

(∞ means no limitation to time)

The prepared Fab DNAs as described above were inserted into the pComb3XTT vector to allow the Fab DNAs to be expressed in the phage to construct the phage-displayed Fab library. Specifically, the Fab PCR product and the pComb3XTT vector were cleaved with restriction enzyme SfiI, respectively, and then electrophoresed on 1% gel, followed by separation and purification. The restriction enzyme reaction was carried out by cleaving 5 μg of Fab DNAs and 30 μg of pComb3XTT vector with restriction enzyme SfiI, respectively. The cleaved Fab DNAs and vector were 1500 bp and 3400 bp in length, respectively. The insert DNA and the vector, which were cleaved with the restriction enzyme, were mixed at a mole ratio of 3:1, followed by reaction with T4 ligase and then precipitation with ethanol.

The chimeric Fab DNA-inserted vector was used to transfect E. coli ER2537 through electroporation. The super optimal broth with catabolite repression-glucose added (SOC) medium was used for the electroporation. 200 μl of ER2537 E. coli competent cells were mixed with the vector in the cooled cuvette, followed by an electric shock, and then 3 ml of SOC was immediately added. After that, the cells were transferred into a 50-ml tube, and then cultured at room temperature for 1 h. Then, the cells were coated on 100-mm agar plates containing 1 μl, 1/10 μl, and 1/100 μl of pre-warmed ampicillin. Separately, in order to investigate any contamination, the cells were also coated on a two-compartment plate containing kanamycin and ampicillin. The electrically shocked E. coli, which remained after the coating, was centrifuged at 4000 g for 15 min at 4° C., to remove the supernatant, and was then resuspended in 500 μl of SOC, and then coated on the 150-mm ampicillin plate. This plate was cultured at 37° C. for 18 h together with the 100 mm-plates that were previously coated with E. coli. The next day, approximately 107 transgenic colonies were obtained as resultant products.

B. Phage-Displayed Fab Library Panning and Screening
<1> Phage-Displayed Fab Library Panning In order to screen Fab having an antigen-binding site specifically binding to the AIMP2-DX2 antigen peptide, the panning of the antibody (Fab) library prepared as described above was carried out according to the known methods (Bai et al. PLoS ONE 2015, doi:10.1371/journal.pone.0141045).

As the first stage of panning, library rescue was performed to introduce helper phage into E. coli. One day before the experiment, colonies coated and grown on the 150-mm plate were inoculated and collected in 5 ml of Luria-Bertani Broth (LB), and then 100 μl thereof was inoculated in 20 ml of Super Broth (SB) containing ampicillin (50 μg/ml), followed by shaking culture at 220 rpm for 3 h at 37° C. When the absorbance at 600 nm (OD600) of the culture reached 0.5, 500 μl of VCSM13 helper phage (1012 pfu) was added thereto, followed by shaking culture at 120 rpm for 1 h at 37° C. Thereafter, kanamycin (70 μg/ml) was added, followed by shaking culture at 220 rpm for 18 h at 30° C. The culture was centrifuged at 12,000 rpm for 20 min at 4° C. to collect the supernatant, which was then added to a polyethylene glycol (PEG) precipitation solution (16% PEG-8000, 12% NaCl), and placed on ice for 30 min. In addition, the pellets obtained by centrifugation at 12,000 rpm for 20 min were resuspended in 1 ml of PBS containing 3% BSA to prepare a phage solution, which was then left at room temperature for 1 h. Separately, 160 μl of E. coli ER2537 was inoculated in 10 ml of LB, followed by shaking culture at 220 rpm and 37° C. without antibiotics.

1 ml of PBS containing 10 μg of the AIMP2-DX2 antigen peptide (in the form of BSA-conjugated antigen peptide used in the rabbit immune reaction) was coated on an immunotube (Nunc cat. No 470319) for panning, followed by reaction at 37° C. for 1 h, thereby allowing the antigen peptide to be adsorbed on an internal surface of the tube. Thereafter, the tube was blocked for 1 h with 3% skim milk in PBS-tween 20 (PBST), thereby filling the antigen-non-binding portion of the tube. The phage library (1012 cfu) was also blocked for 1 h with 1 ml of PBST containing 3% skim milk and 300 μg BSA.

The phage library was added to the blocked immunotube and incubated for 2 h at 37° C. with shaking, thereby allowing Fab and the antigen peptide, which were expressed in the phage, to bind to each other, followed by washing three times with 5 ml of PBST. The phages bound to the immunotube were eluted with 1 ml of triethylamine (100 mM in deionized water) at room temperature for 10 min. The eluted phages were immediately neutralized with 0.5 ml of Tris (1M, pH 7.0), and mixed with 8.5 ml of mid-log phage E. coli ER2537. The E. coli and phage culture were incubated at 37° C. for 1 h with gentle shaking (120 rpm), and subsequently plated on an LB agar plate with 2% glucose and ampicillin, followed by incubation overnight at 37° C. About 108 cells of E. coli that were grown on the plate were inoculated in 20 ml of SB medium (super broth: 3% tryptone, 2% yeast extract, and 1% MOPS, pH 7.0) with ampicillin, followed by culturing, and when the OD600 value reached 0.7, 1012 pfu of VCSM13 helper phage was added. After agitation (80 rpm) at 37° C. for 1 h, kanamycin (70 μg/ml) was added, and the culture was incubated overnight at 30° C. with shaking (200 rpm). The culture was centrifuged, and phages were precipitated by adding 5 ml of 5×PEG precipitation solution (20% (w/v) PEG8000, 15% (w/v) NaCl), followed by being placed on ice for 30 min. The precipitated phage was centrifuged, and resuspended in 0.3 ml PBS, which was then used for the next round of panning. The panning was repeated four times according to the above method, and E. coli colonies screened from the panning were obtained as products.

<2> Colony Screening

It was verified whether the antibody (Fab) expressed by the phages of colonies selected from the panning as described above specifically binds to the AIMP2-DX2 antigen peptide.

Out of colonies from 2nd to 4th rounds of panning, the colonies binding to the BSA-conjugated AIMP2-DX2 antigen peptide were screened by ELISA, according to the method by Bai et al (2015). The 96-well immunoplate for ELISA was coated with AIMP2-DX2 antigen peptide (10 μl/ml), and blocked with 180 μl of 3% BSA-PBST. The E. coli culture expressing the antibody (Fab) was centrifuged at 3500 rpm for 15 min for precipitation, and 40 μl of 1×TES (20% sucrose, 1 mM EDTA, 50 mM TRIS, pH 8.0) and 60 μl of 0.2×TES were sequentially added and resuspended to remove the extracellular membrane and prepare the periplasmic extract. 25 μl of the supernatant obtained by centrifuging the periplasmic extract was added to the immunoplate coated with the antigen peptide, followed by reaction for 1 h. Upon the completion of the reaction, the plate was washed three or four times with PBST, and as a secondary antibody, 25 μl of anti-human IgG (Fab specific)-HRP (1:1000) diluted with 3% BSA-PBST was added, followed by reaction at room temperature for 1 h. After washing the plate, a colorimetric reaction was performed for 10 min by adding 25 μl of tetramethylbenzidine (TMB), and then the reaction was stopped by adding 25 μl of sulfuric acid (H2SO4, 1 mM). As a negative control for ELISA, BSA was used instead of the antigen peptide, and the colonies that show a signal of more than 3-fold over the background were screened.

As for the antibody clones of the colonies, which were screened by ELISA, the binding specificity to AIMP2-DX2 was investigated using Western blotting. The previously screened E. coli colonies were cultured in 20 ml SB medium containing ampicillin, and IPTG (1 mM final) was added when OD600 reached 0.7, followed by culturing at 30° C. overnight with shaking. The E. coli cells precipitated through centrifugation were resuspended in 1 ml of cold 1×TES buffer, followed by the addition of 1.5 ml of cold 0.2×TES and culturing on ice for 30 min, thereby preparing the periplasmic extract. The supernatant obtained by centrifugation was mixed 1:1 with 3% skim milk-PBST, and used as a primary antibody for Western blotting. Anti-HA tag antibody-HRP or anti-human Fab antibody-HRP was used as a secondary antibody. As a result of Western blotting using the lysate of SW460 cells, which are a colon cancer cell line expressing AIMP2-DX2, the antibody (Fab) of colon H5 was found to specifically bind to AIMP-DX2 of 25 kDa (data not shown).

DNA sequences encoding Fab of the H5 clones of which binding to the AIMP2-DX2 was confirmed through ELISA analysis were determined by nucleotide sequencing process. Nucleotide and amino acid sequences of the H5 Fab heavy and light chain complementarity determining regions (CDRs) are as shown in SEQ ID Nos. 160 to 171. Further, nucleotide and amino acid sequences of the H5 Fab heavy and light chain variable regions (VHs and VLs) are as shown in SEQ ID Nos. 172 to 175. Nucleotide and amino acid sequences of the H5 Fab heavy chain polypeptide (Fd, heavy chain variable region derived from rabbit antibody and heavy chain CH1 domain of human antibody) are as shown in SEQ ID Nos. 180 and 181. Nucleotide and amino acid sequences of the H5 Fab light chain polypeptide (light chain variable region derived from rabbit antibody and light chain Cκ domain of human antibody) are as shown in SEQ ID Nos. 178 and 179.

The H5 Fab as sequenced above was converted into a generally used form of an IgG whole antibody. Based on conventional methods for converting Fab into its corresponding IgG antibody, DNAs of the H5 Fab heavy and light chain variable regions were amplified with PCR, followed by being inserted into pVITR01 vector with appropriate restriction enzymes in which genes of human IgG1 heavy and light chain variable regions were cloned. The nucleotide and amino acid sequences of H5 IgG antibody's heavy chain polypeptide (heavy chain variable region derived from rabbit antibody and heavy chain constant region of human antibody) and light chain polypeptide (light chain variable region derived from rabbit antibody and light chain constant Cκ region of human antibody) as prepared by the above described methods are disclosed in SEQ ID Nos. 176 to 179.

The nucleotide and amino acid sequences of H5 IgG antibody's light chain are the same as those of H5 Fab's light chain. Vectors comprising DNAs for H5 IgG antibody were expressed in 293F cell lines, followed by isolation and purification with protein G affinity chromatography.

Binding Specificity of the Monoclonal Antibody H5 Against the AIMP2-DX2

The binding specificity of H5 IgG antibody or its fragment H5 Fab to the AIMP2-DX2 was further tested as below.

Figure 18:
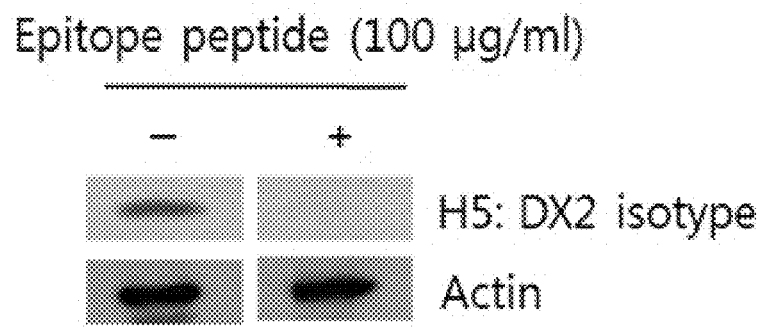
FIG. 18 shows a test result for confirming the binding specificity of the H5 Fab against the exemplary AIMP2-DX2 epitope peptide.

Firstly, antigen pre-adsorption analysis was conducted in order to confirm whether the prepared H5 Fab specifically binds to the AIMP2-DX2. After electrophoresis of cell lysates of H460 lung cancer cells which expressed the AIMP2-DX2, Western blot analysis was performed using a H5 Fab in the presence of 100 μg/ml of the AIMP2-DX2 epitope polypeptide (GHVQDYGALKD) (SEQ ID NO: 219) (indicated as "+" in FIG. 18) and a H5 Fab without the addition of the AIMP2-DX2 epitope peptide (indicated as "−" in FIG. 18), respectively. As shown in FIG. 18, it was found that the H5 Fab without the addition of the AIMP2-DX2 epitope peptide recognized the AIMP2-DX2 protein band, whereas the H5 antibody under a condition with the AIMP2-DX2 epitope peptide did not react with the AIMP2-DX2 protein band at all. These results confirm that the H5 Fab specifically binds to the AIMP2-DX2 protein.

Figures 19A, 19B:
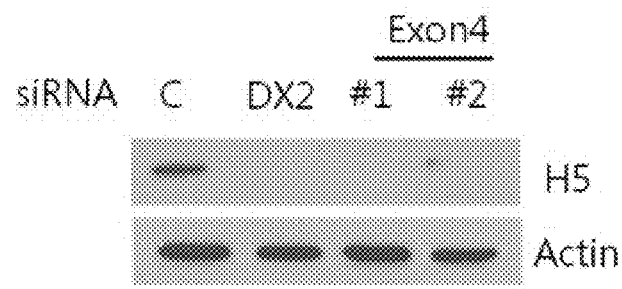
FIG. 19a and FIG. 19b further show a test result for confirming the binding specificity of the H5 Fab against the exemplary AIMP2-DX2 epitope peptide.

Secondly, the specific binding of the H5 Fab to the AIMP2-DX2 protein was further confirmed by suppressing the expression of the AIMP2-DX2 protein in H460 cells (See FIG. 19). H460 cells were transfected with siRNAs targeting the junction region between exon 1 and exon 3, and two different exon 4 regions of the AIMP2-DX2 (See indicated in FIG. 19b as "siDX2" of which nucleotide sequence is shown in SEQ ID NO. 214, "si exon 4 #1" of which nucleotide sequence is shown in SEQ ID NO: 215, and "si exon 4 #2" of which nucleotide sequence is shown in SEQ ID NO: 216), followed by incubation for 72 hours. H460 cell lysates were subjected to Western blot analysis using the H5 Fab. As shown in FIG. 19a, it was found that the AIMP2-DX2 protein band was not detected in H460 cell lysates transfected with the siRNAs targeting the junction region between exon 1 and exon 3. By the way, the AIMP2-DX2 protein band was also not detected in H460 cell lysates transfected with the siRNAs targeting exon 4, suggesting that all mRNAs of AIMP2-DX2 derivatives were destroyed by the siRNAs.

Figure 20A:
FIG. 20a and FIG. 20b show a test result of determining the effect of N-terminal amino acid deletion of the AIMP2-DX2 protein on the binding between the H5 Fab and the AIMP2-DX2 protein.
Figure 20B:
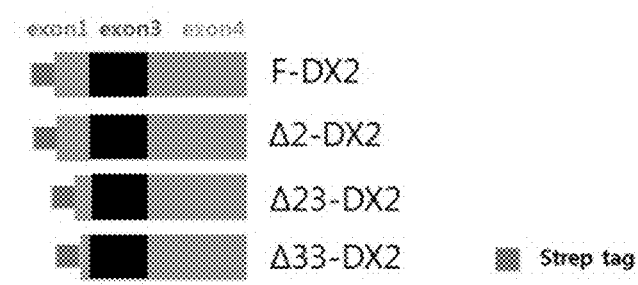
Figure 20B:

Further, the effect of N-terminal amino acid deletion of the AIMP2-DX2 protein on the binding between H5 Fab and AIMP2-DX2 protein was analyzed (See FIG. 20). It was reported that N-terminal amino acid residues of the AIMP2-DX2 exert a significant effect on the solubility of the AIMP2-DX2. AIMP2-DX2 derivatives in which the N-terminal two (2), twenty three (23) or thirty three (33) amino acid residues were deleted, respectively, were prepared (See FIG. 20b). The full-length AIMP2-DX2 and its isotypes were fused with strep tag and then expressed in the HEK293T cells, followed by Western blot analysis using H5 Fab. As shown in FIG. 20a, it was found that H5 Fab bound not only to the full-length AIMP2-DX2 protein ("F-DX2" or "F"), but also to its N-terminal deleted isotypes ("Δ2-DX2" or "Δ2", "Δ23-DX2" or "Δ23," and "Δ33-DX2" or "Δ33"). However, H5 Fab in the presence of the AIMP2-DX2 epitope peptide (i.e. amino acid residues 42 to 52 (GHVQDYGALKD) (SEQ ID NO: 219) as shown in SEQ ID NO: 2 or SEQ ID NO: 17) did not bind to either the full-length AIMP2-DX2 protein ("F-DX2" or "F") or its N-terminal deleted isotypes, confirming that the H5 Fab specifically binds to the AIMP2-DX2 protein.

Figure 21A:
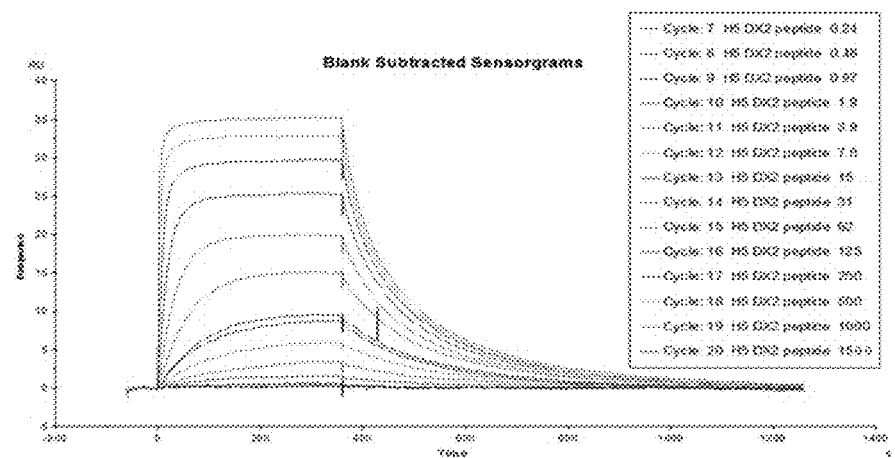
FIG. 21a and FIG. 21b shows the results of surface plasmon resonance analysis to determine the binding affinity between H5 IgG antibody and the exemplary AIMP2-DX2 epitope peptide. H5 antibody and IgG proteins were coated on the CM5 chips, while the exemplary AIMP2-DX2 epitope peptide (i.e. amino acid residues 42 to 52 (GHVQDYGALKD) (SEQ ID NO: 219) as shown in SEQ ID NO: 2 or SEQ ID NO: 17) at various concentrations was flowed over the chip.
Figure 21B:
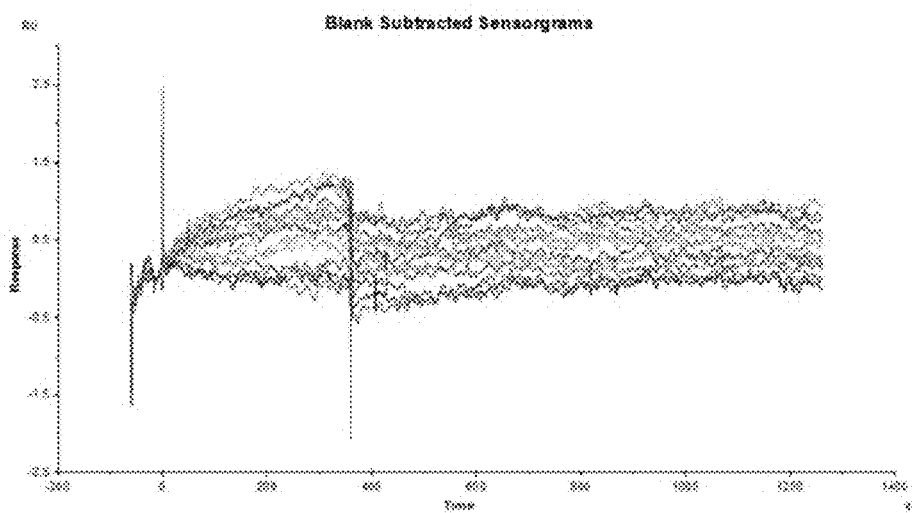

Still further, the binding affinity between H5 IgG antibody and the exemplary AIMP2-DX2 epitope peptide was determined by using surface plasmon resonance analysis (See FIG. 21). The H5 antibody (IgG) and IgG proteins were coated on the CM5 chips, while the exemplary AIMP2-DX2 epitope peptide at various concentrations was flowed over the chip to monitor the real time association and dissociation between H5 antibody and the exemplary AIMP2-DX2 epitope peptide. Analysis reagents and buffer were injected at the flow velocity of 15 μl/min. for 6 min, followed by washing for 20 min. Analysis was performed in sensorgram in which a response result of a blank without protein coating is subtracted from a response results between H5 antibody or IgG and the AIMP2-DX2 epitope peptides. As shown in FIG. 21, it was found that the binding affinity of the H5 antibody to the AIMP2-DX2 epitope peptide increased in an AIMP2-DX2 epitope peptide's concentration-dependent manner (See FIG. 21a), while IgG protein did not show a significant binding to the AIMP2-DX2 epitope peptide (See FIG. 21b).

Figure 22:
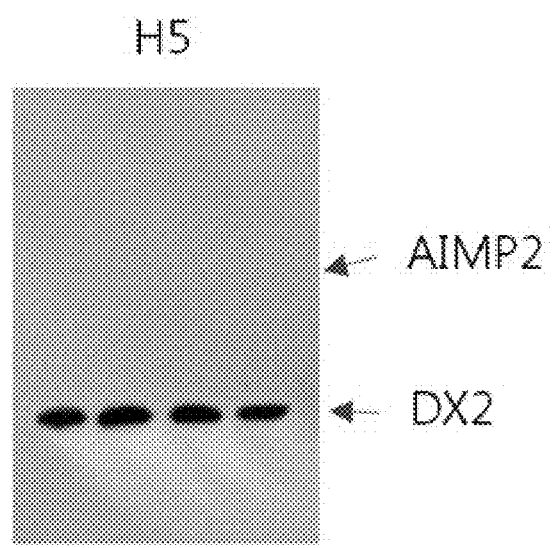
FIG. 22 shows the results of Western blot analysis for confirming a binding specificity of the H5 Fab to AIMP2-DX2 protein. The electrophoresis-conducted blots of H460 cell lysates were reacted with the H5 Fab. The location of the corresponding protein bands are indicated with arrows.

Lastly, it was tested whether H5 antibody is capable of differentiating AIMP2-DX2 from wild type AIMP2 protein (See FIG. 22). Western blot analysis was performed on H460 cell lysates using the H5 antibody. It was found that the H5 Fab specifically bound to the AIMP2-DX2 protein only, not wild type AIMP2 protein (See FIG. 22). This result confirms that the H5 antibody can be used to selectively recognize the AIMP2-DX2 protein.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. An antibody specifically binding to AIMP2-DX2 protein consisting of the amino acid sequence of SEQ ID NO: 2 or SEQ ID NO: 17,
   wherein the antibody specifically binds to the AIMP2-DX2 protein without binding to AIMP2 protein consisting of the amino acid sequence of SEQ ID NO: 217 or SEQ ID NO: 218,
   wherein the antibody specifically binds to a polypeptide comprising amino acid residues 42 to 52 (SEQ ID NO: 219), of the AIMP2-DX2 protein as shown in SEQ ID NO: 2 or SEQ ID NO: 17, and wherein the antibody comprises:
   a heavy chain variable region comprising the following complementarity determining regions: a heavy chain CDR1 as shown in SEQ ID NO: 160; a heavy chain CDR2 as shown in SEQ ID NO: 162; a heavy chain CDR3 as shown in SEQ ID NO: 164; and a light chain variable region comprising the following CDRs: a light chain CDR1 as shown in SEQ ID NO: 166; a light chain CDR2 as shown in SEQ ID NO: 168; and a light chain CDR3 as shown in SEQ ID NO: 170.

2. The antibody of claim 1, wherein the antibody is recombinant.

3. The antibody of claim 1, wherein the antibody is selected from the group consisting of a monoclonal antibody, a chimeric antibody, and a humanized antibody.

4. The antibody of claim 3, wherein the antibody is a monoclonal antibody.

5. The antibody of claim 1, wherein the antibody is selected from the group consisting of IgG, IgA, IgM, IgE, and IgD.

6. The antibody of claim 1, wherein the antibody is an antibody fragment selected from the group consisting of Fab, Fab', F(ab')$_2$, F(ab)$_2$, Fv, scFv, and diabody.

7. The antibody of claim 1, wherein the antibody specifically binds to a junction region between exon 1 and exon 3 of the AIMP2-DX2 protein.

8. The antibody of claim 1, wherein the antibody specifically binds to a polypeptide consisting of amino acid residues 42 to 52 (GHVQDYGALKD, SEQ. ID. NO: 219) of the AIMP2-DX2 protein as shown in SEQ ID NO: 2 or SEQ ID NO: 17.

9. The antibody of claim 1, wherein the antibody or antibody fragment comprises a heavy chain variable region comprising an amino acid sequence of SEQ ID NO: 172, and a light chain variable region comprising an amino acid sequence of SEQ ID NO: 174.

10. The antibody of claim 1, wherein the antibody is an IgG antibody which comprises a heavy chain polypeptide comprising an amino acid sequence of SEQ ID NO: 176, and a light chain polypeptide comprising an amino acid sequence of SEQ ID NO: 178.

11. The antibody of claim 1, wherein the antibody is an antibody fragment Fab which comprises a heavy chain polypeptide comprising an amino acid sequence of SEQ ID NO: 180, and a light chain polypeptide comprising an amino acid sequence of SEQ ID NO: 178.

12. A diagnostic kit for detecting cancer, the diagnostic kit comprising an antibody of claim 1.

13. The diagnostic kit of claim 12, wherein the cancer is selected from the group consisting of breast cancer, large intestinal cancer, lung cancer, small cell lung cancer, stomach cancer, liver cancer, blood cancer, bone cancer, pancreatic cancer, skin cancer, head or neck cancer, cutaneous or intraocular melanoma, uterine sarcoma, ovarian cancer, rectal cancer, anal cancer, colon cancer, fallopian tube carcinoma, endometrial carcinoma, cervical cancer, vulval cancer, vaginal carcinoma, Hodgkin's disease, esophageal cancer, small intestine cancer, endocrine cancer, thyroid cancer, parathyroid cancer, adrenal cancer, soft tissue tumor, urethral cancer, penile cancer, prostate cancer, bronchogenic cancer, nasopharyngeal cancer, laryngeal cancer, chronic or acute leukemia, lymphocytic lymphoma, bladder cancer, kidney cancer, ureter cancer, renal cell carcinoma, renal pelvic carcinoma, CNS tumor, primary CNS lymphoma, bone marrow tumor, brain stem nerve gliomas and pituitary adenoma.

* * * * *

SEQUENCE LISTING

```
<160> NUMBER OF SEQ ID NOS: 221

<210> SEQ ID NO 1
<211> LENGTH: 756
<212> TYPE: DNA
<213> ORGANISM: Artificial Sequence
<220> FEATURE:
<223> OTHER INFORMATION: AIMP2-DX2-320 amino acids

<400> SEQUENCE: 1
atgccgatgt accaggtaaa gccctatcac gggggcggcg cgcctctccg tgtggagctt       60
cccacctgca tgtaccggct ccccaacgtg cacggcagga gctacggccc agcgccgggc      120
gctggccacg tgcaggatta cggggcgctg aaagacatcg tgatcaacgc aaacccggcc      180
```

```
tccccctcccc tctccctgct tgtgctgcac aggctgctct gtgagcactt cagggtcctg    240
tccacggtgc acacgcactc ctcggtcaag agcgtgcctg aaaaccttct caagtgcttt    300
ggagaacaga ataaaaaaca gccccgccaa gactatcagc tgggattcac tttaatttgg    360
aagaatgtgc cgaagacgca gatgaaattc agcatccaga cgatgtgccc catcgaaggc    420
gaagggaaca ttgcacgttt cttgttctct ctgtttggcc agaagcataa tgctgtcaac    480 gcaacccctta tagatagctg ggtagatatt gcgattttc agttaaaaga gggaagcagt    540
aaagaaaaag ccgctgtttt ccgctccatg aactctgctc ttgggaagag cccttggctc    600
gctgggaatg aactcaccgt agcagacgtg gtgctgtggt ctgtactcca gcagatcgga    660
ggctgcagtg tgacagtgcc agccaatgtg cagaggtgga tgaggtcttg tgaaaacctg    720
gctcctttta acacggccct caagctcctt aagtga                               756
```

```
<210> SEQ ID NO 2
<211> LENGTH: 251
<212> TYPE: PRT
<213> ORGANISM: Artificial Sequence
<220> FEATURE:
<223> OTHER INFORMATION: AIMP2-DX2-320 amino acids

<400> SEQUENCE: 2
```

```
Met Pro Met Tyr Gln Val Lys Pro Tyr His Gly Gly Gly Ala Pro Leu
  1               5                  10                  15

Arg Val Glu Leu Pro Thr Cys Met Tyr Arg Leu Pro Asn Val His Gly
             20                  25                  30

Arg Ser Tyr Gly Pro Ala Pro Gly Ala Gly His Val Gln Asp Tyr Gly
         35                  40                  45

Ala Leu Lys Asp Ile Val Ile Asn Ala Asn Pro Ala Ser Pro Pro Leu
     50                  55                  60

Ser Leu Leu Val Leu His Arg Leu Leu Cys Glu His Phe Arg Val Leu
 65                  70                  75                  80

Ser Thr Val His Thr His Ser Ser Val Lys Ser Val Pro Glu Asn Leu
                 85                  90                  95

Leu Lys Cys Phe Gly Glu Gln Asn Lys Lys Gln Pro Arg Gln Asp Tyr
            100                 105                 110

Gln Leu Gly Phe Thr Leu Ile Trp Lys Asn Val Pro Lys Thr Gln Met
        115                 120                 125

Lys Phe Ser Ile Gln Thr Met Cys Pro Ile Glu Gly Glu Gly Asn Ile
    130                 135                 140

Ala Arg Phe Leu Phe Ser Leu Phe Gly Gln Lys His Asn Ala Val Asn
145                 150                 155                 160

Ala Thr Leu Ile Asp Ser Trp Val Asp Ile Ala Ile Phe Gln Leu Lys
                165                 170                 175

Glu Gly Ser Ser Lys Glu Lys Ala Ala Val Phe Arg Ser Met Asn Ser
            180                 185                 190

Ala Leu Gly Lys Ser Pro Trp Leu Ala Gly Asn Glu Leu Thr Val Ala
        195                 200                 205

Asp Val Val Leu Trp Ser Val Leu Gln Gln Ile Gly Gly Cys Ser Val
    210                 215                 220

Thr Val Pro Ala Asn Val Gln Arg Trp Met Arg Ser Cys Glu Asn Leu
225                 230                 235                 240

Ala Pro Phe Asn Thr Ala Leu Lys Leu Leu Lys
                245                 250
```

```
<210> SEQ ID NO 3
<211> LENGTH: 20
<212> TYPE: DNA
<213> ORGANISM: Artificial Sequence
<220> FEATURE:
<223> OTHER INFORMATION: forward primer for exon 3-4

<400> SEQUENCE: 3
agtgctttgg agaacagaat                                              20

<210> SEQ ID NO 4
<211> LENGTH: 20
<212> TYPE: DNA
<213> ORGANISM: Artificial Sequence
<220> FEATURE:
<223> OTHER INFORMATION: reverse primer for exon 3-4

<400> SEQUENCE: 4
aagagcagag ttcatggagc                                              20

<210> SEQ ID NO 5
<211> LENGTH: 20
<212> TYPE: DNA
<213> ORGANISM: Artificial Sequence
<220> FEATURE:
<223> OTHER INFORMATION: forward primer for exon 1-3

<400> SEQUENCE: 5
tctgacggtt tctgagcgtt                                              20

<210> SEQ ID NO 6
<211> LENGTH: 20
<212> TYPE: DNA
<213> ORGANISM: Artificial Sequence
<220> FEATURE:
<223> OTHER INFORMATION: reverse primer for exon 1-3

<400> SEQUENCE: 6
aagtgaatcc cagctgatag                                              20

<210> SEQ ID NO 7
<211> LENGTH: 21
<212> TYPE: DNA
<213> ORGANISM: Artificial Sequence
<220> FEATURE:
<223> OTHER INFORMATION: forward primer for AIMP2-DX2

<400> SEQUENCE: 7
tgctttggtt ctgccatgcc g                                            21

<210> SEQ ID NO 8
<211> LENGTH: 21
<212> TYPE: DNA
<213> ORGANISM: Artificial Sequence
<220> FEATURE:
<223> OTHER INFORMATION: reverse primer for AIMP2-DX2

<400> SEQUENCE: 8
cgtaatcctg cacgtggcca g                                            21

<210> SEQ ID NO 9
<211> LENGTH: 54
<212> TYPE: DNA
<213> ORGANISM: Artificial Sequence
<220> FEATURE:
<223> OTHER INFORMATION: si-AIMP2-DX2 #3 coding nucleic acid sequence 1
```

<400> SEQUENCE: 9
tcgaggccac gtgcaggtta cgggagtagg ccgtaatcct gcacgtggcc tttt         54

<210> SEQ ID NO 10
<211> LENGTH: 55
<212> TYPE: DNA
<213> ORGANISM: Artificial Sequence
<220> FEATURE:
<223> OTHER INFORMATION: si-AIMP2-DX2 #3 coding nucleic acid sequence 2

<400> SEQUENCE: 10
ctagaaaagg ccacgtgcag gattacggca gactcccgta atcctgcacg tggcc        55

<210> SEQ ID NO 11
<211> LENGTH: 58
<212> TYPE: DNA
<213> ORGANISM: Artificial Sequence
<220> FEATURE:
<223> OTHER INFORMATION: si-AIMP2-DX2 #4 coding nucleic acid sequence 1

<400> SEQUENCE: 11
tcgagctggc cacgtgcagg attacgagta ctggtaatcc tgcacgtggc cagcttttt   58

<210> SEQ ID NO 12
<211> LENGTH: 58
<212> TYPE: DNA
<213> ORGANISM: Artificial Sequence
<220> FEATURE:
<223> OTHER INFORMATION: si-AIMP2-DX2 #4 coding nucleic acid sequence 2

<400> SEQUENCE: 12
ctagaaaagc tggccacgtg caggattacc agtactcgta atcctgcacg tggccagc    58

<210> SEQ ID NO 13
<211> LENGTH: 56
<212> TYPE: DNA
<213> ORGANISM: Artificial Sequence
<220> FEATURE:
<223> OTHER INFORMATION: si-AIMP2-DX2 #5 coding nucleic acid sequence 1

<400> SEQUENCE: 13
tcgacacgtg caggattacg gggcgagtac tggccccgta atcctgcacg tgtttt       56

<210> SEQ ID NO 14
<211> LENGTH: 56
<212> TYPE: DNA
<213> ORGANISM: Artificial Sequence
<220> FEATURE:
<223> OTHER INFORMATION: si-AIMP2-DX2 #5 coding nucleic acid sequence 2

<400> SEQUENCE: 14
ctagaaaaca cgtgcaggat tacggggcca gtactcgccc cgtaatcctg cacgtg       56

<210> SEQ ID NO 15
<211> LENGTH: 15
<212> TYPE: DNA
<213> ORGANISM: Artificial Sequence
<220> FEATURE:
<223> OTHER INFORMATION: AIMP2-specific RT primer

<400> SEQUENCE: 15
cagcaccacg tctgc                                                    15

<210> SEQ ID NO 16
<211> LENGTH: 729

```
<212> TYPE: DNA
<213> ORGANISM: Artificial Sequence
<220> FEATURE:
<223> OTHER INFORMATION: CDS of AIMP2-DX2-312 amino acid

<400> SEQUENCE: 16
atgccgatgt accaggtaaa gccctatcac gggggcggcg cgcctctccg tgtggagctt      60
cccacctgca tgtaccggct ccccaacgtg cacggcagga gctacggccc agcgccgggc     120
gctggccacg tgcaggatta cggggcgctg aaagacatcg tgatcaacgc aaacccggcc     180
tcccctcccc tctccctgct tgtgctgcac aggctgctct gtgagcactt cagggtcctg     240
tccacggtgc acacgcactc ctcggtcaag agcgtgcctg aaaaccttct caagtgcttt     300
ggagaacaga ataaaaaaca gccccgccaa gactatcagc tgggattcac tttaatttgg     360
aagaatgtgc cgaagacgca gatgaaattc agcatccaga cgatgtgccc catcgaaggc     420
gaagggaaca ttgcacgttt cttgttctct ctgtttggcc agaagcataa tgctgtcaac     480
gcaaccctta tagatagctg ggtagatatt gcgattttc agttaaaaga gggaagcagt     540
aaagaaaaag ccgctgtttt ccgctccatg aactctgctc ttgggaagag cccttggctc     600
gctgggaatg aactcaccgt agcagacgtg gtgctgtggt ctgtactcca gcagatcgga     660
ggctgcagtg tgacagtgcc agccaatgtg cagaggtgga tgaggtcttg tgaaaacctg     720
gctccttttt                                                             729

<210> SEQ ID NO 17
<211> LENGTH: 243
<212> TYPE: PRT
<213> ORGANISM: Artificial Sequence
<220> FEATURE:
<223> OTHER INFORMATION: AIMP2-DX2-312 amino acid

<400> SEQUENCE: 17

Met Pro Met Tyr Gln Val Lys Pro Tyr His Gly Gly Ala Pro Leu
  1               5                  10                  15

Arg Val Glu Leu Pro Thr Cys Met Tyr Arg Leu Pro Asn Val His Gly
             20                  25                  30

Arg Ser Tyr Gly Pro Ala Pro Gly Ala Gly His Val Gln Asp Tyr Gly
         35                  40                  45

Ala Leu Lys Asp Ile Val Ile Asn Ala Asn Pro Ala Ser Pro Pro Leu
     50                  55                  60

Ser Leu Leu Val Leu His Arg Leu Leu Cys Glu His Phe Arg Val Leu
 65                  70                  75                  80

Ser Thr Val His Thr His Ser Ser Val Lys Ser Val Pro Glu Asn Leu
                 85                  90                  95

Leu Lys Cys Phe Gly Glu Gln Asn Lys Lys Gln Pro Arg Gln Asp Tyr
            100                 105                 110

Gln Leu Gly Phe Thr Leu Ile Trp Lys Asn Val Pro Lys Thr Gln Met
        115                 120                 125

Lys Phe Ser Ile Gln Thr Met Cys Pro Ile Glu Gly Glu Gly Asn Ile
    130                 135                 140

Ala Arg Phe Leu Phe Ser Leu Phe Gly Gln Lys His Asn Ala Val Asn
145                 150                 155                 160

Ala Thr Leu Ile Asp Ser Trp Val Asp Ile Ala Ile Phe Gln Leu Lys
                165                 170                 175

Glu Gly Ser Ser Lys Glu Lys Ala Ala Val Phe Arg Ser Met Asn Ser
            180                 185                 190
```

Ala Leu Gly Lys Ser Pro Trp Leu Ala Gly Asn Glu Leu Thr Val Ala
            195                 200                 205

Asp Val Val Leu Trp Ser Val Leu Gln Gln Ile Gly Gly Cys Ser Val
        210                 215                 220

Thr Val Pro Ala Asn Val Gln Arg Trp Met Arg Ser Cys Glu Asn Leu
225                 230                 235                 240

Ala Pro Phe

<210> SEQ ID NO 18
<211> LENGTH: 58
<212> TYPE: DNA
<213> ORGANISM: Artificial Sequence
<220> FEATURE:
<223> OTHER INFORMATION: si-RNA target sequence

<400> SEQUENCE: 18
tcgagctggc cacgtgcagg attacgagta ctggtaatcc tgcacgtggc cagctttt       58

<210> SEQ ID NO 19
<211> LENGTH: 25
<212> TYPE: DNA
<213> ORGANISM: Artificial Sequence
<220> FEATURE:
<223> OTHER INFORMATION: AIMP2-F forward Quantitative PCR primer

<400> SEQUENCE: 19
ctccaagatg attcaaacac cagat                                           25

<210> SEQ ID NO 20
<211> LENGTH: 20
<212> TYPE: DNA
<213> ORGANISM: Artificial Sequence
<220> FEATURE:
<223> OTHER INFORMATION: AIMP2-F reverse Quantitative PCR primer

<400> SEQUENCE: 20
ccgtaatcct tcccaagcac                                                 20

<210> SEQ ID NO 21
<211> LENGTH: 18
<212> TYPE: DNA
<213> ORGANISM: Artificial Sequence
<220> FEATURE:
<223> OTHER INFORMATION: AIMP2-DX2 forward Quantitative PCR primer

<400> SEQUENCE: 21
gccacgtgca ggattacg                                                   18

<210> SEQ ID NO 22
<211> LENGTH: 18
<212> TYPE: DNA
<213> ORGANISM: Artificial Sequence
<220> FEATURE:
<223> OTHER INFORMATION: AIMP2-DX2 reverse Quantitative PCR primer

<400> SEQUENCE: 22
tgcaccgtgg acaggacc                                                   18

<210> SEQ ID NO 23
<211> LENGTH: 26
<212> TYPE: DNA
<213> ORGANISM: Artificial Sequence
<220> FEATURE:
<223> OTHER INFORMATION: PAPOLA forward Quantitative PCR primer

```
<400> SEQUENCE: 23 aaacttttg aagctccaaa cttctt                                         26

<210> SEQ ID NO 24
<211> LENGTH: 18
<212> TYPE: DNA
<213> ORGANISM: Artificial Sequence
<220> FEATURE:
<223> OTHER INFORMATION: PAPOLA reverse Quantitative PCR primer

<400> SEQUENCE: 24
caccaagccc acccattc                                                 18

<210> SEQ ID NO 25
<211> LENGTH: 25
<212> TYPE: DNA
<213> ORGANISM: Artificial Sequence
<220> FEATURE:
<223> OTHER INFORMATION: siRNA of AIMP2-F

<400> SEQUENCE: 25
agucuaaccu gucucugcaa gcucu                                         25

<210> SEQ ID NO 26
<211> LENGTH: 58
<212> TYPE: DNA
<213> ORGANISM: Artificial Sequence
<220> FEATURE:
<223> OTHER INFORMATION: shRNA sequence of AIMP2-DX2

<400> SEQUENCE: 26
tcgagctggc cacgtgcagg attacgagta ctggtaatcc tgcacgtggc cagctttt     58

<210> SEQ ID NO 27
<211> LENGTH: 19
<212> TYPE: RNA
<213> ORGANISM: Artificial Sequence
<220> FEATURE:
<223> OTHER INFORMATION: AIMP2-DX2 siRNA 19mer #1

<400> SEQUENCE: 27
cuggccacgu gcaggauua                                                19

<210> SEQ ID NO 28
<211> LENGTH: 19
<212> TYPE: RNA
<213> ORGANISM: Artificial Sequence
<220> FEATURE:
<223> OTHER INFORMATION: AIMP2-DX2 siRNA of 19mer #2

<400> SEQUENCE: 28
uggccacgug caggauuac                                                19

<210> SEQ ID NO 29
<211> LENGTH: 19
<212> TYPE: RNA
<213> ORGANISM: Artificial Sequence
<220> FEATURE:
<223> OTHER INFORMATION: AIMP2-DX2 siRNA of 19mer #3

<400> SEQUENCE: 29
ggccacgugc aggauuacg                                                19

<210> SEQ ID NO 30
<211> LENGTH: 19
```

```
<212> TYPE: RNA
<213> ORGANISM: Artificial Sequence
<220> FEATURE:
<223> OTHER INFORMATION: 19mer of AIMP2-DX2 siRNA #4

<400> SEQUENCE: 30
gccacgugca ggauuacgg                                              19

<210> SEQ ID NO 31
<211> LENGTH: 19
<212> TYPE: RNA
<213> ORGANISM: Artificial Sequence
<220> FEATURE:
<223> OTHER INFORMATION: 19mer of AIMP2-DX2 siRNA #5

<400> SEQUENCE: 31
ccacgugcag gauuacggg                                              19

<210> SEQ ID NO 32
<211> LENGTH: 19
<212> TYPE: RNA
<213> ORGANISM: Artificial Sequence
<220> FEATURE:
<223> OTHER INFORMATION: 19mer of AIMP2-DX2 siRNA #6

<400> SEQUENCE: 32
cacgugcagg auuacgggg                                              19

<210> SEQ ID NO 33
<211> LENGTH: 19
<212> TYPE: RNA
<213> ORGANISM: Artificial Sequence
<220> FEATURE:
<223> OTHER INFORMATION: 19mer of AIMP2-DX2 siRNA #7

<400> SEQUENCE: 33
acgugcagga uuacggggc                                              19

<210> SEQ ID NO 34
<211> LENGTH: 19
<212> TYPE: RNA
<213> ORGANISM: Artificial Sequence
<220> FEATURE:
<223> OTHER INFORMATION: 19mer of AIMP2-DX2 siRNA #8

<400> SEQUENCE: 34
cgugcaggau uacggggcg                                              19

<210> SEQ ID NO 35
<211> LENGTH: 19
<212> TYPE: RNA
<213> ORGANISM: Artificial Sequence
<220> FEATURE:
<223> OTHER INFORMATION: 19mer of AIMP2-DX2 siRNA #8

<400> SEQUENCE: 35
cgugcaggau uacggggcg                                              19

<210> SEQ ID NO 36
<211> LENGTH: 19
<212> TYPE: RNA
<213> ORGANISM: Artificial Sequence
<220> FEATURE:
<223> OTHER INFORMATION: 19mer of AIMP2-DX2 siRNA #9

<400> SEQUENCE: 36
```
gugcaggauu acggggcgc                                              19

<210> SEQ ID NO 37
<211> LENGTH: 19
<212> TYPE: RNA
<213> ORGANISM: Artificial Sequence
<220> FEATURE:
<223> OTHER INFORMATION: 19mer of AIMP2-DX2 siRNA #10

<400> SEQUENCE: 37
ugcaggauua cggggcgcu                                              19

<210> SEQ ID NO 38
<211> LENGTH: 20
<212> TYPE: RNA
<213> ORGANISM: Artificial Sequence
<220> FEATURE:
<223> OTHER INFORMATION: 20mer of AIMP2-DX2 siRNA #1

<400> SEQUENCE: 38
gcuggccacg ugcaggauua                                             20

<210> SEQ ID NO 39
<211> LENGTH: 20
<212> TYPE: RNA
<213> ORGANISM: Artificial Sequence
<220> FEATURE:
<223> OTHER INFORMATION: 20mer of AIMP2-DX2 siRNA #2

<400> SEQUENCE: 39
cuggccacgu gcaggauuac                                             20

<210> SEQ ID NO 40
<211> LENGTH: 20
<212> TYPE: RNA
<213> ORGANISM: Artificial Sequence
<220> FEATURE:
<223> OTHER INFORMATION: 20mer of AIMP2-DX2 siRNA #3

<400> SEQUENCE: 40
uggccacgug caggauuacg                                             20

<210> SEQ ID NO 41
<211> LENGTH: 20
<212> TYPE: RNA
<213> ORGANISM: Artificial Sequence
<220> FEATURE:
<223> OTHER INFORMATION: 20mer of AIMP2-DX2 siRNA #4

<400> SEQUENCE: 41
ggccacgugc aggauuacgg                                             20

<210> SEQ ID NO 42
<211> LENGTH: 20
<212> TYPE: RNA
<213> ORGANISM: Artificial Sequence
<220> FEATURE:
<223> OTHER INFORMATION: 20mer of AIMP2-DX2 siRNA #5

<400> SEQUENCE: 42
gccacgugca ggauuacggg                                             20

<210> SEQ ID NO 43
<211> LENGTH: 20
<212> TYPE: RNA
<213> ORGANISM: Artificial Sequence

```
<220> FEATURE:
<223> OTHER INFORMATION: 20mer of AIMP2-DX2 siRNA #6

<400> SEQUENCE: 43
ccacgugcag gauuacgggg                                                    20

<210> SEQ ID NO 44
<211> LENGTH: 20
<212> TYPE: RNA
<213> ORGANISM: Artificial Sequence
<220> FEATURE:
<223> OTHER INFORMATION: 20mer of AIMP2-DX2 siRNA #7

<400> SEQUENCE: 44
cacgugcagg auuacggggc                                                    20

<210> SEQ ID NO 45
<211> LENGTH: 20
<212> TYPE: RNA
<213> ORGANISM: Artificial Sequence
<220> FEATURE:
<223> OTHER INFORMATION: 20mer of AIMP2-DX2 siRNA #8

<400> SEQUENCE: 45
acgugcagga uuacggggcg                                                    20

<210> SEQ ID NO 46
<211> LENGTH: 20
<212> TYPE: RNA
<213> ORGANISM: Artificial Sequence
<220> FEATURE:
<223> OTHER INFORMATION: 20mer of AIMP2-DX2 siRNA #9

<400> SEQUENCE: 46
cgugcaggau uacggggcgc                                                    20

<210> SEQ ID NO 47
<211> LENGTH: 20
<212> TYPE: RNA
<213> ORGANISM: Artificial Sequence
<220> FEATURE:
<223> OTHER INFORMATION: 20mer of AIMP2-DX2 siRNA #10

<400> SEQUENCE: 47
gugcaggauu acggggcgcu                                                    20

<210> SEQ ID NO 48
<211> LENGTH: 20
<212> TYPE: RNA
<213> ORGANISM: Artificial Sequence
<220> FEATURE:
<223> OTHER INFORMATION: 20mer of AIMP2-DX2 siRNA #11

<400> SEQUENCE: 48
ugcaggauua cggggcgcug                                                    20

<210> SEQ ID NO 49
<211> LENGTH: 21
<212> TYPE: RNA
<213> ORGANISM: Artificial Sequence
<220> FEATURE:
<223> OTHER INFORMATION: 21mer of AIMP2-DX2 siRNA #1

<400> SEQUENCE: 49
cgcuggccac gugcaggauu a                                                  21
```

```
<210> SEQ ID NO 50
<211> LENGTH: 21
<212> TYPE: RNA
<213> ORGANISM: Artificial Sequence
<220> FEATURE:
<223> OTHER INFORMATION: 21mer of AIMP2-DX2 siRNA #2

<400> SEQUENCE: 50
gcuggccacg ugcaggauua c                                              21

<210> SEQ ID NO 51
<211> LENGTH: 21
<212> TYPE: RNA
<213> ORGANISM: Artificial Sequence
<220> FEATURE:
<223> OTHER INFORMATION: 21mer of AIMP2-DX2 siRNA #3

<400> SEQUENCE: 51
cuggccacgu gcaggauuac g                                              21

<210> SEQ ID NO 52
<211> LENGTH: 21
<212> TYPE: RNA
<213> ORGANISM: Artificial Sequence
<220> FEATURE:
<223> OTHER INFORMATION: 21mer of AIMP2-DX2 siRNA #4

<400> SEQUENCE: 52
uggccacgug caggauuacg g                                              21

<210> SEQ ID NO 53
<211> LENGTH: 21
<212> TYPE: RNA
<213> ORGANISM: Artificial Sequence
<220> FEATURE:
<223> OTHER INFORMATION: 21mer of AIMP2-DX2 siRNA #5

<400> SEQUENCE: 53
ggccacgugc aggauuacgg g                                              21

<210> SEQ ID NO 54
<211> LENGTH: 21
<212> TYPE: RNA
<213> ORGANISM: Artificial Sequence
<220> FEATURE:
<223> OTHER INFORMATION: 21mer of AIMP2-DX2 siRNA #6

<400> SEQUENCE: 54
gccacgugca ggauuacggg g                                              21

<210> SEQ ID NO 55
<211> LENGTH: 21
<212> TYPE: RNA
<213> ORGANISM: Artificial Sequence
<220> FEATURE:
<223> OTHER INFORMATION: 21mer of AIMP2-DX2 siRNA #7

<400> SEQUENCE: 55
ccacgugcag gauuacgggg c                                              21

<210> SEQ ID NO 56
<211> LENGTH: 21
<212> TYPE: RNA
<213> ORGANISM: Artificial Sequence
<220> FEATURE:
<223> OTHER INFORMATION: 21mer of AIMP2-DX2 siRNA #8
```

```
<400> SEQUENCE: 56
cacgugcagg auuacggggc g                                               21

<210> SEQ ID NO 57
<211> LENGTH: 21
<212> TYPE: RNA
<213> ORGANISM: Artificial Sequence
<220> FEATURE:
<223> OTHER INFORMATION: 21mer of AIMP2-DX2 siRNA #9

<400> SEQUENCE: 57
acgugcagga uuacggggcg c                                               21

<210> SEQ ID NO 58
<211> LENGTH: 21
<212> TYPE: RNA
<213> ORGANISM: Artificial Sequence
<220> FEATURE:
<223> OTHER INFORMATION: 21mer of AIMP2-DX2 siRNA #10

<400> SEQUENCE: 58
cgugcaggau uacggggcgc u                                               21

<210> SEQ ID NO 59
<211> LENGTH: 21
<212> TYPE: RNA
<213> ORGANISM: Artificial Sequence
<220> FEATURE:
<223> OTHER INFORMATION: 21mer of AIMP2-DX2 siRNA #11

<400> SEQUENCE: 59
gugcaggauu acggggcgcu g                                               21

<210> SEQ ID NO 60
<211> LENGTH: 21
<212> TYPE: RNA
<213> ORGANISM: Artificial Sequence
<220> FEATURE:
<223> OTHER INFORMATION: 21mer of AIMP2-DX2 siRNA #12

<400> SEQUENCE: 60
ugcaggauua cggggcgcug a                                               21

<210> SEQ ID NO 61
<211> LENGTH: 22
<212> TYPE: RNA
<213> ORGANISM: Artificial Sequence
<220> FEATURE:
<223> OTHER INFORMATION: 22mer of AIMP2-DX2 siRNA #1

<400> SEQUENCE: 61
gcgcuggcca cgugcaggau ua                                              22

<210> SEQ ID NO 62
<211> LENGTH: 22
<212> TYPE: RNA
<213> ORGANISM: Artificial Sequence
<220> FEATURE:
<223> OTHER INFORMATION: 22mer of AIMP2-DX2 siRNA #2

<400> SEQUENCE: 62
cgcuggccac gugcaggauu ac                                              22

<210> SEQ ID NO 63
```

```
<211> LENGTH: 22
<212> TYPE: RNA
<213> ORGANISM: Artificial Sequence
<220> FEATURE:
<223> OTHER INFORMATION: 22mer of AIMP2-DX2 siRNA #3

<400> SEQUENCE: 63
gcuggccacg ugcaggauua cg                                              22

<210> SEQ ID NO 64
<211> LENGTH: 22
<212> TYPE: RNA
<213> ORGANISM: Artificial Sequence
<220> FEATURE:
<223> OTHER INFORMATION: 22mer of AIMP2-DX2 siRNA #4

<400> SEQUENCE: 64
cuggccacgu gcaggauuac gg                                              22

<210> SEQ ID NO 65
<211> LENGTH: 22
<212> TYPE: RNA
<213> ORGANISM: Artificial Sequence
<220> FEATURE:
<223> OTHER INFORMATION: 22mer of AIMP2-DX2 siRNA #5

<400> SEQUENCE: 65
uggccacgug caggauuacg gg                                              22

<210> SEQ ID NO 66
<211> LENGTH: 22
<212> TYPE: RNA
<213> ORGANISM: Artificial Sequence
<220> FEATURE:
<223> OTHER INFORMATION: 22mer of AIMP2-DX2 siRNA #6

<400> SEQUENCE: 66
ggccacgugc aggauuacgg gg                                              22

<210> SEQ ID NO 67
<211> LENGTH: 22
<212> TYPE: RNA
<213> ORGANISM: Artificial Sequence
<220> FEATURE:
<223> OTHER INFORMATION: 22mer of AIMP2-DX2 siRNA #7

<400> SEQUENCE: 67
gccacgugca ggauuacggg gc                                              22

<210> SEQ ID NO 68
<211> LENGTH: 22
<212> TYPE: RNA
<213> ORGANISM: Artificial Sequence
<220> FEATURE:
<223> OTHER INFORMATION: 22mer of AIMP2-DX2 siRNA #8

<400> SEQUENCE: 68
ccacgugcag gauuacgggg cg                                              22

<210> SEQ ID NO 69
<211> LENGTH: 22
<212> TYPE: RNA
<213> ORGANISM: Artificial Sequence
<220> FEATURE:
<223> OTHER INFORMATION: 22mer of AIMP2-DX2 siRNA #9

<400> SEQUENCE: 69
```

```
cacgugcagg auuacggggc gc                                              22

<210> SEQ ID NO 70
<211> LENGTH: 22
<212> TYPE: RNA
<213> ORGANISM: Artificial Sequence
<220> FEATURE:
<223> OTHER INFORMATION: 22mer of AIMP2-DX2 siRNA #10

<400> SEQUENCE: 70
acgugcagga uuacggggcg cu                                              22

<210> SEQ ID NO 71
<211> LENGTH: 22
<212> TYPE: RNA
<213> ORGANISM: Artificial Sequence
<220> FEATURE:
<223> OTHER INFORMATION: 22mer of AIMP2-DX2 siRNA #10

<400> SEQUENCE: 71
acgugcagga uuacggggcg cu                                              22

<210> SEQ ID NO 72
<211> LENGTH: 22
<212> TYPE: RNA
<213> ORGANISM: Artificial Sequence
<220> FEATURE:
<223> OTHER INFORMATION: 22mer of AIMP2-DX2 siRNA #11

<400> SEQUENCE: 72
cgugcaggau uacggggcgc ug                                              22

<210> SEQ ID NO 73
<211> LENGTH: 22
<212> TYPE: RNA
<213> ORGANISM: Artificial Sequence
<220> FEATURE:
<223> OTHER INFORMATION: 22mer of AIMP2-DX2 siRNA #12

<400> SEQUENCE: 73
gugcaggauu acggggcgcu ga                                              22

<210> SEQ ID NO 74
<211> LENGTH: 22
<212> TYPE: RNA
<213> ORGANISM: Artificial Sequence
<220> FEATURE:
<223> OTHER INFORMATION: 22mer of AIMP2-DX2 siRNA #13

<400> SEQUENCE: 74
ugcaggauua cggggcgcug aa                                              22

<210> SEQ ID NO 75
<211> LENGTH: 23
<212> TYPE: RNA
<213> ORGANISM: Artificial Sequence
<220> FEATURE:
<223> OTHER INFORMATION: 23mer of AIMP2-DX2 siRNA #1

<400> SEQUENCE: 75
ggcgcuggcc acgugcagga uua                                             23

<210> SEQ ID NO 76
<211> LENGTH: 23
<212> TYPE: RNA
```

```
<213> ORGANISM: Artificial Sequence
<220> FEATURE:
<223> OTHER INFORMATION: 23mer of AIMP2-DX2 siRNA #2

<400> SEQUENCE: 76
gcgcuggcca cgugcaggau uac                                              23

<210> SEQ ID NO 77
<211> LENGTH: 23
<212> TYPE: RNA
<213> ORGANISM: Artificial Sequence
<220> FEATURE:
<223> OTHER INFORMATION: 23mer of AIMP2-DX2 siRNA #3

<400> SEQUENCE: 77
cgcuggccac gugcaggauu acg                                              23

<210> SEQ ID NO 78
<211> LENGTH: 23
<212> TYPE: RNA
<213> ORGANISM: Artificial Sequence
<220> FEATURE:
<223> OTHER INFORMATION: 23mer of AIMP2-DX2 siRNA #4

<400> SEQUENCE: 78
gcuggccacg ugcaggauua cgg                                              23

<210> SEQ ID NO 79
<211> LENGTH: 23
<212> TYPE: RNA
<213> ORGANISM: Artificial Sequence
<220> FEATURE:
<223> OTHER INFORMATION: 23mer of AIMP2-DX2 siRNA #5

<400> SEQUENCE: 79
cuggccacgu gcaggauuac ggg                                              23

<210> SEQ ID NO 80
<211> LENGTH: 23
<212> TYPE: RNA
<213> ORGANISM: Artificial Sequence
<220> FEATURE:
<223> OTHER INFORMATION: 23mer of AIMP2-DX2 siRNA #6

<400> SEQUENCE: 80
uggccacgug caggauuacg ggg                                              23

<210> SEQ ID NO 81
<211> LENGTH: 23
<212> TYPE: RNA
<213> ORGANISM: Artificial Sequence
<220> FEATURE:
<223> OTHER INFORMATION: 23mer of AIMP2-DX2 siRNA #7

<400> SEQUENCE: 81
ggccacgugc aggauuacgg ggc                                              23

<210> SEQ ID NO 82
<211> LENGTH: 23
<212> TYPE: RNA
<213> ORGANISM: Artificial Sequence
<220> FEATURE:
<223> OTHER INFORMATION: 23mer of AIMP2-DX2 siRNA #8

<400> SEQUENCE: 82
gccacgugca ggauuacggg gcg                                              23
```

<210> SEQ ID NO 83
<211> LENGTH: 23
<212> TYPE: RNA
<213> ORGANISM: Artificial Sequence
<220> FEATURE:
<223> OTHER INFORMATION: 23mer of AIMP2-DX2 siRNA #9

<400> SEQUENCE: 83
ccacgugcag gauuacgggg cgc         23

<210> SEQ ID NO 84
<211> LENGTH: 23
<212> TYPE: RNA
<213> ORGANISM: Artificial Sequence
<220> FEATURE:
<223> OTHER INFORMATION: 23mer of AIMP2-DX2 siRNA #10

<400> SEQUENCE: 84
cacgugcagg auuacggggc gcu         23

<210> SEQ ID NO 85
<211> LENGTH: 23
<212> TYPE: RNA
<213> ORGANISM: Artificial Sequence
<220> FEATURE:
<223> OTHER INFORMATION: 23mer of AIMP2-DX2 siRNA #11

<400> SEQUENCE: 85
acgugcagga uuacggggcg cug         23

<210> SEQ ID NO 86
<211> LENGTH: 23
<212> TYPE: RNA
<213> ORGANISM: Artificial Sequence
<220> FEATURE:
<223> OTHER INFORMATION: 23mer of AIMP2-DX2 siRNA #12

<400> SEQUENCE: 86
cgugcaggau uacggggcgc uga         23

<210> SEQ ID NO 87
<211> LENGTH: 23
<212> TYPE: RNA
<213> ORGANISM: Artificial Sequence
<220> FEATURE:
<223> OTHER INFORMATION: 23mer of AIMP2-DX2 siRNA #13

<400> SEQUENCE: 87
gugcaggauu acggggcgcu gaa         23

<210> SEQ ID NO 88
<211> LENGTH: 23
<212> TYPE: RNA
<213> ORGANISM: Artificial Sequence
<220> FEATURE:
<223> OTHER INFORMATION: 23mer of AIMP2-DX2 siRNA #14

<400> SEQUENCE: 88
ugcaggauua cggggcgcug aaa         23

<210> SEQ ID NO 89
<211> LENGTH: 24
<212> TYPE: RNA
<213> ORGANISM: Artificial Sequence
<220> FEATURE:

<223> OTHER INFORMATION: 24mer of AIMP2-DX2 siRNA #1

<400> SEQUENCE: 89
gggcgcuggc cacgugcagg auua                                          24

<210> SEQ ID NO 90
<211> LENGTH: 24
<212> TYPE: RNA
<213> ORGANISM: Artificial Sequence
<220> FEATURE:
<223> OTHER INFORMATION: 24mer of AIMP2-DX2 siRNA #2

<400> SEQUENCE: 90
ggcgcuggcc acgugcagga uuac                                          24

<210> SEQ ID NO 91
<211> LENGTH: 24
<212> TYPE: RNA
<213> ORGANISM: Artificial Sequence
<220> FEATURE:
<223> OTHER INFORMATION: 24mer of AIMP2-DX2 siRNA #3

<400> SEQUENCE: 91
gcgcuggcca cgugcaggau uacg                                          24

<210> SEQ ID NO 92
<211> LENGTH: 24
<212> TYPE: RNA
<213> ORGANISM: Artificial Sequence
<220> FEATURE:
<223> OTHER INFORMATION: 24mer of AIMP2-DX2 siRNA #4

<400> SEQUENCE: 92
cgcuggccac gugcaggauu acgg                                          24

<210> SEQ ID NO 93
<211> LENGTH: 24
<212> TYPE: RNA
<213> ORGANISM: Artificial Sequence
<220> FEATURE:
<223> OTHER INFORMATION: 24mer of AIMP2-DX2 siRNA #5

<400> SEQUENCE: 93
gcuggccacg ugcaggauua cggg                                          24

<210> SEQ ID NO 94
<211> LENGTH: 24
<212> TYPE: RNA
<213> ORGANISM: Artificial Sequence
<220> FEATURE:
<223> OTHER INFORMATION: 24mer of AIMP2-DX2 siRNA #6

<400> SEQUENCE: 94
cuggccacgu gcaggauuac gggg                                          24

<210> SEQ ID NO 95
<211> LENGTH: 24
<212> TYPE: RNA
<213> ORGANISM: Artificial Sequence
<220> FEATURE:
<223> OTHER INFORMATION: 24mer of AIMP2-DX2 siRNA #7

<400> SEQUENCE: 95
uggccacgug caggauuacg ggc                                           24

-continued

<210> SEQ ID NO 96
<211> LENGTH: 24
<212> TYPE: RNA
<213> ORGANISM: Artificial Sequence
<220> FEATURE:
<223> OTHER INFORMATION: 24mer of AIMP2-DX2 siRNA #8

<400> SEQUENCE: 96
ggccacgugc aggauuacgg ggcg                                          24

<210> SEQ ID NO 97
<211> LENGTH: 24
<212> TYPE: RNA
<213> ORGANISM: Artificial Sequence
<220> FEATURE:
<223> OTHER INFORMATION: 24mer of AIMP2-DX2 siRNA #9

<400> SEQUENCE: 97
gccacgugca ggauuacggg gcgc                                          24

<210> SEQ ID NO 98
<211> LENGTH: 24
<212> TYPE: RNA
<213> ORGANISM: Artificial Sequence
<220> FEATURE:
<223> OTHER INFORMATION: 24mer of AIMP2-DX2 siRNA #10

<400> SEQUENCE: 98
ccacgugcag gauuacgggg cgcu                                          24

<210> SEQ ID NO 99
<211> LENGTH: 24
<212> TYPE: RNA
<213> ORGANISM: Artificial Sequence
<220> FEATURE:
<223> OTHER INFORMATION: 24mer of AIMP2-DX2 siRNA #11

<400> SEQUENCE: 99
cacgugcagg auuacggggc gcug                                          24

<210> SEQ ID NO 100
<211> LENGTH: 24
<212> TYPE: RNA
<213> ORGANISM: Artificial Sequence
<220> FEATURE:
<223> OTHER INFORMATION: 24mer of AIMP2-DX2 siRNA #12

<400> SEQUENCE: 100
acgugcagga uuacggggcg cuga                                          24

<210> SEQ ID NO 101
<211> LENGTH: 24
<212> TYPE: RNA
<213> ORGANISM: Artificial Sequence
<220> FEATURE:
<223> OTHER INFORMATION: 24mer of AIMP2-DX2 siRNA #13

<400> SEQUENCE: 101
cgugcaggau uacggggcgc ugaa                                          24

<210> SEQ ID NO 102
<211> LENGTH: 24
<212> TYPE: RNA
<213> ORGANISM: Artificial Sequence
<220> FEATURE:
<223> OTHER INFORMATION: 24mer of AIMP2-DX2 siRNA #14

```
<400> SEQUENCE: 102
gugcaggauu acggggcgcu gaaa                                          24

<210> SEQ ID NO 103
<211> LENGTH: 24
<212> TYPE: RNA
<213> ORGANISM: Artificial Sequence
<220> FEATURE:
<223> OTHER INFORMATION: 24mer of AIMP2-DX2 siRNA #15

<400> SEQUENCE: 103
ugcaggauua cggggcgcug aaag                                          24

<210> SEQ ID NO 104
<211> LENGTH: 25
<212> TYPE: RNA
<213> ORGANISM: Artificial Sequence
<220> FEATURE:
<223> OTHER INFORMATION: 25mer of AIMP2-DX2 siRNA #1

<400> SEQUENCE: 104
cgggcgcugg ccacgugcag gauua                                         25

<210> SEQ ID NO 105
<211> LENGTH: 25
<212> TYPE: RNA
<213> ORGANISM: Artificial Sequence
<220> FEATURE:
<223> OTHER INFORMATION: 25mer of AIMP2-DX2 siRNA #2

<400> SEQUENCE: 105
gggcgcuggc cacgugcagg auuac                                         25

<210> SEQ ID NO 106
<211> LENGTH: 25
<212> TYPE: RNA
<213> ORGANISM: Artificial Sequence
<220> FEATURE:
<223> OTHER INFORMATION: 25mer of AIMP2-DX2 siRNA #3

<400> SEQUENCE: 106
ggcgcuggcc acgugcagga uuacg                                         25

<210> SEQ ID NO 107
<211> LENGTH: 25
<212> TYPE: RNA
<213> ORGANISM: Artificial Sequence
<220> FEATURE:
<223> OTHER INFORMATION: 25mer of AIMP2-DX2 siRNA #4

<400> SEQUENCE: 107
gcgcuggcca cgugcaggau uacgg                                         25

<210> SEQ ID NO 108
<211> LENGTH: 25
<212> TYPE: RNA
<213> ORGANISM: Artificial Sequence
<220> FEATURE:
<223> OTHER INFORMATION: 25mer of AIMP2-DX2 siRNA #5

<400> SEQUENCE: 108
cgcuggccac gugcaggauu acggg                                         25

<210> SEQ ID NO 109
<211> LENGTH: 25
```

```
<212> TYPE: RNA
<213> ORGANISM: Artificial Sequence
<220> FEATURE:
<223> OTHER INFORMATION: 25mer of AIMP2-DX2 siRNA #6

<400> SEQUENCE: 109
gcuggccacg ugcaggauua cgggg                                        25

<210> SEQ ID NO 110
<211> LENGTH: 25
<212> TYPE: RNA
<213> ORGANISM: Artificial Sequence
<220> FEATURE:
<223> OTHER INFORMATION: 25mer of AIMP2-DX2 siRNA #7

<400> SEQUENCE: 110
cuggccacgu gcaggauuac ggggc                                        25

<210> SEQ ID NO 111
<211> LENGTH: 25
<212> TYPE: RNA
<213> ORGANISM: Artificial Sequence
<220> FEATURE:
<223> OTHER INFORMATION: 25mer of AIMP2-DX2 siRNA #8

<400> SEQUENCE: 111
uggccacgug caggauuacg ggcg                                         25

<210> SEQ ID NO 112
<211> LENGTH: 25
<212> TYPE: RNA
<213> ORGANISM: Artificial Sequence
<220> FEATURE:
<223> OTHER INFORMATION: 25mer of AIMP2-DX2 siRNA #9

<400> SEQUENCE: 112
ggccacgugc aggauuacgg ggcgc                                        25

<210> SEQ ID NO 113
<211> LENGTH: 25
<212> TYPE: RNA
<213> ORGANISM: Artificial Sequence
<220> FEATURE:
<223> OTHER INFORMATION: 25mer of AIMP2-DX2 siRNA #10

<400> SEQUENCE: 113
gccacgugca ggauuacggg gcgcu                                        25

<210> SEQ ID NO 114
<211> LENGTH: 25
<212> TYPE: RNA
<213> ORGANISM: Artificial Sequence
<220> FEATURE:
<223> OTHER INFORMATION: 25mer of AIMP2-DX2 siRNA #11

<400> SEQUENCE: 114
ccacgugcag gauuacgggg cgcug                                        25

<210> SEQ ID NO 115
<211> LENGTH: 25
<212> TYPE: RNA
<213> ORGANISM: Artificial Sequence
<220> FEATURE:
<223> OTHER INFORMATION: 25mer of AIMP2-DX2 siRNA #12

<400> SEQUENCE: 115
```

-continued cacgugcagg auuacggggc gcuga                                              25

<210> SEQ ID NO 116
<211> LENGTH: 25
<212> TYPE: RNA
<213> ORGANISM: Artificial Sequence
<220> FEATURE:
<223> OTHER INFORMATION: 25mer of AIMP2-DX2 siRNA #13

<400> SEQUENCE: 116
acgugcagga uuacggggcg cugaa                                              25

<210> SEQ ID NO 117
<211> LENGTH: 25
<212> TYPE: RNA
<213> ORGANISM: Artificial Sequence
<220> FEATURE:
<223> OTHER INFORMATION: 25mer of AIMP2-DX2 siRNA #14

<400> SEQUENCE: 117
cgugcaggau uacggggcgc ugaaa                                              25

<210> SEQ ID NO 118
<211> LENGTH: 25
<212> TYPE: RNA
<213> ORGANISM: Artificial Sequence
<220> FEATURE:
<223> OTHER INFORMATION: 25mer of AIMP2-DX2 siRNA #15

<400> SEQUENCE: 118
gugcaggauu acggggcgcu gaaag                                              25

<210> SEQ ID NO 119
<211> LENGTH: 25
<212> TYPE: RNA
<213> ORGANISM: Artificial Sequence
<220> FEATURE:
<223> OTHER INFORMATION: 25mer of AIMP2-DX2 siRNA #16

<400> SEQUENCE: 119
ugcaggauua cggggcgcug aaaga                                              25

<210> SEQ ID NO 120
<211> LENGTH: 26
<212> TYPE: RNA
<213> ORGANISM: Artificial Sequence
<220> FEATURE:
<223> OTHER INFORMATION: 26mer of AIMP2-DX2 siRNA #1

<400> SEQUENCE: 120
ccgggcgcug gccacgugca ggauua                                             26

<210> SEQ ID NO 121
<211> LENGTH: 26
<212> TYPE: RNA
<213> ORGANISM: Artificial Sequence
<220> FEATURE:
<223> OTHER INFORMATION: 26mer of AIMP2-DX2 siRNA #2

<400> SEQUENCE: 121
cgggcgcugg ccacgugcag gauuac                                             26

<210> SEQ ID NO 122
<211> LENGTH: 26
<212> TYPE: RNA
<213> ORGANISM: Artificial Sequence

```
<220> FEATURE:
<223> OTHER INFORMATION: 26mer of AIMP2-DX2 siRNA #3

<400> SEQUENCE: 122
gggcgcuggc cacgugcagg auuacg                                              26

<210> SEQ ID NO 123
<211> LENGTH: 26
<212> TYPE: RNA
<213> ORGANISM: Artificial Sequence
<220> FEATURE:
<223> OTHER INFORMATION: 26mer of AIMP2-DX2 siRNA #4

<400> SEQUENCE: 123
ggcgcuggcc acgugcagga uuacgg                                              26

<210> SEQ ID NO 124
<211> LENGTH: 26
<212> TYPE: RNA
<213> ORGANISM: Artificial Sequence
<220> FEATURE:
<223> OTHER INFORMATION: 26mer of AIMP2-DX2 siRNA #5

<400> SEQUENCE: 124
gcgcuggcca cgugcaggau uacggg                                              26

<210> SEQ ID NO 125
<211> LENGTH: 26
<212> TYPE: RNA
<213> ORGANISM: Artificial Sequence
<220> FEATURE:
<223> OTHER INFORMATION: 26mer of AIMP2-DX2 siRNA #6

<400> SEQUENCE: 125
cgcuggccac gugcaggauu acgggg                                              26

<210> SEQ ID NO 126
<211> LENGTH: 26
<212> TYPE: RNA
<213> ORGANISM: Artificial Sequence
<220> FEATURE:
<223> OTHER INFORMATION: 26mer of AIMP2-DX2 siRNA #7

<400> SEQUENCE: 126
gcuggccacg ugcaggauua cggggc                                              26

<210> SEQ ID NO 127
<211> LENGTH: 26
<212> TYPE: RNA
<213> ORGANISM: Artificial Sequence
<220> FEATURE:
<223> OTHER INFORMATION: 26mer of AIMP2-DX2 siRNA #8

<400> SEQUENCE: 127
cuggccacgu gcaggauuac ggggcg                                              26

<210> SEQ ID NO 128
<211> LENGTH: 26
<212> TYPE: RNA
<213> ORGANISM: Artificial Sequence
<220> FEATURE:
<223> OTHER INFORMATION: 26mer of AIMP2-DX2 siRNA #9

<400> SEQUENCE: 128
uggccacgug caggauuacg ggcgc                                               26
```

```
<210> SEQ ID NO 129
<211> LENGTH: 26
<212> TYPE: RNA
<213> ORGANISM: Artificial Sequence
<220> FEATURE:
<223> OTHER INFORMATION: 26mer of AIMP2-DX2 siRNA #10

<400> SEQUENCE: 129
ggccacgugc aggauuacgg ggcgcu                                      26

<210> SEQ ID NO 130
<211> LENGTH: 26
<212> TYPE: RNA
<213> ORGANISM: Artificial Sequence
<220> FEATURE:
<223> OTHER INFORMATION: 26mer of AIMP2-DX2 siRNA #11

<400> SEQUENCE: 130
gccacgugca ggauuacggg gcgcug                                      26

<210> SEQ ID NO 131
<211> LENGTH: 26
<212> TYPE: RNA
<213> ORGANISM: Artificial Sequence
<220> FEATURE:
<223> OTHER INFORMATION: 26mer of AIMP2-DX2 siRNA #12

<400> SEQUENCE: 131
ccacgugcag gauuacgggg cgcuga                                      26

<210> SEQ ID NO 132
<211> LENGTH: 26
<212> TYPE: RNA
<213> ORGANISM: Artificial Sequence
<220> FEATURE:
<223> OTHER INFORMATION: 26mer of AIMP2-DX2 siRNA #13

<400> SEQUENCE: 132
cacgugcagg auuacggggc gcugaa                                      26

<210> SEQ ID NO 133
<211> LENGTH: 26
<212> TYPE: RNA
<213> ORGANISM: Artificial Sequence
<220> FEATURE:
<223> OTHER INFORMATION: 26mer of AIMP2-DX2 siRNA #14

<400> SEQUENCE: 133
acgugcagga uuacggggcg cugaaa                                      26

<210> SEQ ID NO 134
<211> LENGTH: 26
<212> TYPE: RNA
<213> ORGANISM: Artificial Sequence
<220> FEATURE:
<223> OTHER INFORMATION: 26mer of AIMP2-DX2 siRNA #15

<400> SEQUENCE: 134
cgugcaggau uacggggcgc ugaaag                                      26

<210> SEQ ID NO 135
<211> LENGTH: 26
<212> TYPE: RNA
<213> ORGANISM: Artificial Sequence
<220> FEATURE:
<223> OTHER INFORMATION: 26mer of AIMP2-DX2 siRNA #16
```

```
<400> SEQUENCE: 135
gugcaggauu acggggcgcu gaaaga                                              26

<210> SEQ ID NO 136
<211> LENGTH: 26
<212> TYPE: RNA
<213> ORGANISM: Artificial Sequence
<220> FEATURE:
<223> OTHER INFORMATION: 26mer of AIMP2-DX2 siRNA #17

<400> SEQUENCE: 136
ugcaggauua cggggcgcug aaagac                                              26

<210> SEQ ID NO 137
<211> LENGTH: 27
<212> TYPE: RNA
<213> ORGANISM: Artificial Sequence
<220> FEATURE:
<223> OTHER INFORMATION: 27mer of AIMP2-DX2 siRNA #1

<400> SEQUENCE: 137
gccgggcgcu ggccacgugc aggauua                                             27

<210> SEQ ID NO 138
<211> LENGTH: 27
<212> TYPE: RNA
<213> ORGANISM: Artificial Sequence
<220> FEATURE:
<223> OTHER INFORMATION: 27mer of AIMP2-DX2 siRNA #2

<400> SEQUENCE: 138
ccgggcgcug gccacgugca ggauuac                                             27

<210> SEQ ID NO 139
<211> LENGTH: 27
<212> TYPE: RNA
<213> ORGANISM: Artificial Sequence
<220> FEATURE:
<223> OTHER INFORMATION: 27mer of AIMP2-DX2 siRNA #3

<400> SEQUENCE: 139
cgggcgcugg ccacgugcag gauuacg                                             27

<210> SEQ ID NO 140
<211> LENGTH: 27
<212> TYPE: RNA
<213> ORGANISM: Artificial Sequence
<220> FEATURE:
<223> OTHER INFORMATION: 27mer of AIMP2-DX2 siRNA #4

<400> SEQUENCE: 140
gggcgcuggc cacgugcagg auuacgg                                             27

<210> SEQ ID NO 141
<211> LENGTH: 27
<212> TYPE: RNA
<213> ORGANISM: Artificial Sequence
<220> FEATURE:
<223> OTHER INFORMATION: 27mer of AIMP2-DX2 siRNA #5

<400> SEQUENCE: 141
ggcgcuggcc acgugcagga uuacggg                                             27

<210> SEQ ID NO 142
```

```
<211> LENGTH: 27
<212> TYPE: RNA
<213> ORGANISM: Artificial Sequence
<220> FEATURE:
<223> OTHER INFORMATION: 27mer of AIMP2-DX2 siRNA #6

<400> SEQUENCE: 142
gcgcuggcca cgugcaggau uacgggg                                               27

<210> SEQ ID NO 143
<211> LENGTH: 27
<212> TYPE: RNA
<213> ORGANISM: Artificial Sequence
<220> FEATURE:
<223> OTHER INFORMATION: 27mer of AIMP2-DX2 siRNA #7

<400> SEQUENCE: 143
cgcuggccac gugcaggauu acggggc                                               27

<210> SEQ ID NO 144
<211> LENGTH: 27
<212> TYPE: RNA
<213> ORGANISM: Artificial Sequence
<220> FEATURE:
<223> OTHER INFORMATION: 27mer of AIMP2-DX2 siRNA #8

<400> SEQUENCE: 144
gcuggccacg ugcaggauua cggggcg                                               27

<210> SEQ ID NO 145
<211> LENGTH: 27
<212> TYPE: RNA
<213> ORGANISM: Artificial Sequence
<220> FEATURE:
<223> OTHER INFORMATION: 27mer of AIMP2-DX2 siRNA #9

<400> SEQUENCE: 145
cuggccacgu gcaggauuac ggggcgc                                               27

<210> SEQ ID NO 146
<211> LENGTH: 27
<212> TYPE: RNA
<213> ORGANISM: Artificial Sequence
<220> FEATURE:
<223> OTHER INFORMATION: 27mer of AIMP2-DX2 siRNA #10

<400> SEQUENCE: 146
uggccacgug caggauuacg ggcgcu                                                27

<210> SEQ ID NO 147
<211> LENGTH: 27
<212> TYPE: RNA
<213> ORGANISM: Artificial Sequence
<220> FEATURE:
<223> OTHER INFORMATION: 27mer of AIMP2-DX2 siRNA #11

<400> SEQUENCE: 147
ggccacgugc aggauuacgg ggcgcug                                               27

<210> SEQ ID NO 148
<211> LENGTH: 27
<212> TYPE: RNA
<213> ORGANISM: Artificial Sequence
<220> FEATURE:
<223> OTHER INFORMATION: 27mer of AIMP2-DX2 siRNA #12

<400> SEQUENCE: 148
```
gccacgugca ggauuacggg gcgcuga                                        27

<210> SEQ ID NO 149
<211> LENGTH: 27
<212> TYPE: RNA
<213> ORGANISM: Artificial Sequence
<220> FEATURE:
<223> OTHER INFORMATION: 27mer of AIMP2-DX2 siRNA #13

<400> SEQUENCE: 149
ccacgugcag gauuacgggg cgcugaa                                        27

<210> SEQ ID NO 150
<211> LENGTH: 27
<212> TYPE: RNA
<213> ORGANISM: Artificial Sequence
<220> FEATURE:
<223> OTHER INFORMATION: 27mer of AIMP2-DX2 siRNA #14

<400> SEQUENCE: 150
cacgugcagg auuacggggc gcugaaa                                        27

<210> SEQ ID NO 151
<211> LENGTH: 27
<212> TYPE: RNA
<213> ORGANISM: Artificial Sequence
<220> FEATURE:
<223> OTHER INFORMATION: 27mer of AIMP2-DX2 siRNA #15

<400> SEQUENCE: 151
acgugcagga uuacggggcg cugaaag                                        27

<210> SEQ ID NO 152
<211> LENGTH: 27
<212> TYPE: RNA
<213> ORGANISM: Artificial Sequence
<220> FEATURE:
<223> OTHER INFORMATION: 27mer of AIMP2-DX2 siRNA #16

<400> SEQUENCE: 152
cgugcaggau uacggggcgc ugaaaga                                        27

<210> SEQ ID NO 153
<211> LENGTH: 27
<212> TYPE: RNA
<213> ORGANISM: Artificial Sequence
<220> FEATURE:
<223> OTHER INFORMATION: 27mer of AIMP2-DX2 siRNA #17

<400> SEQUENCE: 153
gugcaggauu acggggcgcu gaaagac                                        27

<210> SEQ ID NO 154
<211> LENGTH: 27
<212> TYPE: RNA
<213> ORGANISM: Artificial Sequence
<220> FEATURE:
<223> OTHER INFORMATION: 27mer of AIMP2-DX2 siRNA #18

<400> SEQUENCE: 154
ugcaggauua cggggcgcug aaagaca                                        27

<210> SEQ ID NO 155
<211> LENGTH: 57
<212> TYPE: DNA

```
<213> ORGANISM: Artificial Sequence
<220> FEATURE:
<223> OTHER INFORMATION: shRNA sequence of mouse AIMP2-DX2

<400> SEQUENCE: 155
tcgagcgggc cacgtgcagg actattcaag agatagtcct gcacgtggcc cgctttt      57

<210> SEQ ID NO 156
<211> LENGTH: 22
<212> TYPE: RNA
<213> ORGANISM: Artificial Sequence
<220> FEATURE:
<223> OTHER INFORMATION: mouse siRNA for AIMP2-DX2

<400> SEQUENCE: 156
gcgggccacg ugcaggacua uu                                              22

<210> SEQ ID NO 157
<211> LENGTH: 28
<212> TYPE: DNA
<213> ORGANISM: Artificial Sequence
<220> FEATURE:
<223> OTHER INFORMATION: AIMP2-F Quantitative PCR Probe

<400> SEQUENCE: 157
cattggtggt taaagtcgtg ggctcatc                                        28

<210> SEQ ID NO 158
<211> LENGTH: 23
<212> TYPE: DNA
<213> ORGANISM: Artificial Sequence
<220> FEATURE:
<223> OTHER INFORMATION: AIMP2-DX2 Quantitative PCR Probe

<400> SEQUENCE: 158
acatcgtgat caacgcaaac ccg                                             23

<210> SEQ ID NO 159
<211> LENGTH: 25
<212> TYPE: DNA
<213> ORGANISM: Artificial Sequence
<220> FEATURE:
<223> OTHER INFORMATION: PAPOLA Quantitative PCR Probe

<400> SEQUENCE: 159
aggcgttgtt tttctgttgg tgcac                                           25

<210> SEQ ID NO 160
<211> LENGTH: 5
<212> TYPE: PRT
<213> ORGANISM: Artificial Sequence
<220> FEATURE:
<223> OTHER INFORMATION: H5 heavy chain CDR1

<400> SEQUENCE: 160

Ser Tyr His Met Thr
  1               5

<210> SEQ ID NO 161
<211> LENGTH: 15
<212> TYPE: DNA
<213> ORGANISM: Artificial Sequence
<220> FEATURE:
<223> OTHER INFORMATION: H5 heavy chain CDR1

<400> SEQUENCE: 161
```
agctaccaca tgacc                                              15

<210> SEQ ID NO 162
<211> LENGTH: 16
<212> TYPE: PRT
<213> ORGANISM: Artificial Sequence
<220> FEATURE:
<223> OTHER INFORMATION: H5 heavy chain CDR2

<400> SEQUENCE: 162

Val Ile Ser Asn Ser Gly Gly Thr Ser Tyr Ala Asn Trp Ala Lys Gly
 1               5                  10                  15

<210> SEQ ID NO 163
<211> LENGTH: 48
<212> TYPE: DNA
<213> ORGANISM: Artificial Sequence
<220> FEATURE:
<223> OTHER INFORMATION: H5 heavy chain CDR2

<400> SEQUENCE: 163
gtcattagta atagtggtgg cacatcctac gcgaactggg cgaaaggc               48

<210> SEQ ID NO 164
<211> LENGTH: 11
<212> TYPE: PRT
<213> ORGANISM: Artificial Sequence
<220> FEATURE:
<223> OTHER INFORMATION: H5 heavy chain CDR3

<400> SEQUENCE: 164

Val Arg Gly Val Pro Gly Ile Asn Ser Asn Leu
 1               5                  10

<210> SEQ ID NO 165
<211> LENGTH: 33
<212> TYPE: DNA
<213> ORGANISM: Artificial Sequence
<220> FEATURE:
<223> OTHER INFORMATION: H5 heavy chain CDR3

<400> SEQUENCE: 165
gtcagagggg tgcctggtat taatagtaac ttg                               33

<210> SEQ ID NO 166
<211> LENGTH: 13
<212> TYPE: PRT
<213> ORGANISM: Artificial Sequence
<220> FEATURE:
<223> OTHER INFORMATION: H5 light chain CDR1

<400> SEQUENCE: 166

Gln Ser Ser Gln Ser Val Tyr Ser Gly Asn Trp Leu Ala
 1               5                  10

<210> SEQ ID NO 167
<211> LENGTH: 39
<212> TYPE: DNA
<213> ORGANISM: Artificial Sequence
<220> FEATURE:
<223> OTHER INFORMATION: H5 light chain CDR1

<400> SEQUENCE: 167
cagtccagtc agagtgttta tagtggcaac tggttagcc                         39

<210> SEQ ID NO 168

```
<211> LENGTH: 7
<212> TYPE: PRT
<213> ORGANISM: Artificial Sequence
<220> FEATURE:
<223> OTHER INFORMATION: H5 light chain CDR2

<400> SEQUENCE: 168

Ser Thr Ser Thr Leu Ala Ser
  1               5

<210> SEQ ID NO 169
<211> LENGTH: 21
<212> TYPE: DNA
<213> ORGANISM: Artificial Sequence
<220> FEATURE:
<223> OTHER INFORMATION: H5 light chain CDR2

<400> SEQUENCE: 169
tctacatcca ctctggcatc t                                              21

<210> SEQ ID NO 170
<211> LENGTH: 10
<212> TYPE: PRT
<213> ORGANISM: Artificial Sequence
<220> FEATURE:
<223> OTHER INFORMATION: H5 light chain CDR3

<400> SEQUENCE: 170

Ala Gly Asp Tyr Asp Gly Tyr Lys Asn Ala
  1               5                  10

<210> SEQ ID NO 171
<211> LENGTH: 30
<212> TYPE: DNA
<213> ORGANISM: Artificial Sequence
<220> FEATURE:
<223> OTHER INFORMATION: H5 light chain CDR3

<400> SEQUENCE: 171
gcaggcgatt atgatggtta caaaaatgct                                     30

<210> SEQ ID NO 172
<211> LENGTH: 115
<212> TYPE: PRT
<213> ORGANISM: Artificial Sequence
<220> FEATURE:
<223> OTHER INFORMATION: H5 heavy chain variable domain (VH)

<400> SEQUENCE: 172

Gln Glu Gln Leu Val Glu Ser Gly Gly Gly Leu Val Thr Pro Gly Gly
  1               5                  10                  15

Thr Leu Thr Leu Thr Cys Thr Ala Ser Gly Phe Thr Ile Ser Ser Tyr
             20                  25                  30

His Met Thr Trp Val Arg Gln Ala Pro Gly Lys Gly Leu Glu Trp Ile
         35                  40                  45

Gly Val Ile Ser Asn Ser Gly Gly Thr Ser Tyr Ala Asn Trp Ala Lys
     50                  55                  60

Gly Arg Phe Thr Ile Ser Lys Thr Ser Thr Thr Val Asp Leu Lys Ile
 65                  70                  75                  80

Thr Ser Pro Thr Thr Glu Asp Thr Ala Thr Tyr Phe Cys Val Arg Gly
                 85                  90                  95

Val Pro Gly Ile Asn Ser Asn Leu Trp Gly Gln Gly Thr Leu Val Thr
            100                 105                 110
```

Ile Ser Ser
        115

<210> SEQ ID NO 173
<211> LENGTH: 345
<212> TYPE: DNA
<213> ORGANISM: Artificial Sequence
<220> FEATURE:
<223> OTHER INFORMATION: H5 heavy chain variable domain (VH)

<400> SEQUENCE: 173
caggagcagc tggtggagtc cggaggaggc ctggtcacgc ctggaggaac cctgacactc      60
acctgcacag cctctggatt caccatcagt agctaccaca tgacctgggt ccgccaggct     120
ccagggaagg ggctggaatg gatcggagtc attagtaata gtggtggcac atcctacgcg     180
aactgggcga aggccgatt caccatctcc aaaacctcga ccacggtgga cctgaaaatc      240
accagtccga caaccgagga cacggccacc tatttctgtg tcagaggggt gcctggtatt     300
aatagtaact gtgggggcca aggcaccctg gtcaccatct cctca                     345

<210> SEQ ID NO 174
<211> LENGTH: 110
<212> TYPE: PRT
<213> ORGANISM: Artificial Sequence
<220> FEATURE:
<223> OTHER INFORMATION: H5 light chain variable domain (VL)

<400> SEQUENCE: 174

Ala Gln Val Leu Thr Gln Thr Pro Ser Val Ser Ala Ala Val Gly
 1               5                  10                  15

Gly Thr Val Thr Ile Asn Cys Gln Ser Ser Gln Ser Val Tyr Ser Gly
                20                  25                  30

Asn Trp Leu Ala Trp Tyr Gln Gln Lys Pro Gly Gln Pro Pro Lys Leu
            35                  40                  45

Leu Ile Tyr Ser Thr Ser Thr Leu Ala Ser Gly Val Pro Ser Arg Phe
        50                  55                  60

Lys Gly Ser Gly Ser Gly Thr Gln Phe Thr Leu Thr Val Ser Asp Leu
 65                 70                  75                  80

Glu Cys Asp Asp Ala Ala Thr Tyr Tyr Cys Ala Gly Asp Tyr Asp Gly
                85                  90                  95

Tyr Lys Asn Ala Phe Gly Gly Gly Thr Lys Val Val Val Lys
            100                 105                 110

<210> SEQ ID NO 175
<211> LENGTH: 330
<212> TYPE: DNA
<213> ORGANISM: Artificial Sequence
<220> FEATURE:
<223> OTHER INFORMATION: H5 light chain variable domain (VL)

<400> SEQUENCE: 175
gctcaagtgc tgacccagac tccatcctcc gtgtctgcag ctgtgggagg cacagtcacc      60
atcaattgcc agtccagtca gagtgtttat agtggcaact ggttagcctg gtatcagcag     120
aaaccagggc agcctcccaa gctcctgatc tattctacat ccactctggc atctggggtc     180
ccatcgcggt tcaaaggcag tggatctggg acacagttca ctctcaccgt cagcgacctg     240
gagtgtgacg atgctgccac ttactactgt gcaggcgatt atgatggtta caaaaatgct     300
ttcggcggag ggaccaaggt ggtcgtcaaa                                      330

```
<210> SEQ ID NO 176
<211> LENGTH: 445
<212> TYPE: PRT
<213> ORGANISM: Artificial Sequence
<220> FEATURE:
<223> OTHER INFORMATION: H5 IgG heavy chain (HC)

<400> SEQUENCE: 176
```

Gln Glu Gln Leu Val Glu Ser Gly Gly Gly Leu Val Thr Pro Gly Gly
 1               5                  10                  15

Thr Leu Thr Leu Thr Cys Thr Ala Ser Gly Phe Thr Ile Ser Ser Tyr
             20                  25                  30

His Met Thr Trp Val Arg Gln Ala Pro Gly Lys Gly Leu Glu Trp Ile
         35                  40                  45

Gly Val Ile Ser Asn Ser Gly Gly Thr Ser Tyr Ala Asn Trp Ala Lys
     50                  55                  60

Gly Arg Phe Thr Ile Ser Lys Thr Ser Thr Thr Val Asp Leu Lys Ile
 65                  70                  75                  80

Thr Ser Pro Thr Thr Glu Asp Thr Ala Thr Tyr Phe Cys Val Arg Gly
                 85                  90                  95

Val Pro Gly Ile Asn Ser Asn Leu Trp Gly Gln Gly Thr Leu Val Thr
            100                 105                 110

Ile Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 177
<211> LENGTH: 1335
<212> TYPE: DNA
<213> ORGANISM: Artificial Sequence
<220> FEATURE:
<223> OTHER INFORMATION: H5 IgG heavy chain (HC)

<400> SEQUENCE: 177

| caggagcagc | tggtggagtc | cggaggaggc | ctggtcacgc | tggaggaac | cctgacactc | 60 |
| acctgcacag | cctctggatt | caccatcagt | agctaccaca | tgacctgggt | ccgccaggct | 120 |
| ccagggaagg | ggctggaatg | gatcggagtc | attagtaata | gtggtggcac | atcctacgcg | 180 |
| aactgggcga | aggccgatt | caccatctcc | aaaacctcga | ccacggtgga | cctgaaaatc | 240 |
| accagtccga | caaccgagga | cacggccacc | tatttctgtg | tcagagggt | gcctggtatt | 300 |
| aatagtaact | tgtggggcca | aggcaccctg | gtcaccatct | cctcagcctc | caccaagggc | 360 |
| ccatcggtct | tccccctggc | accctcctcc | aagagcacct | ctgggggcac | agcggccctg | 420 |
| ggctgcctgg | tcaaggacta | cttccccgaa | ccggtgacgg | tgtcgtggaa | ctcaggcgcc | 480 |
| ctgaccagcg | gcgtgcacac | cttcccggct | gtcctacagt | cctcaggact | ctactccctc | 540 |
| agcagcgtgg | tgaccgtgcc | ctccagcagc | ttgggcaccc | agacctacat | ctgcaacgtg | 600 |
| aatcacaagc | ccagcaacac | caaggtggac | aagaaagttg | agcccaaatc | ttgtgacaaa | 660 |
| actcacacat | gcccaccgtg | cccagcacct | gaactcctgg | ggggaccgtc | agtcttcctc | 720 |
| ttccccccaa | aacccaagga | caccctcatg | atctcccgga | cccctgaggt | cacatgcgtg | 780 |
| gtggtggacg | tgagccacga | agaccctgag | gtcaagttca | actggtacgt | ggacggcgtg | 840 |
| gaggtgcata | atgccaagac | aaagccgcgg | gaggagcagt | acaacagcac | gtaccgtgtg | 900 |
| gtcagcgtcc | tcaccgtcct | gcaccaggac | tggctgaatg | gcaaggagta | caagtgcaag | 960 |
| gtctccaaca | aagccctccc | agcccccatc | gagaaaacca | tctccaaagc | caaagggcag | 1020 |
| ccccgagaac | cacaggtgta | caccctgccc | ccatcccggg | atgagctgac | caagaaccag | 1080 |
| gtcagcctga | cctgcctggt | caaaggcttc | tatcccagcg | acatcgccgt | ggagtgggag | 1140 |
| agcaatgggc | agccggagaa | caactacaag | accacgcctc | ccgtgctgga | ctccgacggc | 1200 |
| tccttcttcc | tctacagcaa | gctcaccgtg | gacaagagca | ggtggcagca | ggggaacgtc | 1260 |
| ttctcatgct | ccgtgatgca | tgaggctctg | cacaaccact | acacgcagaa | gagcctctcc | 1320 |
| ctgtccccgg | gtaaa |  |  |  |  | 1335 |

<210> SEQ ID NO 178
<211> LENGTH: 217
<212> TYPE: PRT
<213> ORGANISM: Artificial Sequence
<220> FEATURE:
<223> OTHER INFORMATION: H5 IgG light chain (LC)

<400> SEQUENCE: 178

```
Ala Gln Val Leu Thr Gln Thr Pro Ser Ser Val Ser Ala Ala Val Gly
 1               5                  10                  15

Gly Thr Val Thr Ile Asn Cys Gln Ser Ser Gln Ser Val Tyr Ser Gly
                 20                  25                  30

Asn Trp Leu Ala Trp Tyr Gln Gln Lys Pro Gly Gln Pro Pro Lys Leu
             35                  40                  45

Leu Ile Tyr Ser Thr Ser Thr Leu Ala Ser Gly Val Pro Ser Arg Phe
         50                  55                  60

Lys Gly Ser Gly Ser Gly Thr Gln Phe Thr Leu Thr Val Ser Asp Leu
 65                  70                  75                  80

Glu Cys Asp Asp Ala Ala Thr Tyr Tyr Cys Ala Gly Asp Tyr Asp Gly
                 85                  90                  95

Tyr Lys Asn Ala Phe Gly Gly Gly Thr Lys Val Val Lys Arg Thr
             100                 105                 110

Val Ala Ala Pro Ser Val Phe Ile Phe Pro Pro Ser Asp Glu Gln Leu
         115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Gly Lys Ala Asp Tyr Glu Lys His
            180                 185                 190

Lys Val Tyr Ala Cys Glu Val Thr His Gln Gly Leu Ser Leu Pro Val
            195                 200                 205

Thr Lys Ser Phe Asn Arg Gly Glu Cys
        210                 215

<210> SEQ ID NO 179
<211> LENGTH: 651
<212> TYPE: DNA
<213> ORGANISM: Artificial Sequence
<220> FEATURE:
<223> OTHER INFORMATION: H5 IgG light chain (LC)

<400> SEQUENCE: 179
gctcaagtgc tgacccagac tccatcctcc gtgtctgcag ctgtgggagg cacagtcacc      60
atcaattgcc agtccagtca gagtgtttat agtggcaact ggttagcctg gtatcagcag     120
aaaccagggc agcctcccaa gctcctgatc tattctacat ccactctggc atctggggtc     180
ccatcgcggt tcaaaggcag tggatctggg acacagttca ctctcaccgt cagcgacctg     240
gagtgtgacg atgctgccac ttactactgt gcaggcgatt atgatggtta caaaaatgct     300
ttcggcggag ggaccaaggt ggtcgtcaaa cgaactgtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgggcaaagc agactacgag aaacacaaag tctacgcctg cgaagtcacc     600
catcagggcc tgagcttgcc cgtcacaaag agcttcaaca ggggagagtg t             651

<210> SEQ ID NO 180
<211> LENGTH: 221
<212> TYPE: PRT
```

<213> ORGANISM: Artificial Sequence
<220> FEATURE:
<223> OTHER INFORMATION: H5 Fd heavy chain (heavy chain portion of H5 Fab)

<400> SEQUENCE: 180

```
Gln Glu Gln Leu Val Glu Ser Gly Gly Gly Leu Val Thr Pro Gly Gly
  1               5                  10                  15

Thr Leu Thr Leu Thr Cys Thr Ala Ser Gly Phe Thr Ile Ser Ser Tyr
             20                  25                  30

His Met Thr Trp Val Arg Gln Ala Pro Gly Lys Gly Leu Glu Trp Ile
         35                  40                  45

Gly Val Ile Ser Asn Ser Gly Thr Ser Tyr Ala Asn Trp Ala Lys
 50                  55                  60

Gly Arg Phe Thr Ile Ser Lys Thr Ser Thr Thr Val Asp Leu Lys Ile
 65                  70                  75                  80

Thr Ser Pro Thr Thr Glu Asp Thr Ala Thr Tyr Phe Cys Val Arg Gly
             85                  90                  95

Val Pro Gly Ile Asn Ser Asn Leu Trp Gly Gln Gly Thr Leu Val Thr
            100                 105                 110

Ile Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr
    210                 215                 220
```

<210> SEQ ID NO 181
<211> LENGTH: 663
<212> TYPE: DNA
<213> ORGANISM: Artificial Sequence
<220> FEATURE:
<223> OTHER INFORMATION: H5 Fd heavy chain (heavy chain portion of H5 Fab)

<400> SEQUENCE: 181

```
caggagcagc tggtggagtc cggaggaggc ctggtcacgc ctggaggaac cctgacactc      60
acctgcacag cctctggatt caccatcagt agctaccaca tgacctgggt ccgccaggct     120
ccagggaagg ggctggaatg gatcggagtc attagtaata gtggtggcac atcctacgcg     180
aactgggcga aaggccgatt caccatctcc aaaacctcga ccacggtgga cctgaaaatc     240
accagtccga caaccgagga cacggccacc tatttctgtg tcagagggggt gcctggtatt     300
aatagtaact tgtggggcca aggcaccctg gtcaccatct cctcagcctc caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttccgggct gtcctacagt cctcaggact ctactccctc     540
agcagcgtgg tgaccgtgcc ctccagcagc ttgggcaccc agacctacat ctgcaacgtg     600
```

```
aatcacaagc ccagcaacac caaggtggac aagaaagttg agcccaaatc ttgtgacaaa    660
act                                                                  663
```

<210> SEQ ID NO 182
<211> LENGTH: 35
<212> TYPE: DNA
<213> ORGANISM: Artificial Sequence
<220> FEATURE:
<223> OTHER INFORMATION: RVH1 primer

<400> SEQUENCE: 182

```
gcccaaccag ccatggccca ggagcagcta aggag                               35
```

<210> SEQ ID NO 183
<211> LENGTH: 36
<212> TYPE: DNA
<213> ORGANISM: Artificial Sequence
<220> FEATURE:
<223> OTHER INFORMATION: RVH2 primer

<400> SEQUENCE: 183

```
gcccaaccag ccatggccca ggagcagctg rtggag                              36
```

<210> SEQ ID NO 184
<211> LENGTH: 39
<212> TYPE: DNA
<213> ORGANISM: Artificial Sequence
<220> FEATURE:
<223> OTHER INFORMATION: RVH3 primer

<400> SEQUENCE: 184

```
gcccaaccag ccatggccca ggagcagctg gaggagtcc                           39
```

<210> SEQ ID NO 185
<211> LENGTH: 36
<212> TYPE: DNA
<213> ORGANISM: Artificial Sequence
<220> FEATURE:
<223> OTHER INFORMATION: RVH4 primer

<400> SEQUENCE: 185

```
gcccaaccag ccatggccca gtcgstggag gagtcc                              36
```

<210> SEQ ID NO 186
<211> LENGTH: 36
<212> TYPE: DNA
<213> ORGANISM: Artificial Sequence
<220> FEATURE:
<223> OTHER INFORMATION: RVH5 primer

<400> SEQUENCE: 186

```
gcccaaccag ccatggccca gtcggtgaag gagtcc                              36
```

<210> SEQ ID NO 187
<211> LENGTH: 36
<212> TYPE: DNA
<213> ORGANISM: Artificial Sequence
<220> FEATURE:
<223> OTHER INFORMATION: RVH6 primer

<400> SEQUENCE: 187

```
gcccaaccag ccatggccca gcagctggag cagtcc                              36
```

<210> SEQ ID NO 188

```
<211> LENGTH: 36
<212> TYPE: DNA
<213> ORGANISM: Artificial Sequence
<220> FEATURE:
<223> OTHER INFORMATION: RVK1 primer

<400> SEQUENCE: 188
taattggccc aggcggccga ccctatgctg acccag                              36

<210> SEQ ID NO 189
<211> LENGTH: 36
<212> TYPE: DNA
<213> ORGANISM: Artificial Sequence
<220> FEATURE:
<223> OTHER INFORMATION: RVK2 primer

<400> SEQUENCE: 189
taattggccc aggcggccga tgtcgtgatg acccag                              36

<210> SEQ ID NO 190
<211> LENGTH: 36
<212> TYPE: DNA
<213> ORGANISM: Artificial Sequence
<220> FEATURE:
<223> OTHER INFORMATION: RVK3 primer

<400> SEQUENCE: 190
taattggccc aggcggccgc agccgtgctg acccag                              36

<210> SEQ ID NO 191
<211> LENGTH: 36
<212> TYPE: DNA
<213> ORGANISM: Artificial Sequence
<220> FEATURE:
<223> OTHER INFORMATION: RVK4 primer

<400> SEQUENCE: 191
taattggccc aggcggccgc catcgatatg acccag                              36

<210> SEQ ID NO 192
<211> LENGTH: 36
<212> TYPE: DNA
<213> ORGANISM: Artificial Sequence
<220> FEATURE:
<223> OTHER INFORMATION: RVK5 primer

<400> SEQUENCE: 192
taattggccc aggcggccgc ccaagtgctg acccag                              36

<210> SEQ ID NO 193
<211> LENGTH: 36
<212> TYPE: DNA
<213> ORGANISM: Artificial Sequence
<220> FEATURE:
<223> OTHER INFORMATION: RVK6 primer

<400> SEQUENCE: 193
taattggccc aggcggccgc ccttgtgatg acccag                              36

<210> SEQ ID NO 194
<211> LENGTH: 36
<212> TYPE: DNA
<213> ORGANISM: Artificial Sequence
<220> FEATURE:
<223> OTHER INFORMATION: RVK7 primer

<400> SEQUENCE: 194
```

```
taattggccc aggcggccgc tcaagtgctg acccag                              36
```

<210> SEQ ID NO 195
<211> LENGTH: 36
<212> TYPE: DNA
<213> ORGANISM: Artificial Sequence
<220> FEATURE:
<223> OTHER INFORMATION: RVK8 primer

<400> SEQUENCE: 195

```
taattggccc aggcggccta tgtcatgatg acccag                              36
```

<210> SEQ ID NO 196
<211> LENGTH: 36
<212> TYPE: DNA
<213> ORGANISM: Artificial Sequence
<220> FEATURE:
<223> OTHER INFORMATION: RVL1 primer

<400> SEQUENCE: 196

```
taattggccc aggcggccca gcctgccctc actcag                              36
```

<210> SEQ ID NO 197
<211> LENGTH: 36
<212> TYPE: DNA
<213> ORGANISM: Artificial Sequence
<220> FEATURE:
<223> OTHER INFORMATION: RVL2 primer

<400> SEQUENCE: 197

```
taattggccc aggcggcctc ctatgagctg acacag                              36
```

<210> SEQ ID NO 198
<211> LENGTH: 36
<212> TYPE: DNA
<213> ORGANISM: Artificial Sequence
<220> FEATURE:
<223> OTHER INFORMATION: RVL3 primer

<400> SEQUENCE: 198

```
taattggccc aggcggcctc cttcgtgctg actcag                              36
```

<210> SEQ ID NO 199
<211> LENGTH: 36
<212> TYPE: DNA
<213> ORGANISM: Artificial Sequence
<220> FEATURE:
<223> OTHER INFORMATION: RVL4 primer

<400> SEQUENCE: 199

```
taattggccc aggcggccca gcctgtgctg actcag                              36
```

<210> SEQ ID NO 200
<211> LENGTH: 36
<212> TYPE: DNA
<213> ORGANISM: Artificial Sequence
<220> FEATURE:
<223> OTHER INFORMATION: RVL5 primer

<400> SEQUENCE: 200

```
taattggccc aggcggccag cgttgtgttc acgcag                              36
```

<210> SEQ ID NO 201
<211> LENGTH: 36
<212> TYPE: DNA

```
<213> ORGANISM: Artificial Sequence
<220> FEATURE:
<223> OTHER INFORMATION: RVL6 primer

<400> SEQUENCE: 201
taattggccc aggcggccca gtttgtgctg actcag                                 36

<210> SEQ ID NO 202
<211> LENGTH: 39
<212> TYPE: DNA
<213> ORGANISM: Artificial Sequence
<220> FEATURE:
<223> OTHER INFORMATION: RJH-b primer

<400> SEQUENCE: 202
tgggcccttg gtggaggctg argagayggt gaccagggt                              39

<210> SEQ ID NO 203
<211> LENGTH: 39
<212> TYPE: DNA
<213> ORGANISM: Artificial Sequence
<220> FEATURE:
<223> OTHER INFORMATION: RJK1-b primer

<400> SEQUENCE: 203
agatggtgca gccacagttc gtttgatttc cacattggt                              39

<210> SEQ ID NO 204
<211> LENGTH: 39
<212> TYPE: DNA
<213> ORGANISM: Artificial Sequence
<220> FEATURE:
<223> OTHER INFORMATION: RJK2-b primer

<400> SEQUENCE: 204
agatggtgca gccacagttc gttygacsac cacctyggt                              39

<210> SEQ ID NO 205
<211> LENGTH: 39
<212> TYPE: DNA
<213> ORGANISM: Artificial Sequence
<220> FEATURE:
<223> OTHER INFORMATION: RJK3-b primer

<400> SEQUENCE: 205
agatggtgca gccacagttc gtaggatctc cagctcggt                              39

<210> SEQ ID NO 206
<211> LENGTH: 39
<212> TYPE: DNA
<213> ORGANISM: Artificial Sequence
<220> FEATURE:
<223> OTHER INFORMATION: RJK4-b primer

<400> SEQUENCE: 206
agatggtgca gccacagttc gtttgatytc cascttggt                              39

<210> SEQ ID NO 207
<211> LENGTH: 42
<212> TYPE: DNA
<213> ORGANISM: Artificial Sequence
<220> FEATURE:
<223> OTHER INFORMATION: RJL-b primer

<400> SEQUENCE: 207
agatggtgca gccacagttc ggcctgtgac ggtcagctgg gt                          42
```

<210> SEQ ID NO 208
<211> LENGTH: 18
<212> TYPE: DNA
<213> ORGANISM: Artificial Sequence
<220> FEATURE:
<223> OTHER INFORMATION: HIgCH1-f primer

<400> SEQUENCE: 208
gcctccacca agggccca                                                 18

<210> SEQ ID NO 209
<211> LENGTH: 19
<212> TYPE: DNA
<213> ORGANISM: Artificial Sequence
<220> FEATURE:
<223> OTHER INFORMATION: dpseq primer

<400> SEQUENCE: 209
agaagcgtag tccggaacg                                                19

<210> SEQ ID NO 210
<211> LENGTH: 19
<212> TYPE: DNA
<213> ORGANISM: Artificial Sequence
<220> FEATURE:
<223> OTHER INFORMATION: HKC-f primer

<400> SEQUENCE: 210
actgtggctg caccatctg                                                19

<210> SEQ ID NO 211
<211> LENGTH: 18
<212> TYPE: DNA
<213> ORGANISM: Artificial Sequence
<220> FEATURE:
<223> OTHER INFORMATION: Lead-b primer

<400> SEQUENCE: 211
ggccatggct ggttgggc                                                 18

<210> SEQ ID NO 212
<211> LENGTH: 18
<212> TYPE: DNA
<213> ORGANISM: Artificial Sequence
<220> FEATURE:
<223> OTHER INFORMATION: LeadVH primer

<400> SEQUENCE: 212
gcccaaccag ccatggcc                                                 18

<210> SEQ ID NO 213
<211> LENGTH: 18
<212> TYPE: DNA
<213> ORGANISM: Artificial Sequence
<220> FEATURE:
<223> OTHER INFORMATION: RSC-SF primer

<400> SEQUENCE: 213
taattggccc aggcggcc                                                 18

<210> SEQ ID NO 214
<211> LENGTH: 19
<212> TYPE: DNA
<213> ORGANISM: Artificial Sequence
<220> FEATURE:

```
<223> OTHER INFORMATION: siDX2 siRNA

<400> SEQUENCE: 214
ctggccacgt gcaggatta                                                 19

<210> SEQ ID NO 215
<211> LENGTH: 19
<212> TYPE: DNA
<213> ORGANISM: Artificial Sequence
<220> FEATURE:
<223> OTHER INFORMATION: si exon4 #1 siRNA

<400> SEQUENCE: 215
ggaacattgc acgtttctt                                                 19

<210> SEQ ID NO 216
<211> LENGTH: 19
<212> TYPE: DNA
<213> ORGANISM: Artificial Sequence
<220> FEATURE:
<223> OTHER INFORMATION: si exon4 #2 siRNA

<400> SEQUENCE: 216
gctgtcaacg caaccctta                                                 19

<210> SEQ ID NO 217
<211> LENGTH: 312
<212> TYPE: PRT
<213> ORGANISM: Artificial Sequence
<220> FEATURE:
<223> OTHER INFORMATION: AIMP2-312 amino acids

<400> SEQUENCE: 217
```

Met Pro Met Tyr Gln Val Lys Pro Tyr His Gly Gly Gly Ala Pro Leu
 1               5                  10                  15

Arg Val Glu Leu Pro Thr Cys Met Tyr Arg Leu Pro Asn Val His Gly
            20                  25                  30

Arg Ser Tyr Gly Pro Ala Pro Gly Ala Gly His Val Gln Glu Glu Ser
        35                  40                  45

Asn Leu Ser Leu Gln Ala Leu Glu Ser Arg Gln Asp Asp Ile Leu Lys
    50                  55                  60

Arg Leu Tyr Glu Leu Lys Ala Ala Val Asp Gly Leu Ser Lys Met Ile
65                  70                  75                  80

Gln Thr Pro Asp Ala Asp Leu Asp Val Thr Asn Ile Ile Gln Ala Asp
                85                  90                  95

Glu Pro Thr Thr Leu Thr Thr Asn Ala Leu Asp Leu Asn Ser Val Leu
            100                 105                 110

Gly Lys Asp Tyr Gly Ala Leu Lys Asp Ile Val Ile Asn Ala Asn Pro
        115                 120                 125

Ala Ser Pro Pro Leu Ser Leu Leu Val Leu His Arg Leu Leu Cys Glu
    130                 135                 140

His Phe Arg Val Leu Ser Thr Val His Thr His Ser Ser Val Lys Ser
145                 150                 155                 160

Val Pro Glu Asn Leu Leu Lys Cys Phe Gly Glu Gln Asn Lys Lys Gln
                165                 170                 175

Pro Arg Gln Asp Tyr Gln Leu Gly Phe Thr Leu Ile Trp Lys Asn Val
            180                 185                 190

Pro Lys Thr Gln Met Lys Phe Ser Ile Gln Thr Met Cys Pro Ile Glu
        195                 200                 205

```
Gly Glu Gly Asn Ile Ala Arg Phe Leu Phe Ser Leu Phe Gly Gln Lys
210                 215                 220

His Asn Ala Val Asn Ala Thr Leu Ile Asp Ser Trp Val Asp Ile Ala
225                 230                 235                 240

Ile Phe Gln Leu Lys Glu Gly Ser Ser Lys Glu Lys Ala Ala Val Phe
                245                 250                 255

Arg Ser Met Asn Ser Ala Leu Gly Lys Ser Pro Trp Leu Ala Gly Asn
            260                 265                 270

Glu Leu Thr Val Ala Asp Val Leu Trp Ser Val Leu Gln Gln Ile
        275                 280                 285

Gly Gly Cys Ser Val Thr Val Pro Ala Asn Val Gln Arg Trp Met Arg
290                 295                 300

Ser Cys Glu Asn Leu Ala Pro Phe
305                 310

<210> SEQ ID NO 218
<211> LENGTH: 320
<212> TYPE: PRT
<213> ORGANISM: Artificial Sequence
<220> FEATURE:
<223> OTHER INFORMATION: AIMP2-320 amino acids

<400> SEQUENCE: 218

Met Pro Met Tyr Gln Val Lys Pro Tyr His Gly Gly Gly Ala Pro Leu
1               5                   10                  15

Arg Val Glu Leu Pro Thr Cys Met Tyr Arg Leu Pro Asn Val His Gly
            20                  25                  30

Arg Ser Tyr Gly Pro Ala Pro Gly Ala Gly His Val Gln Glu Glu Ser
        35                  40                  45

Asn Leu Ser Leu Gln Ala Leu Glu Ser Arg Gln Asp Asp Ile Leu Lys
    50                  55                  60

Arg Leu Tyr Glu Leu Lys Ala Ala Val Asp Gly Leu Ser Lys Met Ile
65                  70                  75                  80

Gln Thr Pro Asp Ala Asp Leu Asp Val Thr Asn Ile Ile Gln Ala Asp
                85                  90                  95

Glu Pro Thr Thr Leu Thr Thr Asn Ala Leu Asp Leu Asn Ser Val Leu
            100                 105                 110

Gly Lys Asp Tyr Gly Ala Leu Lys Asp Ile Val Ile Asn Ala Asn Pro
        115                 120                 125

Gly Ser Pro Pro Leu Ser Leu Leu Val Leu His Arg Leu Leu Cys Glu
130                 135                 140

His Phe Arg Val Leu Ser Thr Val His Thr His Ser Ser Val Lys Ser
145                 150                 155                 160

Val Pro Glu Asn Leu Leu Lys Cys Phe Gly Glu Gln Asn Lys Lys Gln
                165                 170                 175

Pro Arg Gln Asp Tyr Gln Leu Gly Phe Thr Leu Ile Trp Lys Asn Val
            180                 185                 190

Pro Lys Thr Gln Met Lys Phe Ser Ile Gln Thr Met Cys Pro Ile Glu
        195                 200                 205

Gly Glu Gly Asn Ile Ala Arg Phe Leu Phe Ser Leu Phe Gly Gln Lys
210                 215                 220

His Asn Ala Val Asn Ala Thr Leu Ile Asp Ser Trp Val Asp Ile Ala
225                 230                 235                 240

Ile Phe Gln Leu Lys Glu Gly Ser Ser Lys Glu Lys Ala Ala Val Phe
                245                 250                 255
```

```
Arg Ser Met Asn Ser Ala Leu Gly Lys Ser Pro Trp Leu Ala Gly Asn
            260                 265                 270

Glu Leu Thr Val Ala Asp Val Val Leu Trp Ser Val Leu Gln Gln Ile
        275                 280                 285

Gly Gly Cys Ser Val Thr Val Pro Ala Asn Val Gln Arg Trp Met Arg
    290                 295                 300

Ser Cys Glu Asn Leu Ala Pro Phe Asn Thr Ala Leu Lys Leu Leu Lys
305                 310                 315                 320

<210> SEQ ID NO 219
<211> LENGTH: 11
<212> TYPE: PRT
<213> ORGANISM: Artificial Sequence
<220> FEATURE:
<223> OTHER INFORMATION: AIMP2-DX2 amino acid residues 42-52

<400> SEQUENCE: 219

Gly His Val Gln Asp Tyr Gly Ala Leu Lys Asp
  1               5                   10

<210> SEQ ID NO 220
<211> LENGTH: 4
<212> TYPE: PRT
<213> ORGANISM: Artificial Sequence
<220> FEATURE:
<223> OTHER INFORMATION: AIMP2-DX2 N-terminal exon #1

<400> SEQUENCE: 220

Gly His Val Gln
  1

<210> SEQ ID NO 221
<211> LENGTH: 7
<212> TYPE: PRT
<213> ORGANISM: Artificial Sequence
<220> FEATURE:
<223> OTHER INFORMATION: AIMP2-DX2 C-terminal exon #3

<400> SEQUENCE: 221

Asp Tyr Gly Ala Leu Lys Asp
  1               5
```